United States Patent
Kovtun et al.

(10) Patent No.: US 10,932,860 B2
(45) Date of Patent: Mar. 2, 2021

(54) SYSTEMS, METHODS, AND MEDIA FOR PRESENTING MEDICAL IMAGING DATA IN AN INTERACTIVE VIRTUAL REALITY ENVIRONMENT

(71) Applicant: THE BRIGHAM AND WOMEN'S HOSPITAL, INC., Boston, MA (US)

(72) Inventors: Konstantin Kovtun, Cambridge, MA (US); Christopher Williams, Cambridge, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 16/609,055

(22) PCT Filed: Apr. 30, 2018

(86) PCT No.: PCT/US2018/030311
§ 371 (c)(1),
(2) Date: Oct. 28, 2019

(87) PCT Pub. No.: WO2018/201155
PCT Pub. Date: Nov. 1, 2018

(65) Prior Publication Data
US 2020/0054398 A1 Feb. 20, 2020

Related U.S. Application Data
(60) Provisional application No. 62/491,859, filed on Apr. 28, 2017.

(51) Int. Cl.
*G09G 5/00* (2006.01)
*A61B 34/10* (2016.01)
(Continued)

(52) U.S. Cl.
CPC .............. *A61B 34/10* (2016.02); *G06T 11/20* (2013.01); *G06T 19/20* (2013.01); *G16H 30/40* (2018.01);
(Continued)

(58) Field of Classification Search
CPC ..... G06T 15/08; G06T 15/06; G06T 2210/41; G06T 17/00; G06T 2200/08; G06T 19/20;
(Continued)

(56) References Cited

U.S. PATENT DOCUMENTS 8,368,694 B2 * 2/2013 Novosad ................. G06T 15/06
345/426
2009/0027382 A1 1/2009 Yang
(Continued)

FOREIGN PATENT DOCUMENTS

WO 2017066373 A1 4/2017

OTHER PUBLICATIONS

Blot, W. J. Rising Incidence of Adenocarcinoma of the Esophagus and nGastric Cardia. JAMA J. Am. Med. Assoc. 265, 1287 (1991).
(Continued)

*Primary Examiner* — Hau H Nguyen
(74) *Attorney, Agent, or Firm* — Quarles & Brady LLP

(57) ABSTRACT

Systems, methods, and media for presenting medical imaging data in an interactive virtual environment reality are provided. In some embodiments, a system comprises a head mounted display (HMD) that: determines that a transparent 3D object overlaps a 3D model of a portion of anatomy based on a medical imaging scan; sets values for pixels corresponding to portions of the 3D model not occluded by the transparent object by performing a shading operation; sets values for pixels corresponding to portions of the 3D model at the boundary of the transparent object to intensity values taken from the medical imaging data; displays the 3D
(Continued)

model with an exterior surface shaded to evoke a 3D object, and internal surfaces at the boundaries of the transparent object not shaded to preserve details embedded in the medical imaging data.

21 Claims, 30 Drawing Sheets

(51) Int. Cl.
G16H 50/50 (2018.01)
G16H 30/40 (2018.01)
G06T 11/20 (2006.01)
G06T 19/20 (2011.01)

(52) U.S. Cl.
CPC ........ G16H 50/50 (2018.01); A61B 2034/104 (2016.02); A61B 2034/105 (2016.02)

(58) Field of Classification Search
CPC . G06T 7/0012; G06T 19/003; G06T 2210/12; G06T 2219/2004; A61B 34/10; A61B 2034/104; A61B 8/483
See application file for complete search history.

(56) References Cited

U.S. PATENT DOCUMENTS

| 2014/0192054 A1* | 7/2014 | Yoo ........................ G06T 15/50 345/426 |
| 2017/0035517 A1 | 2/2017 | Geri et al. |
| 2017/0065352 A1 | 3/2017 | Razzaque et al. |

OTHER PUBLICATIONS

Burman, C., et al. Fitting of normal tissue tolerance data to an analytic function. Int. J. Radiat. Oncol. Biol. Phys. 21, 123-135 (1991).
Davis, F. D. User acceptance of information technology: system characteristics, user perceptions and behavioral impacts. Int. J. Man-Mach. Stud. 38, 475-487 (1993).
De Manzioni, G. et al. Pattern of recurrence after surgery in adenocarcinoma of the gastro-oesophageal junction. Eur. J. Surg. Oncol. J. Eur. Soc. Surg. Oncol. Br. Assoc. Surg. Oncol. 29, 506-510 (2003).
Devesa, S. S., et al. Changing patterns in the incidence of esophageal and gastric carcinoma in the United States. Cancer 83, 2049-2053 (1998).
Feng, M. et al. Dosimetric analysis of radiation-induced gastric bleeding. Int. J. Radial Oncol. Biol. Phys. 84, e1-6 (2012).
Fishman, E. K. et al. Volume Rendering versus Maximum Intensity Projection in CT Angiography: What Works Best, When, and Why. RadioGraphics 26, 905-922 (2006).
Gao, X.-S. et al. Pathological analysis of clinical target volume margin for radiotherapy in patients with esophageal and gastroesophageal junction carcinoma. Int. J. Radiat. Oncol. Biol. Phys. 67, 389-396 (2007).
International Searching Authority, International Search Report and Written Opinion for application PCT/US2018/030311, dated Jul. 6, 2018.
Keeney, S. et al. Epidemiology of adenocarcinoma of the esophagogastric junction. Surg. Oncol. Clin. N. Am. 15, 687-696 (2006).
Kelsen, D. P. et al. Chemotherapy followed by surgery compared with surgery alone for localized esophageal cancer. N. Engl. J. Med. 339, 1979-1984 (1998).
La Macchia, M. et al. Systematic evaluation of three different commercial software solutions for automatic segmentation for adaptive therapy in head-and-neck, prostate and pleural cancer. Radial Oncol. Lond. Engl. 7, 160 (2012).
Maehara, Y. et al. Postoperative outcome and sites of recurrence in patients following curative resection of gastric cancer. Br. J. Surg. 87, 353-357 (2000).
Nelms, B. E., et al. Variations in the contouring of organs at risk: test case from a patient with oropharyngeal cancer. Int. J. Radial Oncol. Biol. Phys. 82, 368-378 (2012).
Oppedijk, V. et al. Patterns of Recurrence After Surgery Alone Versus Preoperative Chemoradiotherapy and Surgery in the CROSS Trials. J. Clin. Oncol. 32, 385-391 (2014).
Sato, Y., et al. Local maximum intensity projection (LMIP): a new rendering method for vascular visualization. J. Comput. Assist. Tomogr. 22, 912-917 (1998).
Shapiro, J. et al. Neoadjuvant chemoradiotherapy plus surgery versus surgery alone for oesophageal or junctional cancer (CROSS): long-term results of a randomised controlled trial. Lancet Oncol. 16, 1090-1098 (2015).
Van Hagen, P. et al. Preoperative chemoradiotherapy for esophageal or junctional cancer. N. Engl. J. Med. 366, 2074-2084 (2012).
Wallis, J. W. et al. Three-dimensional display in nuclear medicine and radiology. J. Nucl. Med. Off. Publ. Soc. Nucl. Med. 32, 534-546 (1991).
Wingfield, N. et al. Facebook in $2 Billion Deal for Virtual Reality Company. The New York Times (2014).
Wu, A. J. et al. Expert Consensus Contouring Guidelines for Intensity Modulated Radiation Therapy in Esophageal and Gastroesophageal Junction Cancer. Int. J. Radiat. Oncol. 92, 911-920 (2015).
Zheng, Y., et al. 3D Printout Models vs. 3D-Rendered Images: Which is Better for Preoperative Planning? J. Surg. Educ. 73, 518-523 (2016).

* cited by examiner

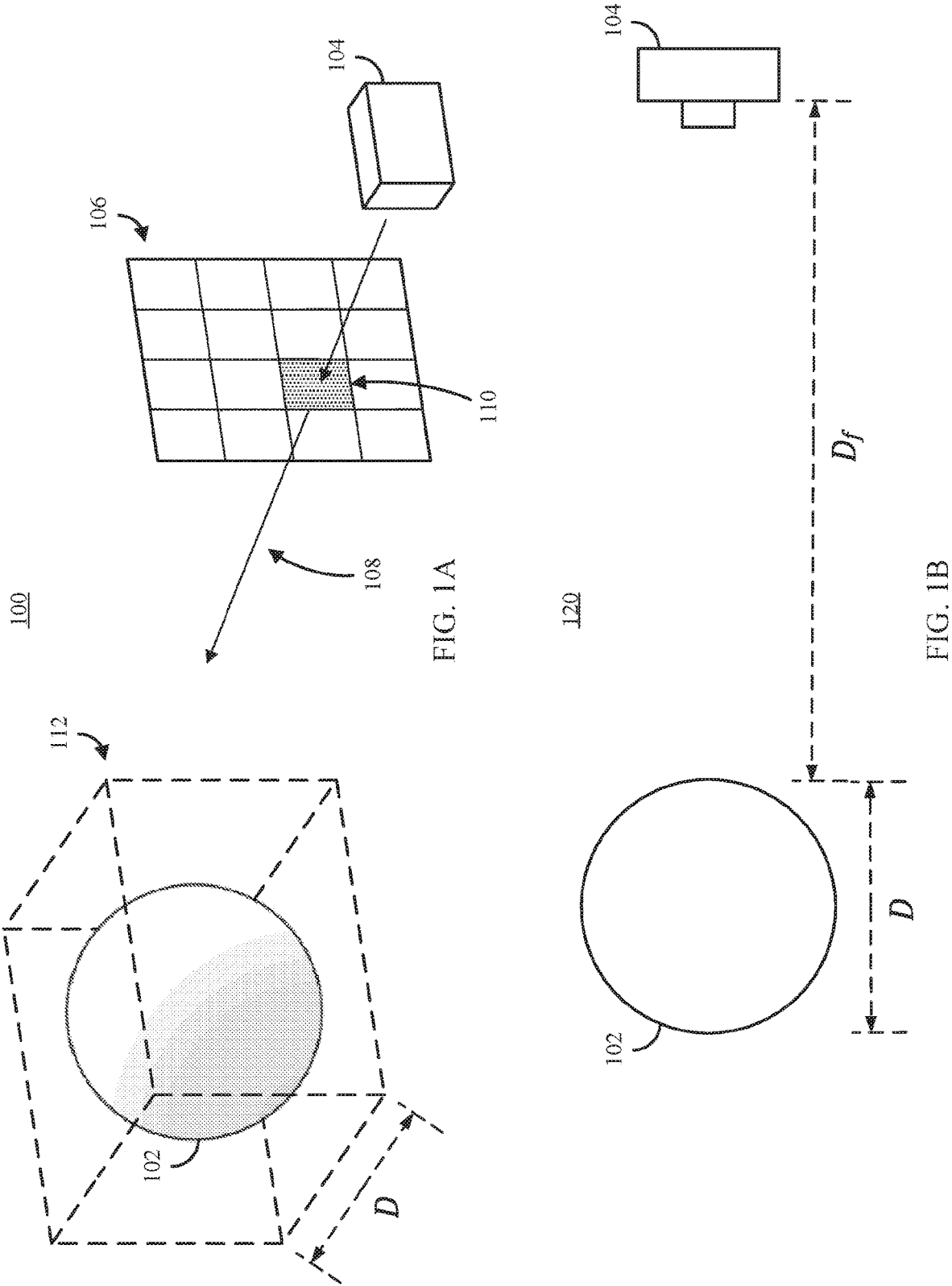

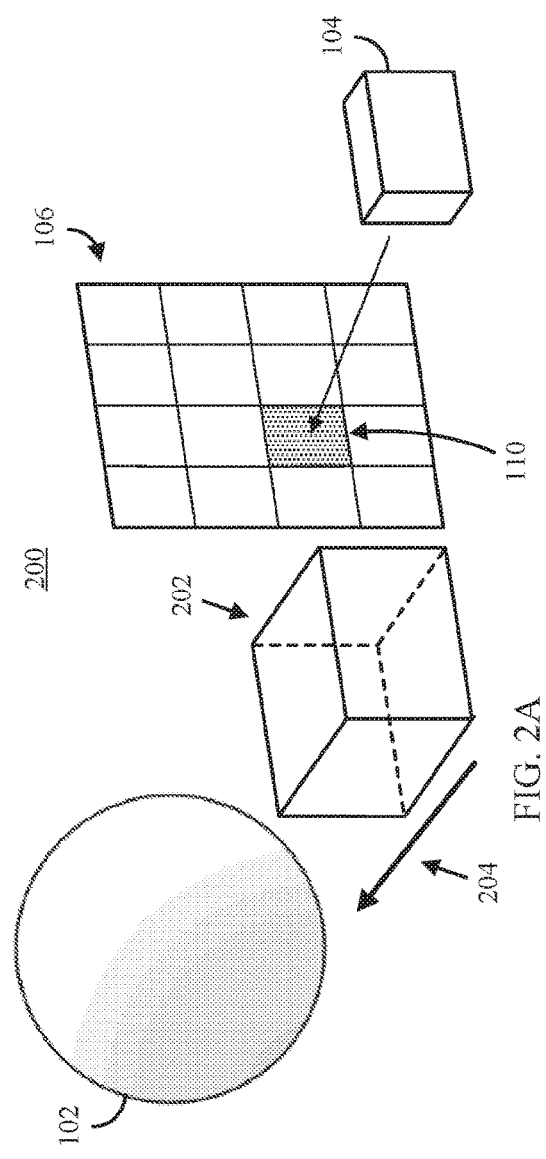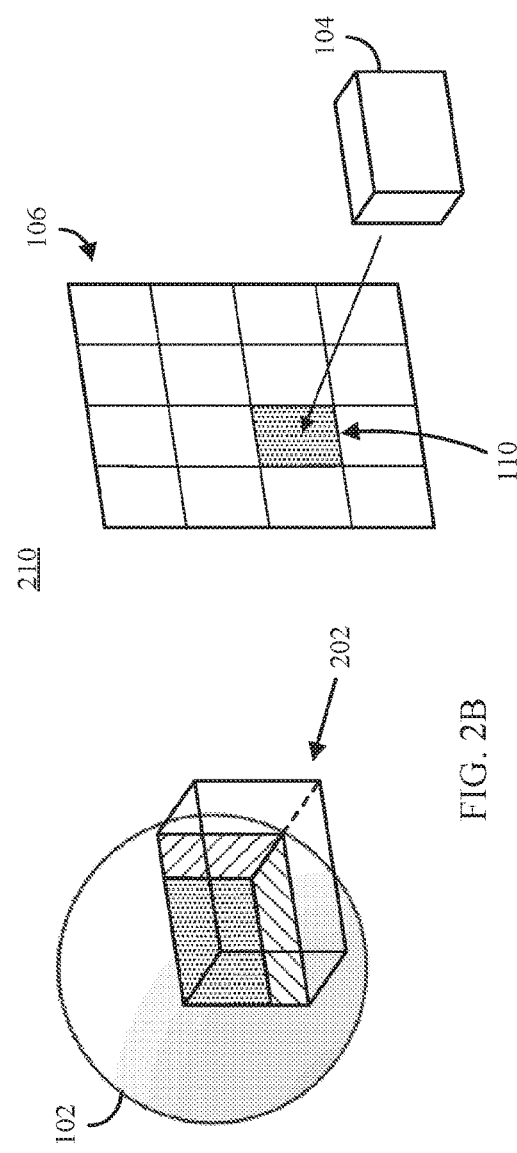

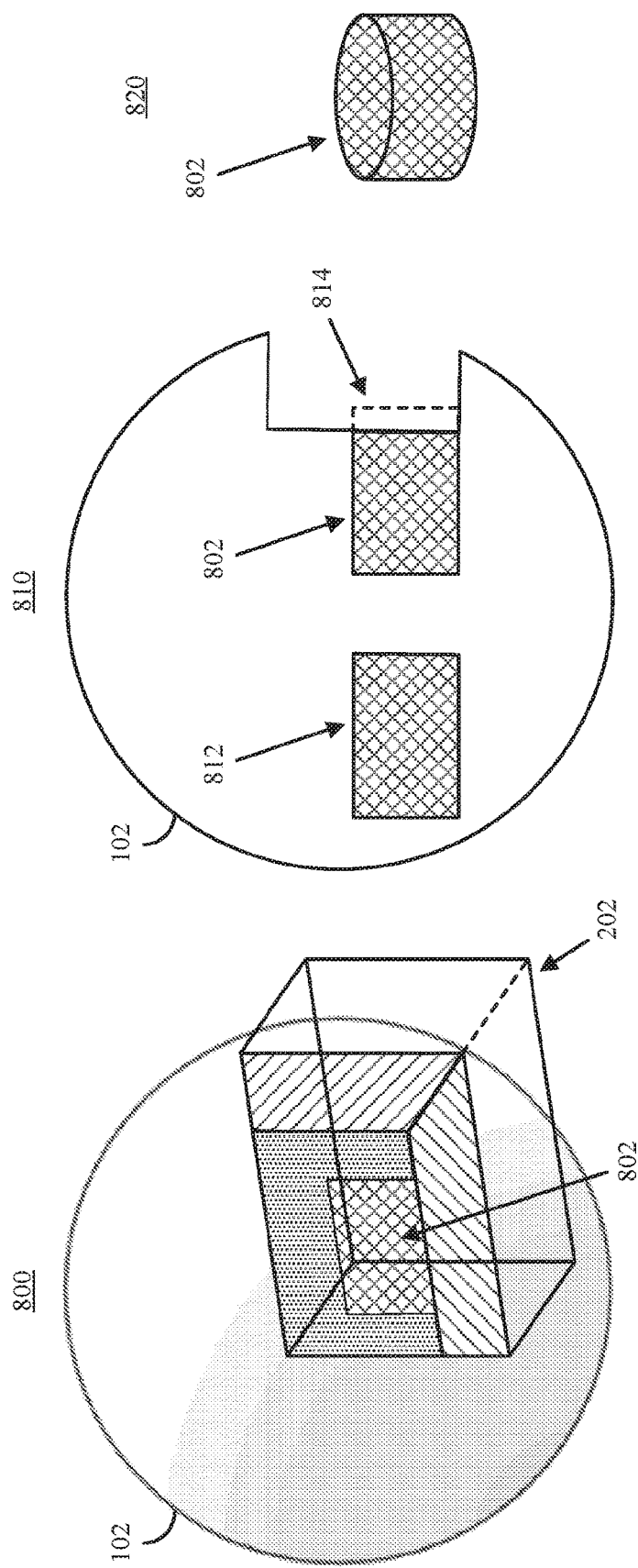
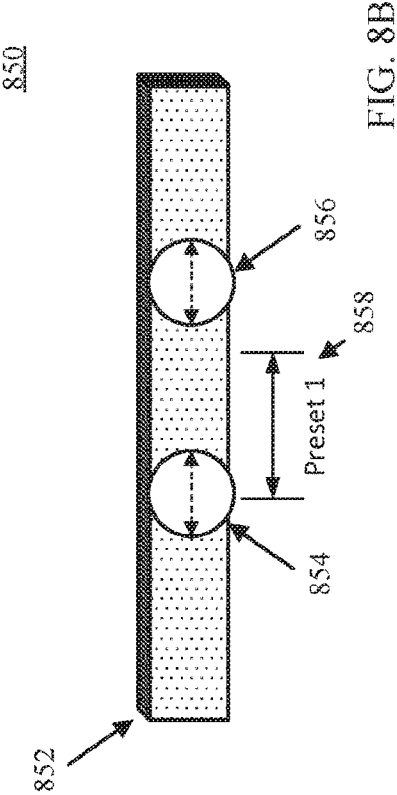
FIG. 8A1   FIG. 8A2   FIG. 8A3
FIG. 8B

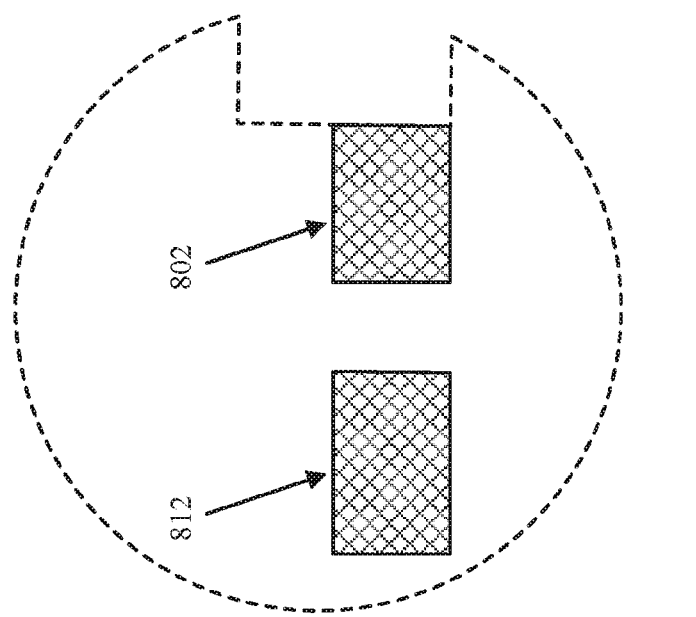
FIG. 8C2
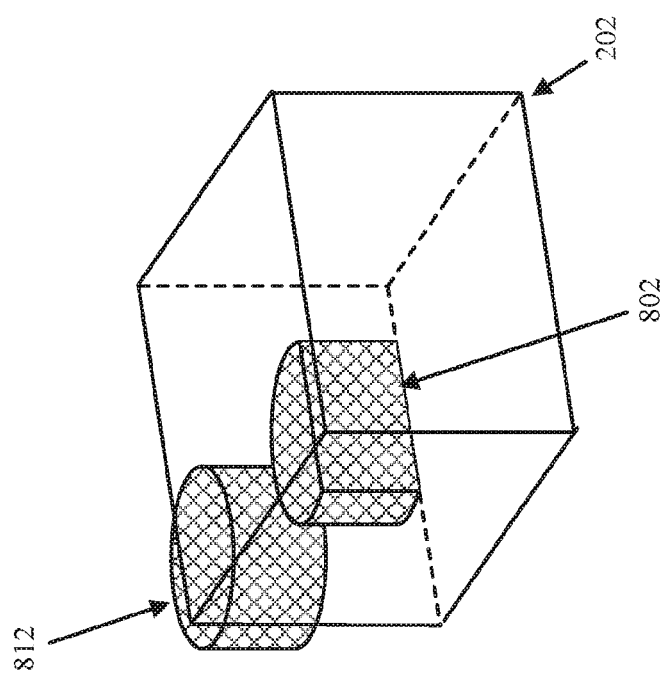
FIG. 8C1

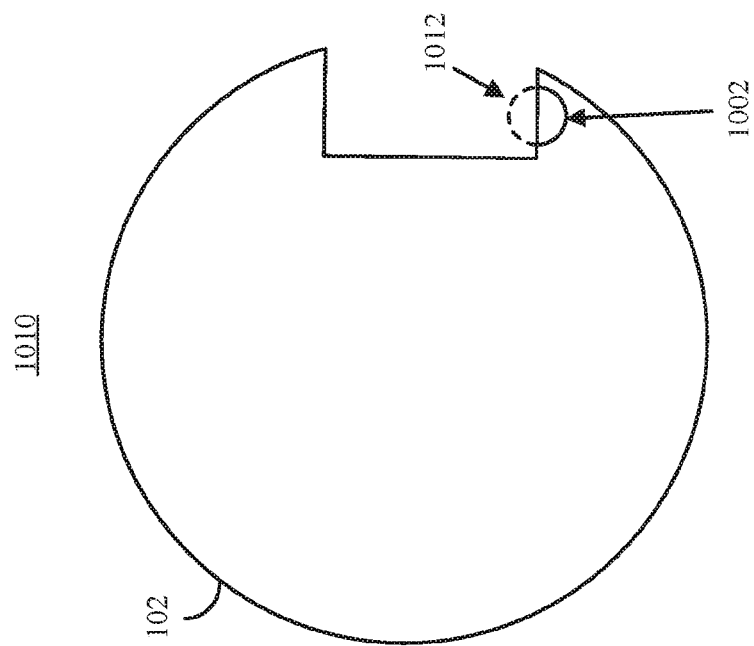
FIG. 10A2
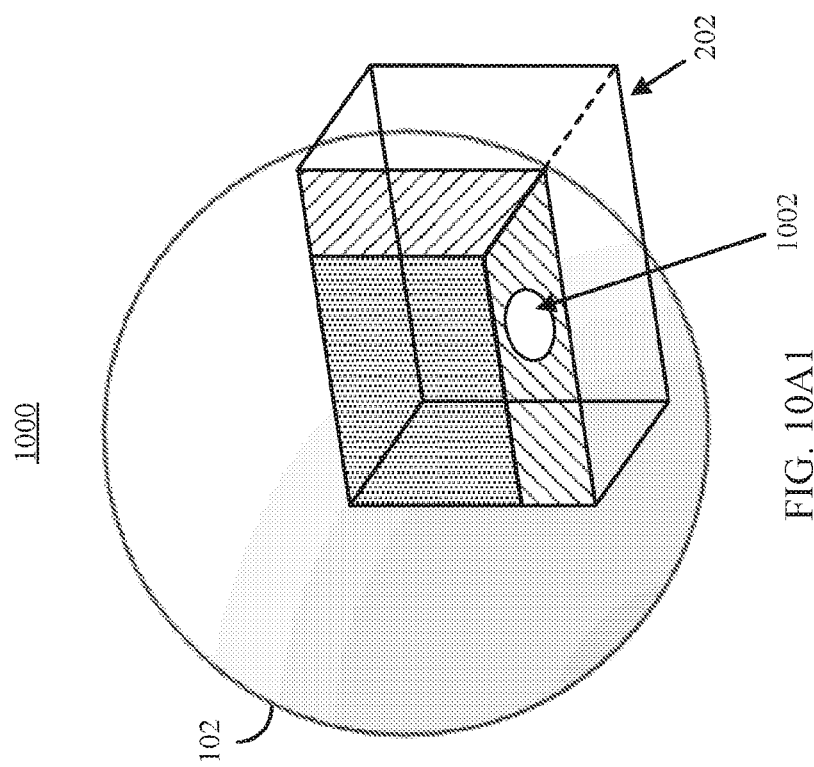
FIG. 10A1

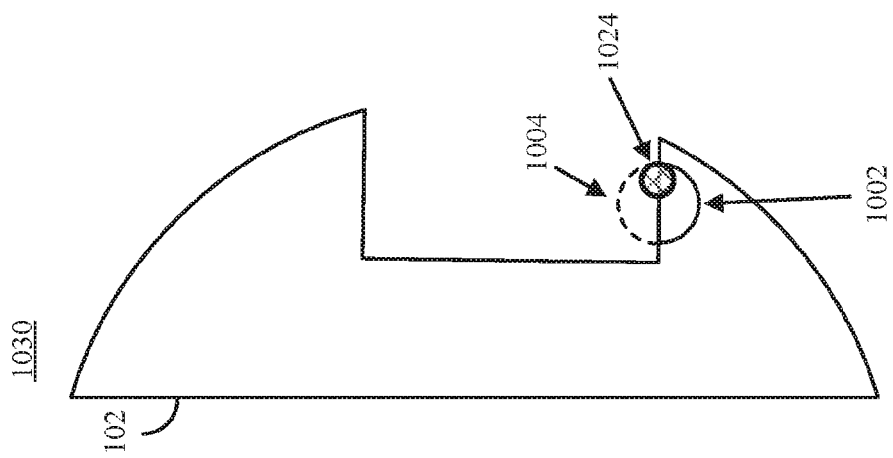
FIG. 10B2
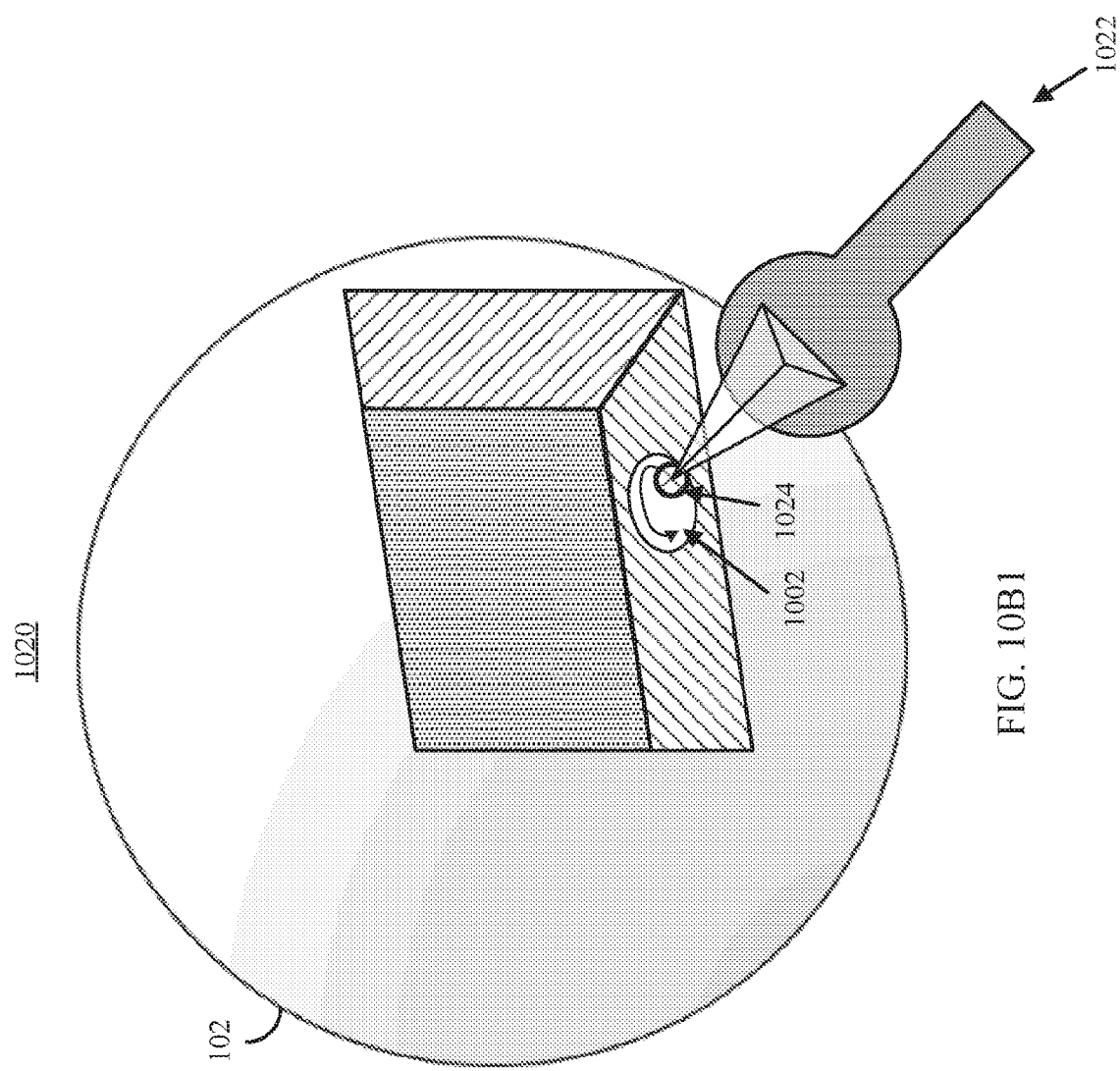
FIG. 10B1

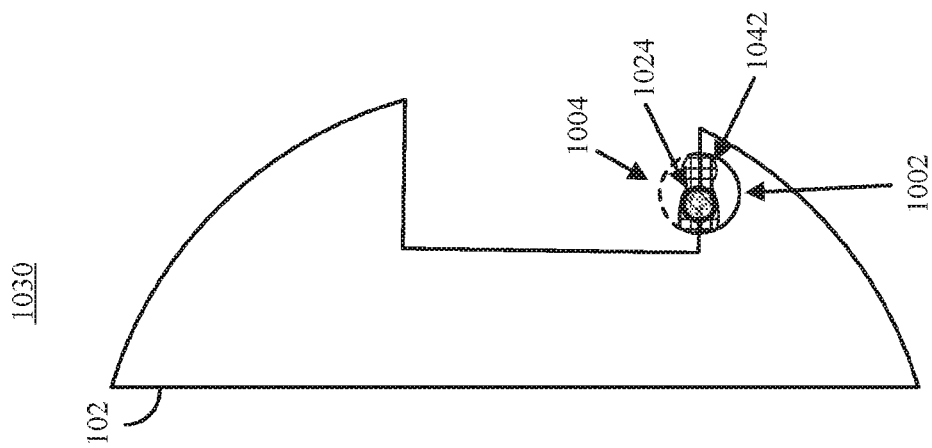
FIG. 10C2
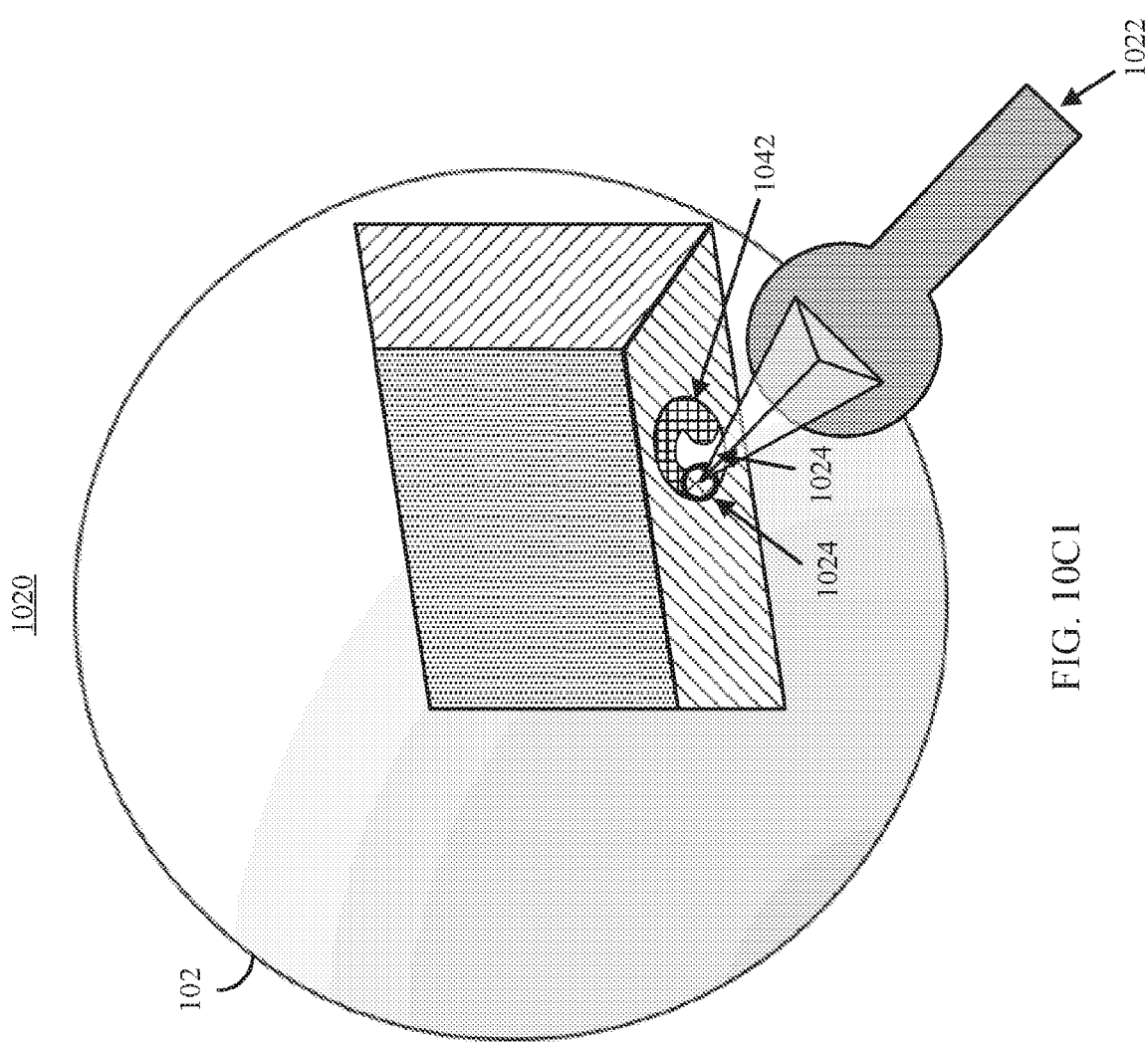
FIG. 10C1

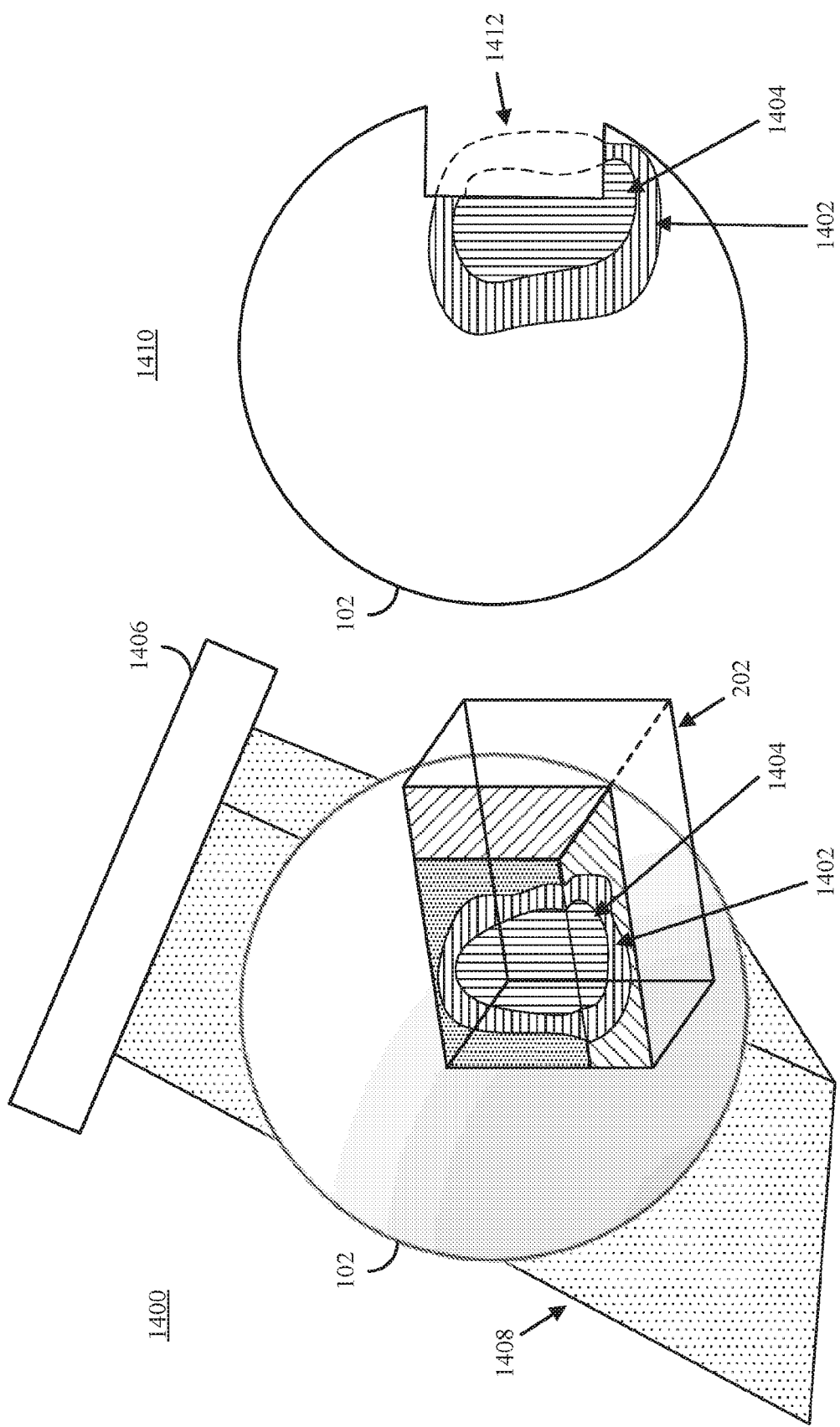
FIG. 14A2
FIG. 14A1

SYSTEMS, METHODS, AND MEDIA FOR PRESENTING MEDICAL IMAGING DATA IN AN INTERACTIVE VIRTUAL REALITY ENVIRONMENT

CROSS-REFERENCE TO RELATED APPLICATIONS

This application represents the U.S. National Stage Entry of International Application PCT/US2018/030311, filed Apr. 30, 2018, which is based on, claims the benefit of, and claims priority to U.S. Provisional Application No. 62/491,859, filed Apr. 28, 2017, which, Each of the preceding applications is hereby incorporated herein by reference in its entirety for all purposes.

STATEMENT REGARDING FEDERALLY SPONSORED RESEARCH

N/A

BACKGROUND

Conventional technologies for viewing volumetric medical imaging information (e.g., produced from an MRI or CT scan) generally limit a view to a 2D cross section along one of the primary planes of the subject's body (e.g., the axial, coronal, or sagittal plane). This can increase the mental load on a user (e.g., a radiologist) viewing the imaging data, as the user must construct a mental model of at least part of the anatomy shown in the imaging data. For example, in order to visualize the 3D extent of tumor, a user can flip between various 2D views to try to mentally reconstruct the 3D structure of an anatomical feature.

Accordingly, new systems, methods, and media for presenting medical imaging data in an interactive virtual reality environment are desirable.

SUMMARY

In accordance with some embodiments of the disclosed subject matter, systems, methods, and media for presenting medical imaging data in an interactive virtual reality environment are provided.

In accordance with some embodiments of the disclosed subject matter, a system for presenting medical imaging data in an interactive virtual reality environment is provided, the system comprising: a head mounted display (HMD) comprising: at least one display comprising a plurality of pixels; memory storing a three dimensional (3D) array of voxel values corresponding to a medical imaging scan of a subject, wherein the 3D array includes a plurality of internal voxels corresponding to interior anatomy of the subject and a plurality of external voxels corresponding to an exterior surface of the subject; and at least one hardware processor that is programmed to: determine a position of a first 3D object in a scene to be presented using the at least one display, wherein the first 3D object is a 3D representation of the subject based on the 3D array of voxel values; determine a position of a second 3D object comprising a surface in the scene to be rendered; determine, based on the position of the first object and the position of the second object, that the second 3D object overlaps at least a portion of the first 3D object; determine, for a first subset of pixels of the plurality of pixels, that the second 3D object is positioned between the pixel and the first 3D object; set a value for each of the first subset of pixels based on a value of an interior voxel at a position in the 3D array corresponding to the point at which the surface of the second 3D object and a ray cast from the pixel intersect without shading effects; determine, for a second subset of pixels of the plurality of pixels, that the second 3D object is not positioned between the pixel and the first 3D object; set a value for each of the second subset of pixels based on a value of an exterior voxel at a position in the 3D array corresponding to the point at which the surface of the first 3D object and a ray cast from the pixel intersect with at least one shading effect; and present, using the at least one display, an image of the scene, the first subset of pixels depicting an interior portion of the subject's anatomy without shading effects, and the second subset of pixels depicting the exterior surface of the subject.

In some embodiments, the at least one hardware processor is further programmed to: render a bounding box having dimensions that encompass the first 3D object; and determine a distance from each of the plurality of pixels to the front of the bounding box.

In some embodiments, the at least one hardware processor is further programmed to: generate, for each pixel of the second subset of pixels, a ray directed through the pixel toward the scene, and begin a ray marching operation from the front of the bounding box based on the distance from the pixel to the front of the bounding box; advance, for each of the plurality of pixels, the ray by a distance that is less than the diameter of a voxel in the 3D array of imaging data; and after advancing the ray, determine that the ray has satisfied a stopping condition.

In some embodiments, the at least one hardware processor is further programmed to: determine, after advancing the ray, that the ray position corresponds to a voxel in the 3D array of imaging data; in response to determining that the ray position corresponds to a voxel in the 3D array of imaging move the ray backward by a second distance that is less than the distance; determine, after moving the ray backward, that the ray position does not corresponds to a voxel in the 3D array of imaging data.

In some embodiments, the at least one hardware processor is further programmed to: determine a distance from each pixel of the first subset of pixels to the back of the second object; determine, for each pixel of the subset of pixels, that the distance to back of the second object is larger than the distance to the front of the bounding box; in response to determining, for each pixel of the subset of pixels, that the distance to back of the second object is larger than the distance to the front of the bounding box, generate a ray directed through the pixel toward the scene, and begin a ray marching operation from the back of the second object based on the distance from the pixel to the back of the second object.

In at least some embodiments, the at least one hardware processor is further programmed to: render distances to one or more surfaces of the second 3D object based on a mesh representation of the second 3D object; and store the distances to the one or more surfaces as a texture in a texture buffer associated with one or more of the at least one hardware processor.

In some embodiments, the at least one hardware processor is further programmed to: determine for each of a second plurality of pixels of the at least one display, that neither the first 3D object nor the second 3D object is positioned in a line of sight of the pixel; and in response to determining that neither the first 3D object nor the second 3D object is positioned in a line of sight of the pixel, set a value for the pixel based on a background image.

In some embodiments, the at least one hardware processor is further programmed to: subsequent to presenting the image of the scene, receive an instruction to inhibit voxels having intensity values outside of a range of intensity values from being presented; determine, for a third subset of pixels of the plurality of pixels, that the second 3D object is not positioned between the pixel and the first 3D object; generate, for each pixel of the third subset of pixels, a ray directed through the pixel toward the scene; advance, for each pixel of the third subset of pixels, the ray by a predetermined distance until the ray encounters a first voxel of the 3D array along the path of the ray; in response to encountering the first voxel, determine that an intensity value associated with the first voxel falls outside of the range of intensity values; in response to determining that a value associated with the first voxel falls outside of the range of intensity values, inhibit the voxel from being rendered; continue to advance the ray until a voxel associated with an intensity value within the range of intensity values; set a value for each of the third subset of pixels using at least one shading effect and based on the intensity value of the voxel associated with the intensity value within the range of intensity values at a position in the 3D array corresponding to the point at which the ray cast from the pixel intersects the voxel associated the intensity value within the range of intensity values; and present, using the at least one display, an image of the scene, the third subset of pixels depicting an interior portion of the subject's anatomy as a 3D surface with shading effects.

In some embodiments, the system further comprises a user input device, wherein the at least one hardware processor is further programmed to: receive interface to initiate a contouring operation; present a 3D user interface element in association with a virtual representation of the user input device; identify a plurality of voxels of the 3D array that are within a threshold distance of a center of the 3D user interface element; add one or more of the plurality of voxels within the threshold distance to a binary mask as voxels to be associated with a contour; and present, at the location of each voxel included in the binary mask, a particular color indicating that the voxel is associated with the contour.

In some embodiments, the at least one hardware processor is further programmed to: determine that the contouring operation is a 3D contouring operation; in response to determining that the contouring operation is a 3D contouring operation, add each of the plurality of pixels within the threshold distance to the binary mask.

In some embodiments, the at least one hardware processor is further programmed to: determine that the contouring operation is a 2D contouring operation; add voxels used to render the first 3D object in the image, including voxels corresponding to the first subset of pixels and the second subset of pixels, to a 2D mask; determine, for each of the plurality of voxels of the 3D array that are within the threshold distance of a center of the 3D user interface element, whether the voxel is included in the 2D mask; in response to determining that a particular voxel of the plurality of voxels is not included in the 2D mask, inhibit the voxel from being added to the binary mask; and in response to determining that a particular voxel of the plurality of voxels is included in the 2D mask, add the voxel to the binary mask.

In some embodiments, the at least one hardware processor is further programmed to: receive an instruction to inhibit voxels having intensity values outside of a range of intensity values from being presented; determine, for each of the plurality of voxels of the 3D array that are within the threshold distance of a center of the 3D user interface element, whether an intensity value of the voxel is within the range of intensity values; in response to determining that a particular voxel of the plurality of voxels has an intensity value that is not within the range of intensity values, inhibit the voxel from being added to the binary mask; and in response to determining that a particular voxel of the plurality of voxels has an intensity value that is within the range of intensity values, add the voxel to the binary mask.

In some embodiments, the at least one hardware processor is further programmed to: cause the user input device to provide haptic feedback based at least in part on an intensity value of one or more of the voxels of the plurality of voxels of the 3D array that are within the threshold distance of a center of the 3D user interface element.

In some embodiments, the at least one hardware processor is further programmed to: present, using the at least one display, a virtual surgical instrument; receive input to position the virtual surgical instrument to intersect at least a portion of the 3D array; and present an image that includes at least a portion of the virtual surgical instrument and at least a portion of interior voxels adjacent to the virtual surgical instrument.

In some embodiments, the at least one hardware processor is further programmed to: associate the virtual surgical instrument with the first 3D object; define a position of the virtual surgical instrument using relative coordinates based on a position of the first 3D object; and render the virtual surgical object in a position based on the relative coordinates and the position of the first 3D object in the scene.

In some embodiments, the at least one hardware processor is further programmed to: generate, based on a first radiation dose plan, a plurality of isodose contours that are each associated with a position within the first 3D object and a shape; present, using the at least one display, the plurality of isodose contours in association with the first 3D object; receive input to change the shape of a portion of a first isodose contour of the plurality of isodose contours to a new shape; calculate a second radiation dose plan based on the new shape of the first isodose contour; generate, based on the second radiation dose plan, a second plurality of isodose contours that are each associated with a position within the first 3D object and a shape; present, using the at least one display, the second plurality of isodose contours in association with the first 3D object.

In some embodiments, the at least one hardware processor is further programmed to present a virtual radiation source based on the first radiation dose plan in a configuration corresponding to a configuration that a radiation source providing a radiation treatment based on the first radiation dose plan will be instructed to achieve.

In some embodiments, the at least one hardware processor is further programmed to: receive a message indicating that a second HMD has initiated a collaborative session with the HMD; received information indicating locations and orientations of a plurality of objects, including the first 3D object and the second 3D object within a virtual reality environment being rendered by the second HMD; causing the first 3D object and the second 3D object to be positioned based on the received information to facilitate a shared experience with the second HMD.

In some embodiments, the at least one hardware processor comprises a graphics processing unit.

In some embodiments, the system further comprises a user input device comprising: a plurality of sensors; and at least one second hardware processor that is programmed to: receive outputs from each of the plurality of sensors; determine movements of the user input device along three orthogonal axes and rotations of the user input device around each of the three orthogonal axes; and send information to the HMD indicative of movements of the user input device; wherein the at least one hardware processor is further programmed to: receive the information indicative of movements of the user input device; and change a position of the second 3D object within the virtual reality environment based on the movements of the user interface indicated by the received information.

In accordance with some embodiments of the disclosed subject matter, a system for presenting medical imaging data in an interactive virtual reality environment is provided, comprising: memory storing volumetric medical imaging data of a patient organized into a three dimensional (3D) array of voxels, wherein the voxels including a plurality of internal voxels corresponding to interior anatomy of the patient and a plurality of external voxels corresponding to an exterior surface of the patient; and at least one hardware processor that is programmed to: cause a 3D model of the subject to be rendered based on the 3D array of voxels; cause a clip object having a regular geometric shape to be rendered; determine based on the rendering of the 3D model and the rendering of the clip object, locations at which a portion of the clip object overlaps the 3D model of the subject; cause a first portion of the 3D model that does not overlap the clip object, and that is in a line of sight of a virtual camera used to generate an image for presentation, to be rendered using one or more shading operations to determine intensity values to be used when displaying the first portion of the 3D model; cause portions of the 3D model that are within a volume defined by the clip object to be ignored; cause a second portions of the 3D model that is along a boundary between the clip object and the 3D model, and that is in a line of sight of the virtual camera, to be rendered using intensity values of the voxels corresponding to the second portion without adjusting the intensity via shading; and causing an image to be presented that includes the first portion of the 3D model with shading, and the second portion of the 3D model without shading.

BRIEF DESCRIPTION OF THE DRAWINGS

Various objects, features, and advantages of the disclosed subject matter can be more fully appreciated with reference to the following detailed description of the disclosed subject matter when considered in connection with the following drawings, in which like reference numerals identify like elements.

FIG. 1A shows an example 100 representing a portion of a virtual environment presenting a scene that includes a 3D model created from medical imaging data and a virtual camera representing a point of view of a user in accordance with some embodiments of the disclosed subject matter.

FIG. 1B shows a 2D view 120 of the scene represented in FIG. 1A illustrating various dimensions in accordance with some embodiments of the disclosed subject matter.

FIG. 2A shows an example 200 of a portion of a virtual environment presenting a scene that includes a 3D model created from medical imaging data, a clip object, and a virtual camera representing a point of view of a user in accordance with some embodiments of the disclosed subject matter.

FIG. 2B shows an example 220 of the scene represented in FIG. 2A with the clip object intersecting a portion of the 3D model in accordance with in accordance with some embodiments of the disclosed subject matter.

FIG. 8A1 shows an example 800 of a clip object intersecting a portion of a 3D model exposing medical imaging data at the boundary of the clip object including a portion of an anatomical structure having particular properties in accordance with some embodiments of the disclosed subject matter.

FIG. 8A2 shows an example 810 of a cross-section view of the object shown in FIG. 8A1 illustrating that there is a second anatomical structure within the 3D object that is not visible in FIG. 8A1 as no portion of the second anatomical structure intersects the boundary of the clip object in accordance with some embodiments of the disclosed subject matter.

FIG. 8A3 shows an example 820 of a 3D shape of the anatomical structure represented in FIGS. 8A1 and 8A2.

FIG. 8B shows an example of a user interface 850 that can be used to select portions of the medical imaging data to render and portions to medical imaging data to exclude from rendering in accordance with some embodiments of the disclosed subject matter.

FIG. 8C1 shows an example 860 of a clip object intersecting a portion of the 3D model shown in FIG. 8A1 with a filter applied that excludes medical imaging data other than medical imaging data having particular properties from being rendered exposing the two anatomical structures that are present within the 3D object but not rendered in accordance with some embodiments of the disclosed subject matter.

FIG. 8C2 shows an example 870 a cross-section view of the scene shown in FIG. 8C1 illustrating with a dotted line the extent of the 3D model that is being excluded from rendering based on the filter that has been applied in accordance with some embodiments of the disclosed subject matter.

FIG. 10A1 shows an example 1000 of a clip object intersecting a portion of a 3D model exposing medical imaging data at the boundary of the clip object including a portion of an anatomical structure of interest to be segmented in accordance with some embodiments of the disclosed subject matter.

FIG. 10A2 shows an example 1010 of a cross-section view of the object shown in FIG. 10A1 illustrating that, although a 2D cross section of the anatomical structure of interest is shown in FIG. 10A1 at the boundary of the clip object, the full three dimensional extent of the anatomical structure of interest is represented in the medical imaging data that is not rendered in the example shown in FIG. 10A1 in accordance with some embodiments of the disclosed subject matter.

FIG. 10B1 shows an example 1020 of a user interface element representing a user input device that can be used to select portions of the medical imaging data to be segment with a 3D virtual brush presented in a defined position with respect to the user interface element in accordance with some embodiments of the disclosed subject matter.

FIG. 10B2 shows an example 1030 of a cross-section view of a portion of the object shown in FIG. 10B1 illustrating that the 3D brush can extend past the portion of the medical imaging data being rendered in accordance with some embodiments of the disclosed subject matter.

FIG. 10C1 shows an example 1040 of the object shown in FIG. 10A1 with a portion of the anatomical structure of interest segmented in response to movements of the 3D brush in relation to the 3D model in accordance with some embodiments of the disclosed subject matter.

FIG. 10C2 shows an example 1050 of a cross-section view of a portion of the object shown in FIG. 10C1 illustrating that the portions of the medical imaging data that are segmented can extend past the portion of the data being rendered in accordance with some embodiments of the disclosed subject matter.

FIG. 14A1 shows an example 1400 of a clip object intersecting a portion of a 3D model exposing medical imaging data at the boundary of the clip object and isodose contours showing the expected amount of radiation different portions of the subject's anatomy would be exposed to based on a particular radiation does plan in accordance with some embodiments of the disclosed subject matter.

FIG. 14A2 shows an example 1410 of a cross-section view of the object shown in FIG. 14A1 illustrating that, although 2D cross sections of the isodose contours are shown in FIG. 14A1 at the boundary of the clip object, the full three dimensional extent of the isodose contours can be calculated for portions of the medical imaging data not currently rendered in the example shown in FIG. 14A1 in accordance with some embodiments of the disclosed subject matter.

DETAILED DESCRIPTION

Figure 2C:
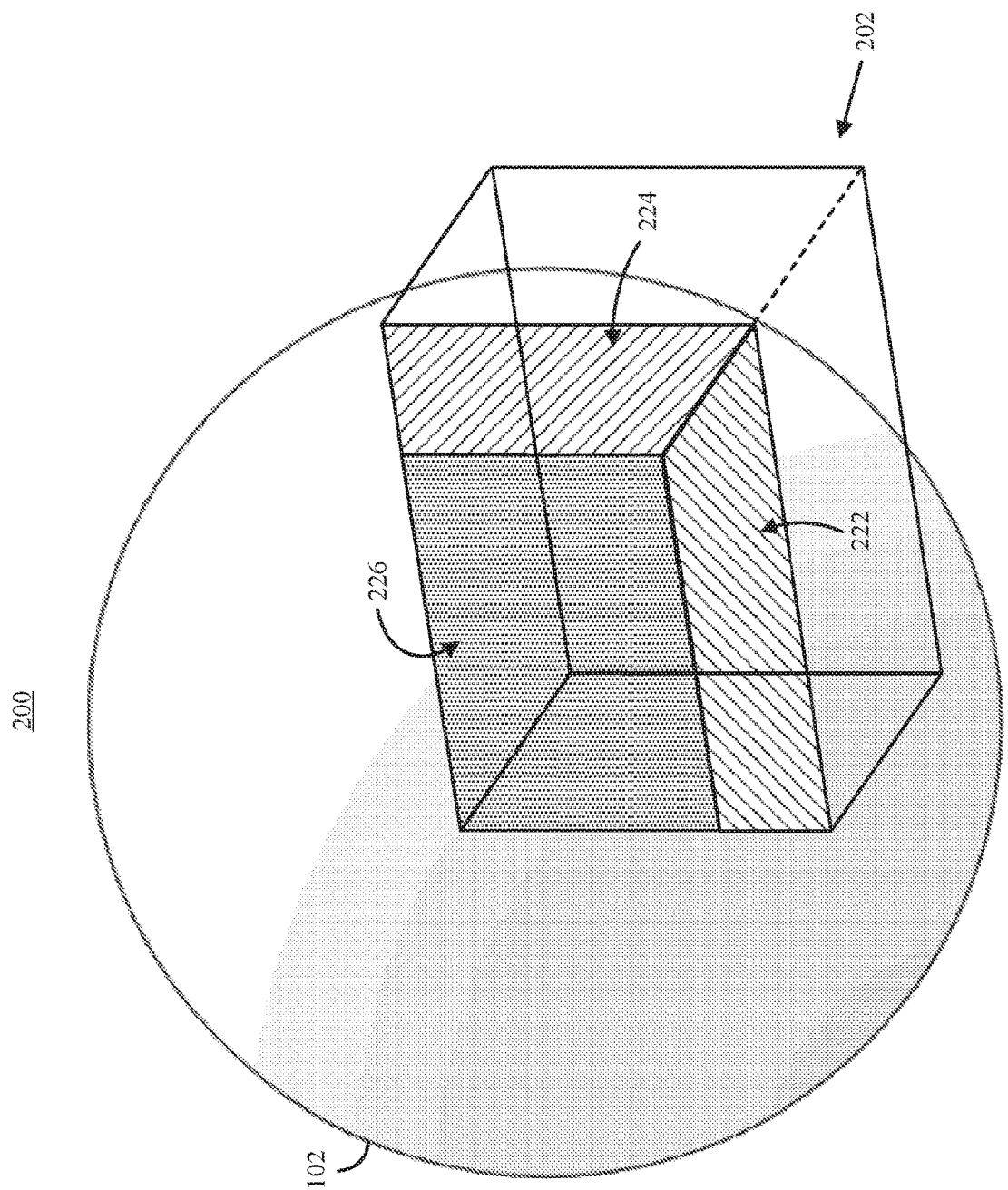
FIG. 2C shows an example 230 of an enlarged view of the 3D model and clip object represented in FIG. 2B in accordance with some embodiments of the disclosed subject matter.

Before any embodiments of the disclosed subject matter are explained in detail, it is to be understood that the disclosed subject matter is not limited in its application to the details of construction and the arrangement of components set forth in the following description or illustrated in the following drawings. The disclosed subject matter is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the disclosed subject matter. Various modifications to the illustrated embodiments will be readily apparent to those skilled in the art, and the generic principles herein can be applied to other embodiments and applications without departing from embodiments of the disclosed subject matter. Thus, embodiments of the disclosed subject matter are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the disclosed subject matter. Skilled artisans will recognize the examples provided herein have many useful alternatives and fall within the scope of embodiments of the disclosed subject matter.

In accordance with some embodiments of the disclosed subject matter, mechanisms (which can include systems, methods and/or media) for presenting medical imaging data in an interactive virtual reality environment are provided. In some embodiments, one or more portions of a subject's anatomy can be imaged using a volumetric medical imaging technique, such as magnetic resonance imaging (MRI), ultrasound, or computed tomography (CT), that captures data corresponding to a subject's anatomy in three dimensions, often organized as a series of two-dimensional cross-sectional "slices." Volumetric medical imaging data represented by a series of two-dimensional (2D) medical images are often stored in a standardized format, such as the Digital Imaging and Communications in Medicine (DICOM) standard format. In some embodiments, the two-dimensional image data can be used to create a three-dimensional (3D) model of the subject's anatomy by organizing the series of 2D images as a 3D image array. For example, a 2D medical image can be represented using a two dimensional array where each element in the array corresponds to a pixel, and can be addressed by two coordinates (e.g., X and Y). In such an example, each pixel can be associated with one or more values that are indicative of the anatomy corresponding to that pixel, such as an intensity value (e.g., for a monochrome image), a Hounsfield unit, values for parameters corresponding to that portion of the subject's anatomy, one or more color values (e.g., representing a segmentation or contouring), etc. In some embodiments, individual 2D medical images can be converted into a 3D array by adding a value for depth (e.g., Z) to each pixel, which in a 3D array can be referred to as a voxel. Note that, in some cases, the X and Y coordinates may need to be adjusted for individual images to ensure that the image is properly aligned with neighboring images (e.g., due to movement during scanning causing an offset between two images).

In accordance with some embodiments, the values in the 3D array can be used to render and display a 3D model of the subject's anatomy represented by the volumetric medical imaging data using a display device, and can be manipulated using one or more user input devices. For example, the 3D model can be presented using a head mounted display (HMD), such as a virtual reality display or augmented reality display. As another example, the orientation, size, position, etc., of the 3D model can be adjusted using one or more user input devices, such as a handheld control device that is tracked along six degrees of freedom (DOF), such as a VIVE controller available from HTC (headquartered in New Taipei City, Taiwan). In such an example, movements of the controller in physical space can be replicated in a virtual space, which can facilitate interaction with objects in a virtual (and/or augmented) reality environment.

In some embodiments, interior portions of the 3D model can be exposed by placing a "clip object" within the scene that intersects with the 3D model. Such a clip object can have any suitable shape (e.g., a cube, a pyramid, a sphere, an oblate spheroid, a 2D plane, etc.) and any suitable size, which can be adjustable. In some embodiments, voxels of the 3D model that represent the "outside" of the model (e.g., the exterior contours of a subject's body for a thoracic CT scan, the exterior surface of a subject's skull for a head CT scan, etc.) can be rendered as though it is a virtual object. For example, each exterior voxel can be rendered based on the orientation of the model, the intensity and/or location of a light source(s) in the scene, etc. In a more particular example, the value to render for each pixel can be calculated using real-time volumetric raymarching to determine a value for each pixel to be presented by the display device (e.g., stereoscopic raymarching for many HMDs that present images to each of a user's eyes to create a 3D effect). As another example, one or more real-time ray casting techniques (e.g., recursive ray tracing techniques) can be used to determine the color and/or brightness for each pixel by casting rays at points in the scene, and when a ray intersects an object, creating secondary rays (e.g., shadow rays), tertiary rays (e.g., transmitted and/or refracted rays), etc., for each pixel, and combining the effects of these rays to determine how to render points on the model. In some embodiments, a graphics processing unit (GPU) can be used to implement one or more real-time rendering techniques used to determine how to render exterior points of the model.

In some embodiments, imaging data that is internal to the surface of the 3D model (e.g., representing internal anatomy) can be presented based on the position, orientation, and/or shape of one or more clip objects that are intersection the 3D model. In some such embodiments, portions of the 3D model along the boundary of the clip object can be rendered based on the value of the underlying medical imaging data without taking into account lighting, orientation, etc., of the 3D model (e.g., without performing any shading operations).

In some embodiments, one or more surfaces of the clip object can be pre-rendered each frame, and this surface can be used to calculate raymarching starting and ending positions for rays intersecting the clip object. In some such embodiments, as a user manipulates the position, orientation, and/or size of the clip object, the portions of the volumetric medical imaging data that are presented can be changed in real-time.

In some embodiments, a user can manipulate the 3D model to reorient the model, increase or decrease the size of the model, etc., using one or more user input devices. For example, a user can use one or more user input devices that sense changes in orientation for 6 DOF to change the orientation of the 3D model by translation along one or more longitudinal axes (e.g., the X, Y, and/or Z axes), by rotation around one or more longitudinal axes (e.g., changing the pitch, yaw, and/or roll). In a more particular example, a user can provide an input (e.g., by depressing a trigger button on the input device) indicating that the user wishes to manipulate the orientation of the 3D model, and the mechanisms described herein can change the orientation of the 3D model based on the change in orientation of the user input device(s).

As another example, a user can use one or more user input devices to change the size at which the 3D model is presented by expanding or contracting the 3D model. In a more particular example, a user can provide an input (e.g., by depressing a trigger button on a pair of input devices) indicating that the user wishes to manipulate the size at which the 3D model is presented, and the mechanisms described herein can change the size at which the 3D model is rendered based on the movement(s) of the input device(s). In such an example, in response to a pair of input devices moving closer together, the mechanisms described herein can contract the 3D model to a smaller size, and in response to the pair of input devices moving farther apart the mechanisms described herein can expand the 3D model to a larger size.

As yet another example, the mechanisms described herein can sense movements of the HMD and/or user through space, and change the orientation and/or size at which the 3D model is presented based on movements of the HMD and/or user.

As described above, conventional medical imaging presentation techniques often allow views along only the transverse, sagittal, and/or coronal planes (based on the direction of the scanner and/or the subject being scanned), and this can cause a user to have to rely on a mental model constructed based on moving between multiple adjacent images. In some embodiments, the mechanisms described herein can facilitate viewing portions of a 3D volumetric medical imaging scan along arbitrary directions having arbitrary shapes. For example, a user can manipulate the orientation of a cuboid clip object to intersect the 3D model at an angle to each of the transverse, sagittal, and coronal planes, facilitating viewing of portions of the scan that do not neatly align with any of these planes. Additionally, in such an example, the faces of the clip object can facilitate viewing multiple different planes simultaneously (e.g., as described below in connection with FIGS. 2A-2D). As another example, a user can manipulate the orientation of a clip object with one or more curved surfaces to generate a curved view of the 3D volumetric medical imaging scan. In some embodiments, by facilitating viewing a 3D volumetric medical imaging scan along arbitrary surfaces, the mechanisms described herein can allow a user to gain additional clinical insight beyond what they could obtain using a conventional imaging system that forces the user to rely on a mental model to visualize anatomy that does not align with the transverse, sagittal, and/or coronal planes, which is necessarily less reliable and less detailed than being able to visually inspect the 3D model along an arbitrary surface.

In some embodiments, the mechanisms described herein can facilitate contouring (sometimes also referred to as segmentation) and/or measurement of features included in the 3D volumetric medical imaging data. For example, in some embodiments, a user can manipulate the orientation of the 3D model and/or a clip object intersecting the 3D model to expose a portion of anatomy that the user wishes to segment and/or measure. In such an example, user input received via one or more user input devices(s) can be used to designate portions of the medical imaging data to segment and/or measure.

In some embodiments, the GPU can render the three dimensional location of both the external surface and the clip objects surfaces that intersect the object into a texture buffer. The mechanisms described herein can track a location of a virtual user interface element (sometimes referred to herein as a brush), and the intersection of the three dimensional locations in the texture buffer with the user-manipulated brush can be determined and used to delineation an intended region of the scan to segment and/or measure. In some embodiments, the mechanisms described herein can take into account threshold filter (e.g., as described below in connection with FIGS. 7, and 8A1-8E) that facilitates isolation of one or more types of tissue and/or material (e.g., bone, blood vessels, etc.), by segmenting only portions of the scan that are also not being filtered out.

In some embodiments, the mechanisms described herein can provide haptic feedback (e.g., vibrational feedback) and/or other feedback to indicate properties of a region that a user is currently demarcating. For example, the mechanisms described herein can provide different amounts of haptic feedback based on the intensity and/or Hounsfield unit value of the voxel closest to the center of the brush head (e.g., as intensity increases haptic feedback can increase, as intensity increases haptic feedback can decrease, as intensity moves away from the average intensity being presented haptic feedback can increase, etc.). As another example, the mechanisms described herein can provide different amounts of haptic feedback based on the average intensity and/or Hounsfield unit values of the voxels within the brush head. As yet another example, the mechanisms described herein can provide haptic feedback based on how close an edge of the brush is to a boundary between areas with substantially (e.g., greater than a threshold) different average intensity and/or Hounsfield unit values.

In some embodiments, through the use of clip objects, virtual brushes, and/or haptic feedback, the mechanisms described herein can facilitate contour delineation in three dimensions, allowing a user to draw on an arbitrary non-planar three-dimensional surface, which may result in more accurate and/or more efficient (e.g., faster) delineation of complex anatomic regions in a manner that would not be possible using conventional techniques.

In some embodiments, the mechanisms described herein can facilitate planning and/or optimization of radiation therapy treatments in three dimensions. Conventional techniques for generating radiation therapy treatment plans generally rely on defining a beam direction and/or arc of gantry rotation for which dose is to be calculated via radiation transport simulation. Additionally, in some conventional techniques, the apertures are inversely optimized to achieve dose metrics. However, these techniques are limited in various ways, for example, by restricting the arc trajectories to a set of standard trajectories, and provide relatively crude controls for adjusting the plan. In some embodiments, the mechanisms described herein can facilitate definition of non-standard arc trajectories via manipulation of a virtual gantry, and can facilitate intuitive adjustment of dose plans through three dimensional manipulation of the contours of isodose curves/surfaces.

In some embodiments, the mechanisms described herein can render a three-dimensional model of a linear accelerator and/or radiation beam direction that can be moved and manipulated with six degrees of freedom around a 3D model based on a volumetric medical imaging scan of a portion of a subject's anatomy that is to be the target area for radiation therapy. In some embodiments, the mechanisms described herein can render the 3D model of the subject's anatomy, potentially in combination with a clip object (e.g., as described above) to show details of the underlying medical imaging data. In some such embodiments, the mechanisms described herein can receive user input (e.g., via a 6 DOF user input device) to manipulate the beam direction relative to the visualized anatomy, which can facilitate definition of a trajectory that uses multiple axis motions simultaneously. In some embodiments, the mechanisms described herein can allow a user to visually verify whether the trajectory defined by the user would be likely to cause any collisions (e.g., between the gantry and the subject, immobilization devices, and/or table).

In some embodiments, the mechanisms described herein can render a three-dimensional dose distribution overlaid on volumetric medical imaging data, which can be manipulated via user input devices (e.g., hand held controllers) and/or hand tracking. For example, in some such embodiments, a user can use the input device(s) and/or hand gestures to manipulate (e.g., by "pushing," "pulling," "stretching," and/or "compress") one or more portions of the dose distribution to cause it to conform to a desired shape. The change to the dose distribution can cause constraints in an inverse optimizer to be updated, which can then re-calculate an optimized dose distribution in response to the user's 3D manipulations. An updated dose distribution can then be presented taking into account the change made by the user, which can allow the user to view other changes that are being caused by the changes the user is making to the dose distribution. Additionally, in some embodiments, the mechanisms described herein can provide haptic feedback based on changes in the optimizer objective function. In some embodiments, the mechanisms described herein can facilitate intuitive manipulate of a radiation therapy plan in a manner that is not possible with conventional radiation planning techniques, and can accordingly facilitate more plans that are more customized to a particular subject's anatomy.

In some embodiments, the mechanisms described herein can facilitate planning for surgical interventions and other interventional procedures by allowing a user to manipulate virtual objects (e.g., surgical instruments) in a virtual environment and receive feedback (e.g., visual and/or haptic feedback) about how the virtual object is likely to interact with a subjects anatomy based on a particular plan. For example, the mechanisms described herein can render a virtual biopsy needle, which the user can manipulate to plan a path for a percutaneous lung biopsy. In such an example, the area to be biopsied (e.g., a lung lesion) can be highlighted using contouring/segmenting techniques described above (and below in connection with FIGS. 9 and 10A1-10E), and the user can position the virtual biopsy needle such that the distal end intersects the area to be biopsied. Additionally, in some embodiments, areas to avoid (e.g., because they are more likely to be the cause of complications if punctured with a biopsy needle) can be highlighted using contouring/segmenting techniques described herein.

In some embodiments, a user can evaluate various pathways for performing a biopsy in a virtual environment based on the subject's actual anatomy for various factors, such as the likely diagnostic yield, the risk of complications, etc. For example, a user can attempt various pathways for performing a percutaneous biopsy of lung lesions to find a pathway that the user believes provides relatively large diagnostic yield with relatively low risk of complications. Because the best approach (e.g., as determined by the user) may be non-coplanar with any of the axial, sagittal, and coronal planes, conventional medical imaging techniques that only allow viewing along these planes may not allow the user to discover a path that can be discovered in a virtual environment. In some embodiments, the mechanisms described herein can facilitate viewing of the tract through which a surgical tool passes through the subject's anatomy, for example, through use of a clip object.

In some embodiments, the mechanisms described herein can provide haptic feedback based on the location of the interventional planning object with respect to the 3D image data. For example, the mechanisms described herein can provide feedback based on the intensity and/or Hounsfield value at the tip of a virtual biopsy needle to provide feedback on the type of tissue that the virtual biopsy needle is passing though. In such an example, intensity of the haptic feedback can increase with intensity, decrease with intensity, and/or increase when passing through (or near/within a threshold distance) an intensity and/or Hounsfield value corresponding to a particular type of tissue, such as bone, blood vessels, etc.

In some embodiments, the mechanisms described herein can be used to mark planned locations of incisions, anastomoses, and/or other surgical hardware using contouring tools. This can allow a surgical teams to plan operative approaches and through either real time transfer of the plan and/or saving the plan, can apply the plan during a surgical intervention. Additionally, such surgical planning can facilitate communication of a planned surgical approach to other providers on the surgical (and/or treatment) team, which may allow other providers to plan other procedures (e.g., radiation treatments) based on the planned surgical approach. For example, a radiation oncologist may be interested in the operative approach that will be taken by a surgeon when resecting a tumor in order to deliver effective neoadjuvant (i.e., preoperative) radiation to ensure adequate coverage of the tumor while sparing adjacent tissues which may be desirable for operative reconstruction after resection of the tumor. In such an example, as described above, the radiation oncologist can, for example, plan a radiation therapy using a 3D model of the subject's anatomy with the tumor, approach, and/or tissue to be to avoided segmented to allow the radiation oncologist to visually verify the likely dose/damage that the tissue to be used for reconstructive surgery is likely to be exposed to.

In some embodiments, the location of planning objects and/or segmentations can be related to a 3D model, rather than defining the location of such objects using absolute coordinates. For example, the coordinates and orientation of a biopsy needle can be defined using coordinates that indicate the location and orientation of the biopsy needle using the 3D model as the frame of reference (e.g., the center of the model can be defined as the origin for the biopsy needle). This can cause the orientation of the planning object and/or segmentations to change as the orientation of the 3D model due to the coordinates used to render such objects are defined based on the coordinates and orientation of the 3D model to which it is related.

In some embodiments, the mechanisms described herein can isolate and/or remove portions of the 3D model corresponding to particular portions of anatomy. For example, as described below in connection with FIGS. 7-8E, one or more ranges of intensity values or Hounsfield values can be selected to be included and/or excluded when rendering the 3D model. In a more particular example, on a CT scan areas of bone may have a distinct intensity or Hounsfield value, and the mechanisms described herein can receive a request (e.g., via a user interface) to include only voxels having an intensity within a certain range generally corresponding to bone. The mechanisms described herein can then ignore any voxels having an intensity value falling outside of this range, and render only portions of the 3D model with intensity values within the range.

Figure 8D:
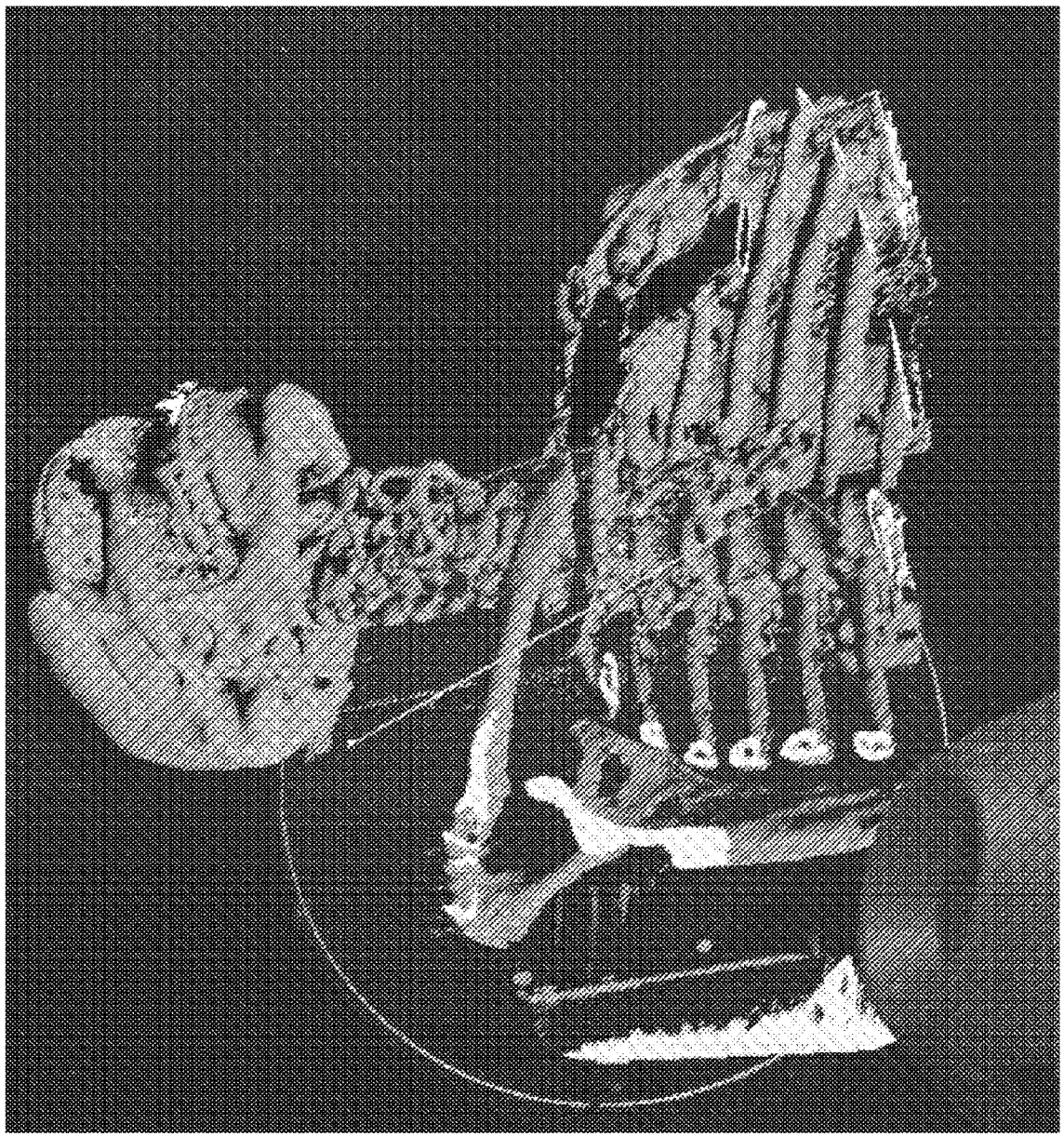
FIG. 8D shows an example of a portion of a 3D model based on a computed tomography scan in which a filter has been applied to exclude portions of the medical imaging data except portions of the data having properties representing bone presented within a virtual environment using a system configured in accordance with some embodiments of the disclosed subject matter.
Figure 8E:
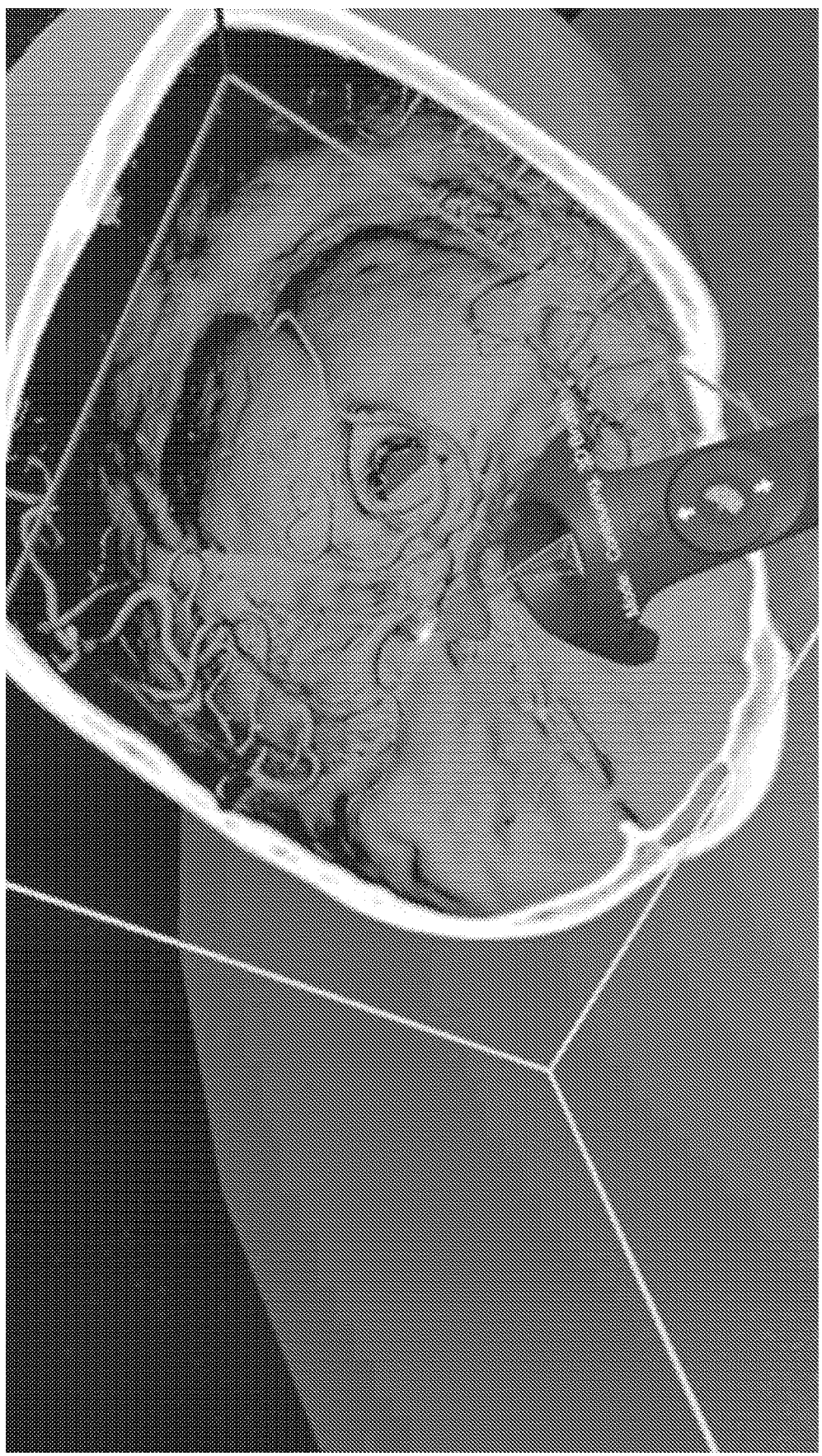
FIG. 8E shows an example of a portion of a 3D model based on a computed tomography scan in which a filter has been applied to exclude portions of the medical imaging data except areas having properties representing blood vessels presented within a virtual environment using a system configured in accordance with some embodiments of the disclosed subject matter.

In some embodiments, the mechanisms described herein can determine the intensity and/or Hounsfield value of a voxel when a ray encounters the voxel, and can determine that there is not an intersection if the value is not within a range that is to be rendered. Such filtering techniques can facilitate presentation of particular portions of the 3D model without the need to manually segment the medical imaging data, for example to present a skeletal renderer from a CT scan (e.g., as shown in FIG. 8D) or to highlight blood vessels in a contrast-enhanced T1 MRI brain scan or CT scan (e.g., as shown in FIG. 8E). In some embodiments, filtering of the medical imaging data to present particular types of anatomy (and exclude other types of anatomy) can be used with other mechanisms described herein, such as using clip objects to view a cross section of the medical imaging data, drawing contours on and/or segmenting the medical imaging data, planning radiation treatments and/or other interventions (such as percutaneous biopsy), etc. For example, because the mechanisms described herein allow a user to specify filtering parameters in real time, a user can insert a virtual biopsy needle using a view of the 3D model that excludes voxels not corresponding to bone (i.e., a skeletal representation) to avoid any bones that are present, and can remove the filtering to view soft tissue through which the biopsy needle passes using a clip object.

Although the mechanisms described herein are generally described in connection with presentation in a fully virtual environment presented via an HMD, this is merely an example, and the mechanisms described herein can be used to present content using other techniques, such as using a partially virtual environment (e.g., using an augmented reality display), on a 3D display (e.g., a 3D monitor), using a non-3D display to render the 3D content, etc.

FIG. 1A shows an example 100 representing a portion of a virtual environment presenting a scene that includes a 3D model created from medical imaging data and a virtual camera representing a point of view of a user in accordance with some embodiments of the disclosed subject matter. As shown in FIG. 1A, the mechanisms described herein can render a 3D model of an object 102 (note that object 102 is presented as a sphere to illustrate concepts associated with the mechanisms described herein without overcomplicating the drawings) within virtual environment 100. The 3D model of object 102 can be generated from volumetric medical imaging data of object 102 by organizing many 2D images (e.g., "slices") captured by a medical imaging device (e.g., a CT or MRI device) into a 3D array. Note that the slices that form object 102 can be oriented in any direction with respect to virtual camera 104. In some embodiments, the mechanisms can use a virtual camera 104 representing a viewpoint from which virtual environment 100 is to be presented on a display (e.g., a single display of a stereoscopic pair of displays within an HMD). In some embodiments, an array of pixels 106 shown in FIG. 1A represents pixels of the display on which virtual environment 100 is to be presented. During operation, the mechanisms described herein can determine, for each pixel in array 106, a brightness value and color values to use when displaying object 102. In some embodiments, the mechanisms described herein can use one or more ray techniques to determine values for each pixel in array 106. For example, the mechanisms described herein can cast a ray 108 (or multiple rays) through a particular pixel 110 and determine whether the ray intersects object 102 (or any other object).

In some embodiments, the mechanisms described herein can use raymarching techniques to determine a point (or points) at which a particular ray intersects an object. For example, as described below in connection with FIG. 3, a ray (e.g., ray 108) can be advanced through virtual environment by an incremental distance, and after advancing ray 108 the mechanisms can determine whether the ray intercepted one or more of voxels of an object to be rendered. In some embodiments, as described below in connection with FIG. 6, the mechanisms described herein can render a bounding box 112 delineating the maximum extent of object 102 (e.g., the depth, height, and width of the object). In some such embodiments, the length of a first step for ray 108 can be the distance to a face of bounding box 112, which may or may not be aligned with the angle of the viewport (e.g., the orientation of the bounding box can be locked to the object). For example, FIG. 1B shows a 2D view 120 of the scene represented in FIG. 1A illustrating various dimensions in accordance with some embodiments of the disclosed subject matter. As shown in FIG. 1B, the distance between the imaging plane of virtual camera 104 and the closest point of object 102 is identified as $D_f$. In some embodiments, the distance of a first step for each ray can be distance $D_f$ as there can be no objects closer to virtual camera 104 than the front of bonding box 112. In some embodiments, if there are multiple objects being rendered that are each associated with a bounding box, the ray can be advanced by the distance to the closest bounding box, and if the ray does not intersect the closest bounding box (e.g., at the distance to the closest bounding box, the lateral coordinates of the ray do not coincide with the bounding box), the ray can be advanced by the distance to the next closest bounding box, etc., until the ray intersects a bounding box, or does not intersect the farthest bounding box (and therefore does not intersect an object in the scene). In some embodiments, when the point at which the ray intersects the object is determined, the mechanisms described herein can calculate an intensity values and/or color value for the pixel based on the texture (if any) corresponding to that point, the location and intensity of one or more light sources, the transparency of the voxel (or voxels) which the ray intersects, etc.

FIG. 2A shows an example 200 of a portion of a virtual environment presenting a scene that includes a 3D model created from medical imaging data, a clip object, and a virtual camera representing a point of view of a user in accordance with some embodiments of the disclosed subject matter. As shown in FIG. 2A, a movable clip object 202 can be rendered in virtual environment 202. In some embodiments, edges of clip object 202 can be visibly rendered (e.g., as shown in FIG. 2D), while boundaries of clip object 202 (e.g., faces of clip object 202) can be transparent (i.e., not visible) or presented as semi-transparent. As shown in FIG. 2A, clip object 202 can be moved relative to object 102 (e.g., as shown by arrow 204).

FIG. 2B shows an example 210 of the scene represented in FIG. 2A with clip object 202 intersecting a portion of the 3D model in accordance with some embodiments of the disclosed subject matter. As shown in FIG. 2B, when clip object 202 intersects with object 102, areas of object 102 that are at the boundary of clip object 202 can be rendered differently than areas of object 102 that are not at the boundary of clip object 202. In some embodiments, when a ray corresponding to a particular pixel intersects object 102 at a boundary of clip object 202, the mechanisms described herein can determine the intensity value and/or color values for that pixel from the underlying medical imaging data (which may be an interpolated value). For example, the intensity value and/or color values for a pixel depicting a point that lies at the boundary of clip object 202 within object 102 can be determined by looking up the intensity value(s) in the 3D array for that point, and rendering the pixel using that intensity value(s). This can cause portions of object 102 that intersect with clip object 202 to be presented without accounting for light sources, surface textures, degree of transparency, etc. (e.g., without performing shading). Rather, these portions can be presented with a similar look to how the medical imaging data would be presented on a conventional DICOM viewer.

Figure 2D:
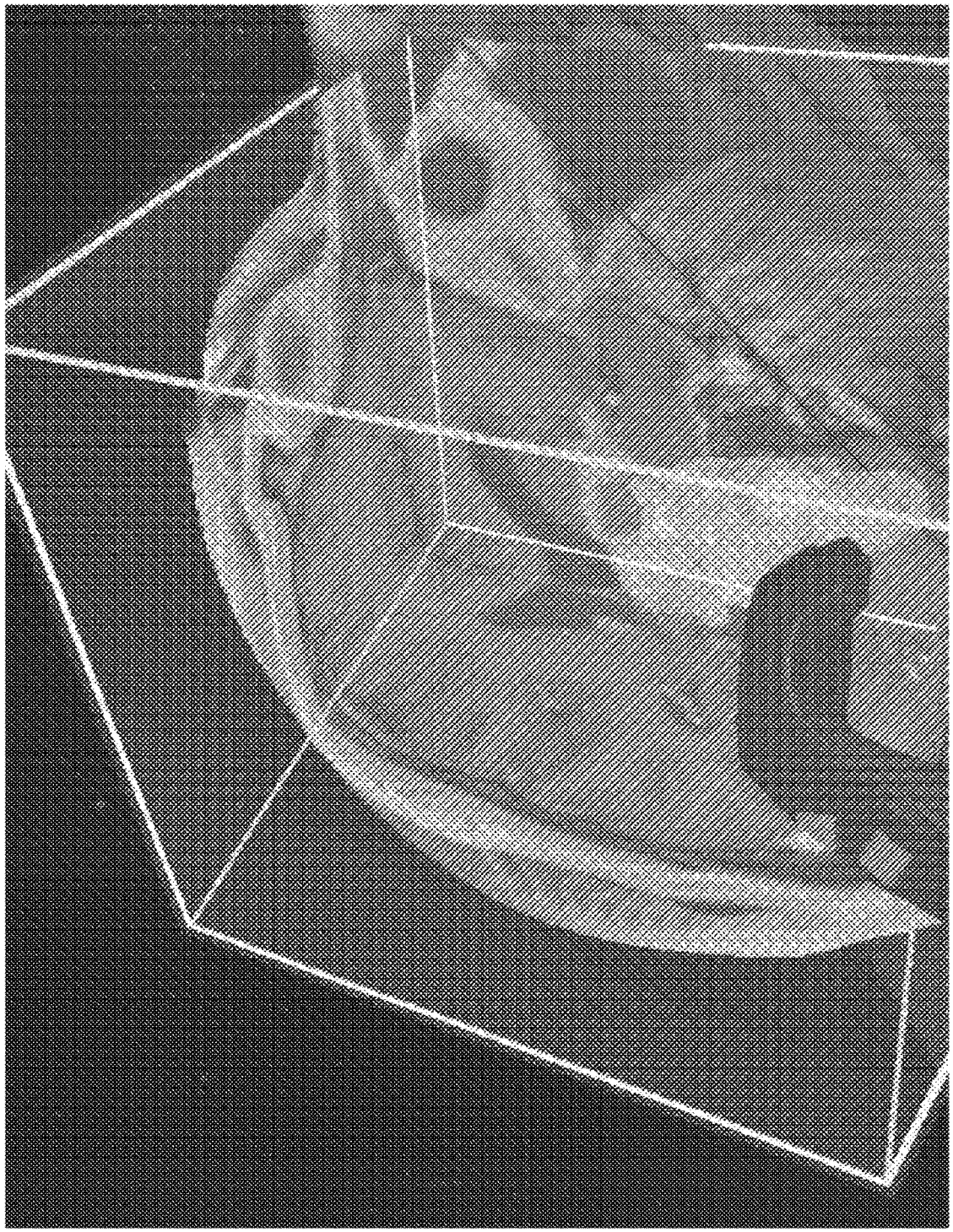
FIG. 2D shows an example of a 3D model based on a magnetic resonance imaging scan with a clip object intersecting a portion of the model exposing the underlying medical imaging data at the boundaries of the clip object presented within a virtual environment using a system configured in accordance with some embodiments of the disclosed subject matter.
Figure 2E:
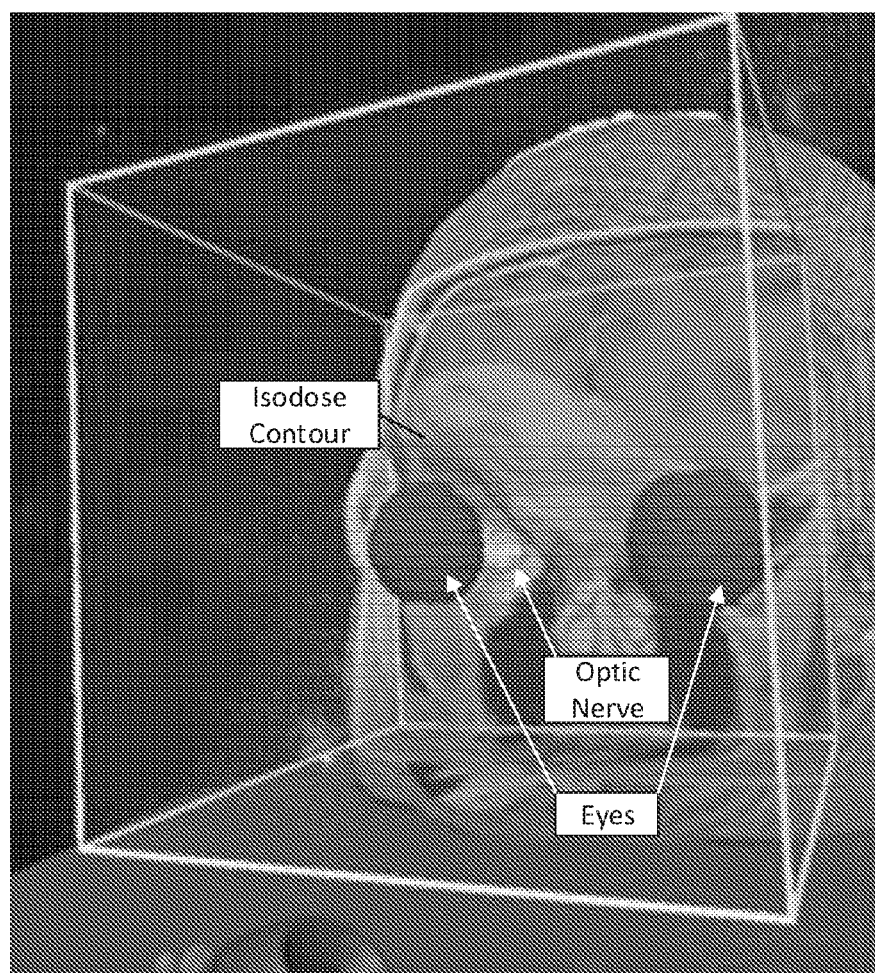
FIGS. 2E and 2F show examples of a 3D model based on a magnetic resonance imaging scan with a clip object intersecting a portion of the mod& exposing the underlying medical imaging data at the boundaries of the clip object, and segmentations presented within the clip object's boundaries in accordance with some embodiments of the disclosed subject matter.
Figure 2F:
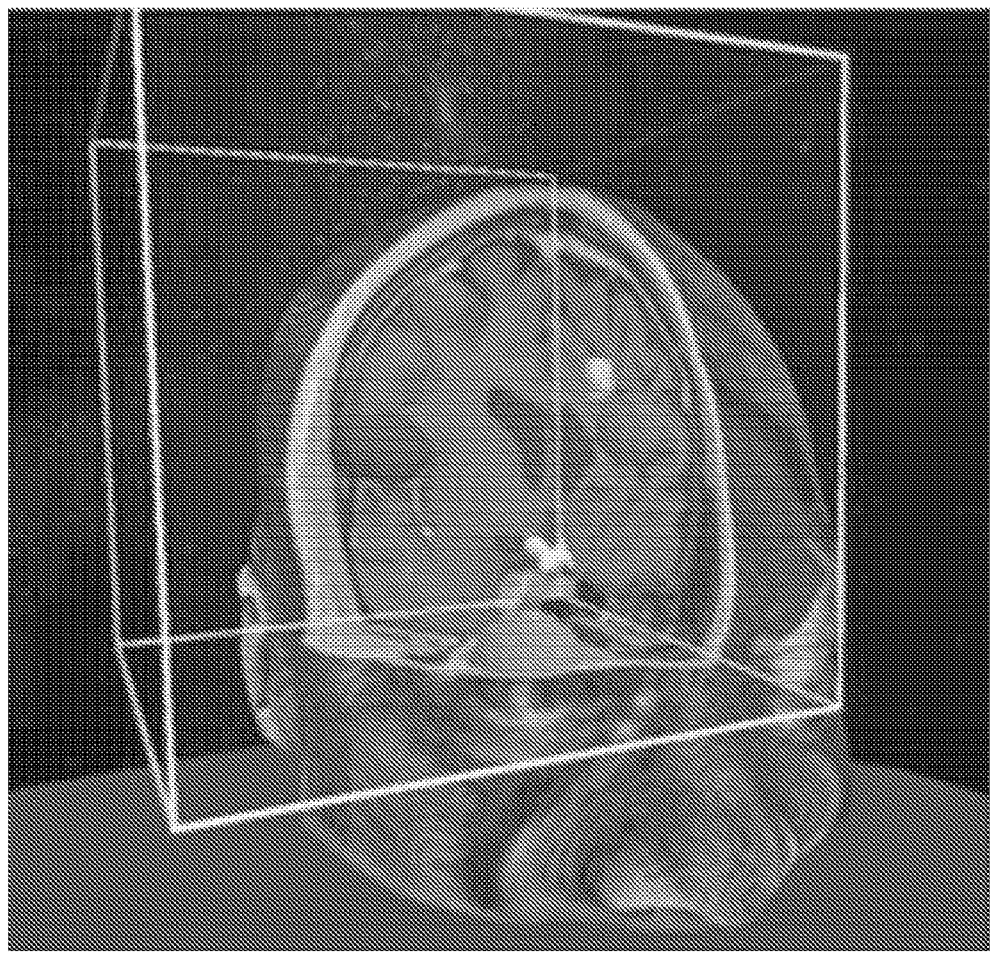

In some embodiments, (e.g., as shown in FIGS. 2E and 2F) though not shown, information can be presented within the space defined by a clip object. For example, in some embodiments, contouring can be presented within the clip object. In such an example, when one or more portions of the 3D array of medical imaging data is associated with contouring (note that some techniques for contouring are described below in connection with FIGS. 9 to 10E), the contour information can be presented within the clip object. As another example, in some embodiments, a user can choose portions of the 3D array of imaging data within the clip object using filtering techniques to present voxels meeting one or more criteria. In a more particular example, the user can select a range of intensity values to present within the clip object (e.g., as described below in connection with FIGS. 7 to 8E with regard to the entirety of the image data), and portions of the 3D array that both fall within the clip object and meet the one or more criteria can be presented as a 3D portion of a model using the underlying intensity values for the voxels, and in some cases can perform one or more shading operations to account for lighting and reflections (e.g., as described below in connection with FIG. 6 when presenting the exterior surface of the 3D model). In some embodiments, a user can provide input to determine portions of the 3D array rendered within the clip object are shaded, or presented using the intensity values of the voxels without shading.

FIG. 2C shows an example 220 of an enlarged view of the 3D model of 102 and clip object 202 represented in FIG. 2B in accordance with some embodiments of the disclosed subject matter. As shown in FIG. 2C, the areas at which the boundary of clip object 202 intersects with object 102 can expose different portions of the interior of object, while the space within clip object 202 can be rendered as transparent (i.e., portions of the medical imaging data that lie within clip object 202 can be omitted from rendering). As shown, due to the cuboid shape of clip object 202, multiple orthogonal surface 222, 224, and 226 can expose underlying medical imaging data at each of the faces. This can allow a user to view multiple areas of the volumetric medical imaging data simultaneously, and in the context of other portions of a subject's anatomy.

FIG. 2D shows an example of a 3D model based on a T1 MRI scan with a clip object intersecting a portion of the model exposing the underlying medical imaging data at the boundary of the clip object presented within a virtual environment using a system configured in accordance with some embodiments of the disclosed subject matter. As shown in FIG. 2D, a clip object is intersecting a head portion of a medical imaging scan. Portions on the boundary of the clip object are presented using the underlying DICOM data directly, while exterior portions are presented using conventional rendering techniques which give the model a 3D look through, for example, the use of shadows (among other techniques).

FIGS. 2E and 2F show examples of a 3D model based on a magnetic resonance imaging scan with a clip object intersecting a portion of the model exposing the underlying medical imaging data at the boundaries of the clip object, and segmentations presented within the clip object's boundaries in accordance with some embodiments of the disclosed subject matter. As shown in FIGS. 2E and 2F, in some embodiments, segmentations (e.g., as described below in connection with FIGS. 9 to 10E) associated voxels of the 3D array of medical imaging data that fall within the boundaries of a clip object can be rendered, while information from the underlying voxels of the 3D array of medical imaging data can be omitted.

Figure 3:
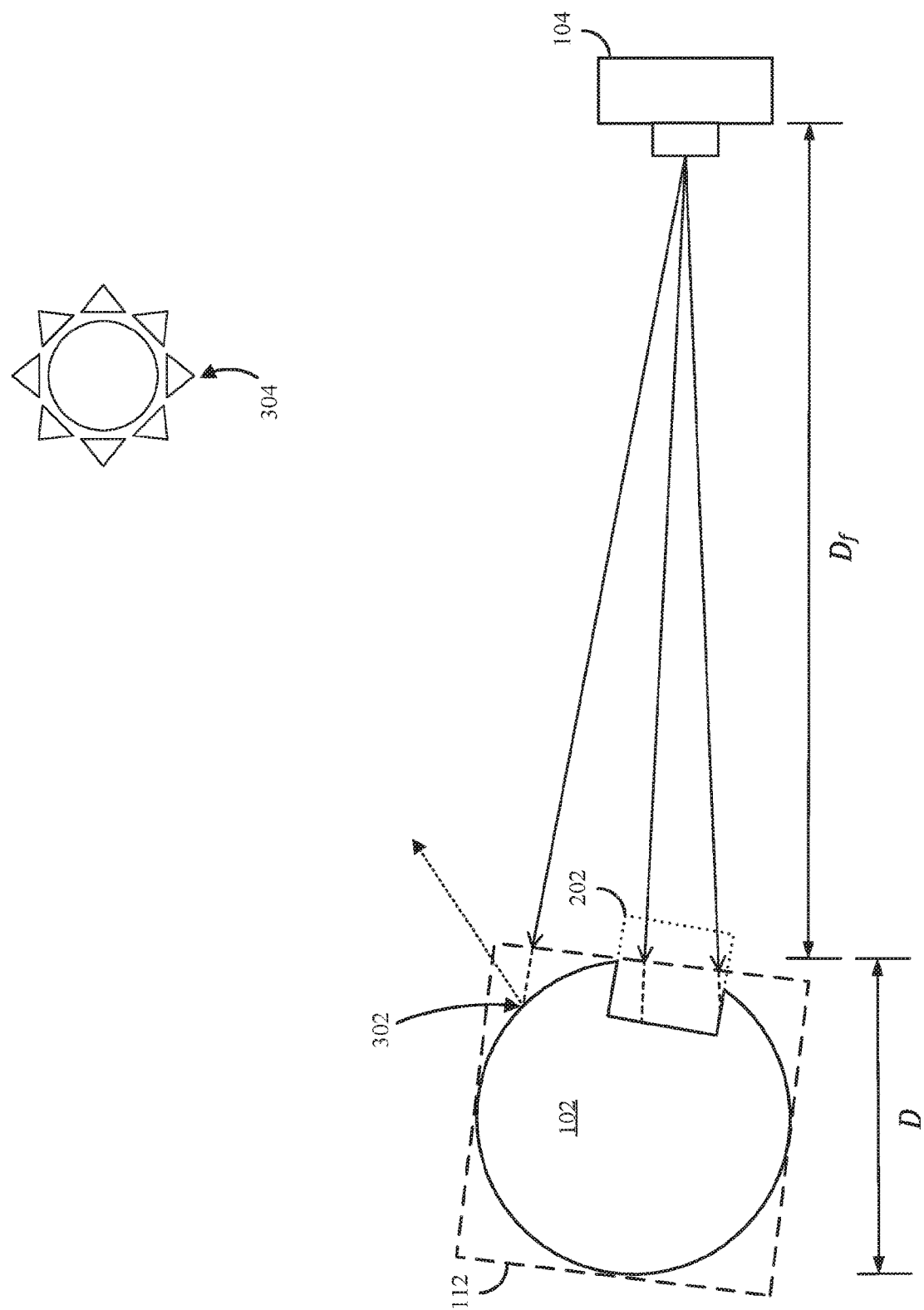
FIG. 3 shows an example of a 2D representation of a 3D scene illustrating ray casting techniques that can be used in connection with some embodiments of the disclosed subject matter.

FIG. 3 shows an example of a 2D representation of a 3D scene illustrating ray casting techniques that can be used in connection with some embodiments of the disclosed subject matter. As shown in FIG. 3, rays can be cast from virtual camera 104 toward object 102. As described above (and below in connection with FIG. 6), in some embodiments, the distance $D_f$ to the front of bounding box 112 can be determined (e.g., in a rendering or pre-rendering step), and rays cast from virtual camera 104 can be advanced to the front of bounding box 112. As shown in FIG. 3, distances $D_f$ to the front of bounding box 112 can be different for different pixels. For example, bounding box 112 can be at an angle to a central axis of the virtual camera, and accordingly rays cast from the virtual camera can intersect bounding box 112 at different distances.

In some embodiments, each ray can be advanced in increments until the ray intersects a portion of object 102 (and/or meets another stopping condition). For example, rays can be advanced (e.g., from bounding box 112) until they intersect an exterior surface of object 102 (e.g., at point 302), or an interior surface of object 102 exposed by a clip object (e.g., point 304 exposed by clip object 202). In some embodiments, each ray can be advanced any suitable amount, such as an increment that is less than the size of a single voxel of the underlying volumetric medical imaging data. This can ensure that the ray intersects the object at a voxel that is closest to virtual camera 104 along the direction of travel of the ray. In some embodiments, the mechanisms described herein can cast one ray per pixel that is to be used to display an image of the virtual environment.

In some embodiments, after a ray has intersected with an object (e.g., when the ray has met a stopping condition), the ray can be revert backward toward the virtual camera using a smaller increment step, the ray can then be advanced again with a yet smaller increment, until the location of the edge of the object (e.g., the location at which a stopping condition is met) can be determined to at least a threshold accuracy. For example, if the most recent increment is below a threshold distance and after the step the stopping condition changed states (e.g., from satisfied to unsatisfied, or vice versa), the midpoint between the previous two locations can be selected as the location at which the stopping condition is satisfied. As another example, if the most recent increment does not change the state of the stopping condition (e.g., the stopping condition remains unmet because an advancing step was not enough to cause the stopping condition to be satisfied, or vice versa), the most recent location at which the stopping condition was/is satisfied can be selected as the location at which the stopping condition is satisfied.

As described below in connection with FIG. 6, in some embodiments, when a stopping condition is satisfied at a location outside of a clip object (e.g., at an external surface of an object), the pixel associated with that ray can be rendered based on parameters associated with the one or more voxels with which the ray interacts, and parameters associated with the scene (e.g., brightness and/or location of one or more light sources, the presence of one or more objects that case a shadow on the location(s) of the voxels with which the ray interacts, etc.). In some embodiments, a calculated gradient of the 3D image that is rendered can be used to determine approximate normal vectors to use in one or more shading operations (e.g., to determine an angle at which light from a light source intersects each voxel used to render a portion of the surface).

Alternatively, in some embodiments, when a stopping condition is satisfied at a position that is associated with a clip object, the pixel associated with that ray can be rendered based on the intensity of the underlying medical imaging data directly (e.g., without taking into account brightness and/or location of light sources, other objects that may cast a shadow on the voxel, etc., i.e., without using shading techniques). In some such embodiments, presenting interior surfaces based on the underlying intensity without taking into account the properties of the virtual environment can allow a user to be confident that the intensity levels in the imaging data correspond to anatomical features captured in the data, not properties of the viewing environment. For example, this can facilitate presentation of the imaging data with an appearance that is similar to a conventional 2D DICOM viewer, while allowing the user more flexibility to manipulate, view, and/or interact with the imaging data.

Figure 4:
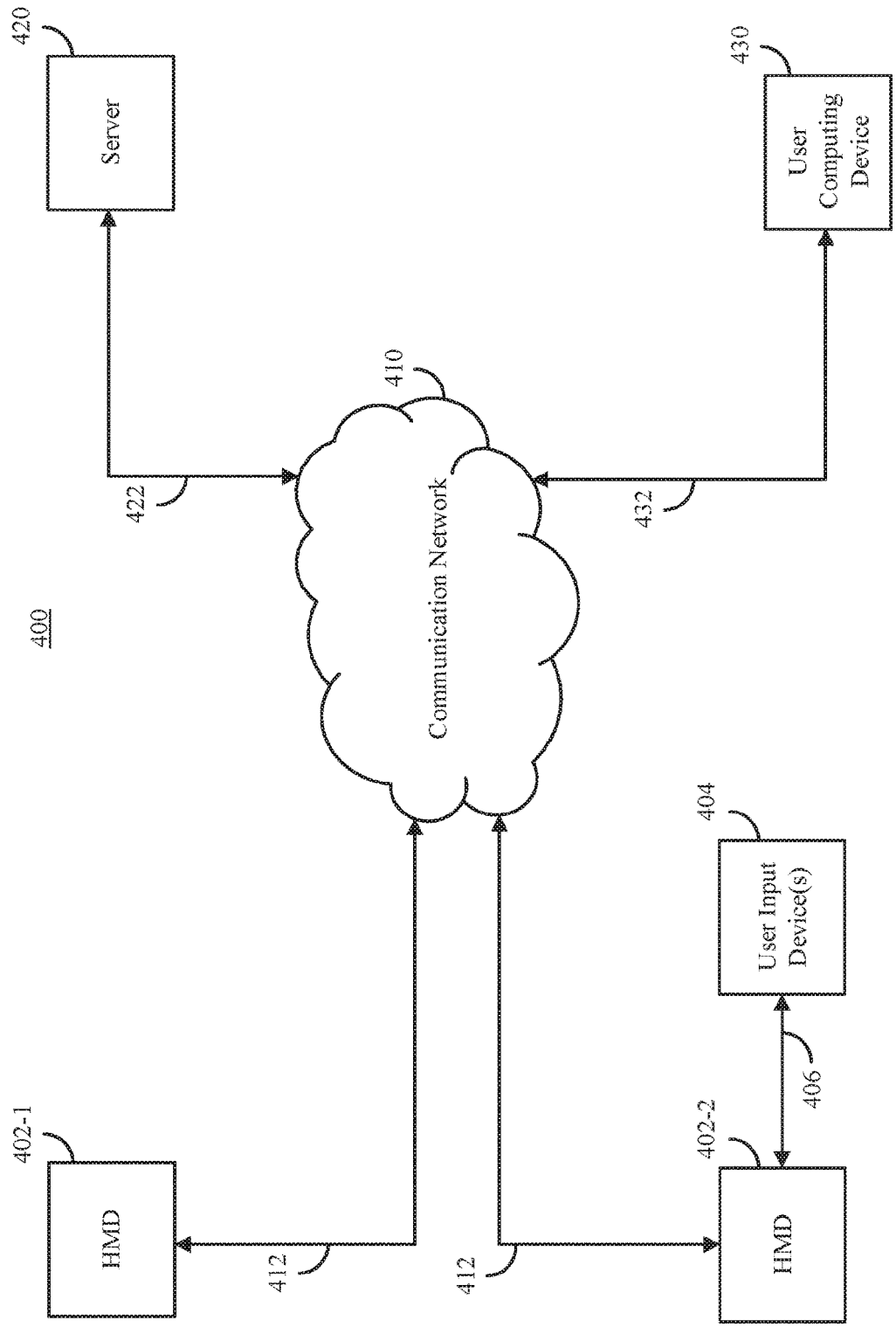
FIG. 4 shows an example 400 of a system including multiple head mounted displays and various computing devices that can be used to present medical imaging data in an interactive virtual reality environment in accordance with some embodiments of the disclosed subject matter.

FIG. 4 shows an example 400 of a system including multiple head mounted displays and various computing devices that can be used to present medical imaging data in an interactive virtual reality environment in accordance with some embodiments of the disclosed subject matter. As shown in FIG. 4, system 400 can include multiple HMDs 402-1 and 402-2 which can be located in the same physical space (e.g., in the same room), or located in different physical spaces (e.g., in a different room in the same building, in a different building in the same city, in a different city, in a different country, etc.). As described below in connection with FIGS. 6 and 15, HMDs 402-1 and 402-2 can interact to provide a collaborative experience in which the content being presented is synchronized, but the users can view the content from different angles.

In some embodiments, system 400 can include a server 420 that can provide and/or control content that is to be presented by one or more HMDs (e.g., HMDs 402-1 and/or 402-2). In some embodiments, server 420 can be implemented using any suitable computing device such as a server computer, an HMD, a tablet computer, a smartphone, a personal computer, a laptop computer, etc. In some embodiments, each HMD 402 can connect to a communication network 410 via a communications link 412, and server 420 can connect to communication network 410 via a communications link 422. In some embodiments, a user computing device 430 can connect to communication network 410 via a communications link 432. Communication network 410 can be any suitable communication network or combination of communication networks. For example, communication network 410 can be a Wi-Fi network (which can include one or more wireless routers, one or more switches, etc.), a peer-to-peer network (e.g., a Bluetooth network, a Zigbee mesh network, etc.), a cellular network (e.g., a 3G network, a 4G network, etc., complying with any suitable standard, such as CDMA, GSM, LTE, LTE Advanced, WiMAX, etc.), a wired network, etc. Communications links 412, 422, and 432 can each be any suitable communications link or combination of communications links, such as a Wi-Fi links, Bluetooth links, cellular links, etc.

Additionally, in some embodiments, system 400 can include one or more user input devices 404, which can communicate with an HMD (e.g., HMD 402-2) via a communications link 406. In some embodiments, communications link 406 can be any suitable communications link that can facilitate communication between user input device(s) 404 and HMD 402-2. For example, communications link 406 can be a wired link (e.g., a USB link, an Ethernet link, a proprietary wired communication link, etc.) and/or a wireless link (e.g., a Bluetooth link, a Wi-Fi link, etc.). In some embodiments, user input device(s) 404 can include any suitable sensors for determining a position of user input device 404 with respect to one or more other devices and/or objects (e.g., HMD 402-2, a particular body part of a wearer of HMD 402-2, etc.), and/or a relative change in position (e.g., based on sensor outputs indicating that a user input device 404 has been accelerated in a particular direction, that a user input device 404 has been rotated in a certain direction, etc.). For example, in some embodiments, user input device 404 can include one or more accelerometers, one or more gyroscopes, one or more electronic compasses, one or more image sensors, an inertial measurement unit, etc.

In some embodiments, user input device(s) 404 can be used as a pointing device by the wearer of HMD 402-2 to highlight a particular portion of content (e.g., to segment a portion of object 102) being presented by HMD 402-2, to select a particular portion of object 102 and/or a clip object (e.g., to control the orientation of the object, to control a position of the object, etc.), to control one or more user interfaces resented by HMD 402-2, etc. In some embodiments, a second HMD 402-1 that is presenting the same content in a collaborative virtual environment (e.g., an HMD worn by a colleague of the user, a patient of the user, etc.) can present representations of user input device(s) 404 (e.g., to provide context to actions being performed by a user of HMD 402-2). In some embodiments, each other user in a collaborative environment can be represented by an avatar at a position in the virtual environment corresponding to that user's viewport. Additionally, in some embodiments, representations of user input devices, clip objects, surgical instruments, etc., associated with the other user can be also be presented within the virtual environment.

In some embodiments, HMD 402-2 and/or server 420 can receive data from user input device(s) 404 indicating movement and/or position data of user input device(s) 404. Based on the data from user input device(s) 404, HMD 402-2 and/or server 420 can determine one or more changes to the content being presented (e.g., a change in orientation and/or position of object 102, a change in orientation and/or position of a clip object 202, a location of a contouring brush, one or more voxels that have been segmented using the contouring brush, etc.). In some embodiments, user input device(s) 404 can be implemented using any suitable hardware. For example, user input device(s) 404 can include one or more controllers that are configured to receive input via one or more hardware buttons, one or more touchpads, one or more touchscreens, one or more software buttons, etc. As another example, user input device(s) 404 can include one or more controllers that are configured to receive input via translation and/or rotation along and around various axes, such as a 6 DOF controller (e.g., a VIVE controller, as described above).

In some embodiments, user input device(s) 404 can be an integral part of HMD 402-2, which can, for example, determine a direction in which HMD 402-2 is pointing with respect to a virtual environment and/or virtual object(s). The information on which direction HMD 402-2 is pointing can be used to infer a direction in which the wearer's eyes are looking (which can, for example, be augmented based on gaze information, in some cases). In some embodiments, the inferred location at which the wearer of HMD 402-2 is looking can be used as input to position one or more user interface elements with respect to the virtual environment and/or virtual object, and/or to control an orientation, magnification, and/or position at which to present a virtual object (e.g., as the direction in which a user looks changes, HMD 402-2 can change how content is rendered to allow a user to move around an object as though the object were physically present in front of the user).

In some embodiments, user input device(s) 404 can be a separate device(s) that can convey location information and/or movement information to HMD 402-2 and/or server 420, which can then be used to generate on or more user interface elements (e.g., representations of user input device(s) 404), to facilitate user interaction with the virtual environment being presented via HMD 402-2, and/or virtual object(s) in the virtual environment.

In some embodiments, a user can interact with server 420 via a user computing device 430 to select content that is to be presented by HMD 402-2 (e.g., a particular scan to be presented). For example, the user can instruct server 420 to send HMD 402-2 and/or any other suitable HMDs images corresponding to a particular volumetric medical imaging scan (e.g., MRI scan, CT scan, etc.). Additionally or alternatively, in some embodiments, the user can log in to an application executed by HMD 402-2, and/or a service provided via HMD 402-2, using user computing device 430.

In some embodiments, the user can generate a virtual scene to be presented by one or more HMDs 402 via user computing device 430 and/or server 420. For example, a user can select imaging data to be used, one or more surgical instruments that are to be made available (e.g., for planning a surgical intervention), one or more filters to be made available (e.g., a range or ranges of intensity values and/or Hounsfield values) as preset filters during within the virtual environment, etc. As another example, in some embodiments, a user can use a conventional DICOM viewer to perform a segmentation of the imaging information (e.g., a user that does not have access to the mechanisms described herein), and can cause the segmentation to be associated with the volumetric medical imaging data. In such an example, such a segmentation can be used by HMD 402-2 to present the segmentation with a 3D model generated from the volumetric medical imaging data (e.g., as described below in connection with FIG. 9).

In some embodiments, the user can upload content and/or identifying information of content to server 420 that is to be presented by HMDs 402 from user computing device 430. For example, the user can upload volumetric medical imaging data, information about a surgical tool (e.g., dimensions, materials, color(s), etc.), information about a radiation source (e.g., dimensions, operating parameters, power, etc.), and/or any other suitable information that can be used in connection with some embodiments of the disclosed subject matter. As another example, the user can provide location information (e.g., a URL) at which content to be presented can be accessed. In some embodiments, HMDs 402 can download and/or save the content at any suitable time. For example, the user or an administrator can download, sideload and/or otherwise transfer the content to be viewed to each HMD 402.

In some embodiments, user computing device 430 can be any suitable computing device or combination of devices, such as a personal computer, a laptop computer, a tablet computer, a smartphone, a wearable computer, a head mounted display (e.g., HMD 402), etc. In some embodiments, a user can select content, upload content, etc., using user computing device 430 and/or server 420 using any suitable technique or combination of techniques. For example, user computing device 430 can execute an application from memory that is configured to facilitate selection of volumetric medical imaging data to be presented, assembling the volumetric medical imaging data into a 3D array to be used in generating a 3D model, uploading the volumetric medical imaging data to a server (e.g., server 420) for distribution to one or more HMDs (e.g., HMDs 402), downloading the volumetric medical imaging data to one or more HMDs (e.g., HMDs 402), etc.

In some embodiments, each HMD 402 can execute an application that can use volumetric medical imaging data to present a 3D model of a subject based on the medical imaging scan. Additionally, in some embodiments, one or more HMDs 402 can each execute an application that can interact with server 420 (e.g., over communication network 410) to receive volumetric medical imaging data to present a 3D model, send and/or receive information about the actions of one or more other users sharing a collaborative (e.g., how a user is manipulating one or more objects in the virtual environment) to facilitate a shared experience.

In some embodiments, server 420 can be located locally or remotely from HMDs 402. Additionally, in some embodiments, multiple servers 420 can be used (which may be located in different physical locations) to provide different content, provide redundant functions, etc. In some embodiments, an HMD 402 in system 400 can perform one or more of the operations of server 420 described herein, such as instructing HMDs when another HMD has interacted with the virtual environment, how the HMD interacted with the virtual environment, for distributing updated information, etc.

In some embodiments, a user of any suitable HMD (e.g., HMD 402-2) can control presentation of the content in the virtual environment by providing input to the HMD. For example, one HMD can be designated as having control of the virtual environment and/or one or more objects within the virtual environment, and other HMDs may be locked out from making changes to the virtual environment and/or one or more objects within the virtual environment that are not currently controlled by that HMD.

Figure 5:
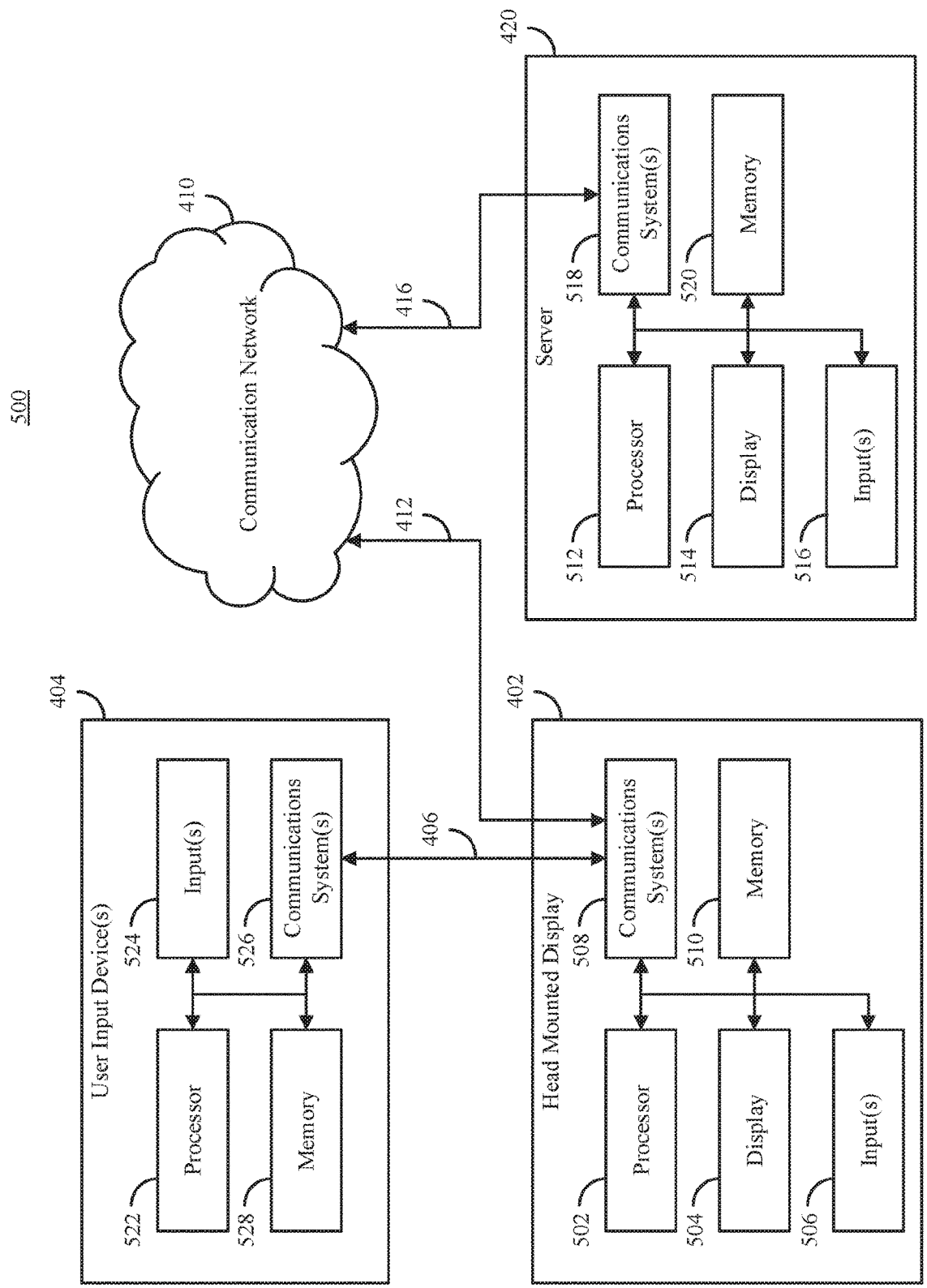
FIG. 5 shows an example 500 of hardware that can be used to implement at least one HMD 402, user input device 404, and server 430 shown in FIG. 4 in accordance with some embodiments of the disclosed subject matter.

FIG. 5 shows an example 500 of hardware that can be used to implement at least one HMD 402, user input device 404, and server 430 shown in FIG. 4 in accordance with some embodiments of the disclosed subject matter. As shown in FIG. 5, in some embodiments, HMD 402 can include a processor 502, a display 504, one or more inputs 506, one or more communication systems 508, and/or memory 510. In some embodiments, processor 502 can be any suitable hardware processor or combination of processors, such as a central processing unit (CPU), a graphics processing unit (GPU), etc. In some embodiments, display 504 can include any suitable display device(s), such as a stereoscopic display, a transparent display, etc. In some embodiments, inputs 506 can include any suitable input device(s) and/or sensor(s) that can be used to receive user input, such as a 6 DOF user input device, and one or more sensors (e.g., one or more gaze tracking sensors, one or more head tracking sensors, one or more motion sensors, etc.).

In some embodiments, communications systems 508 can include any suitable hardware, firmware, and/or software for communicating information over communication network 410 and/or any other suitable communication networks. For example, communications systems 508 can include one or more transceivers, one or more communication chips and/or chip sets, etc. In a more particular example, communications systems 508 can include hardware, firmware and/or software that can be used to establish a Wi-Fi connection, a Bluetooth connection, a cellular connection, etc.

In some embodiments, memory 510 can include any suitable storage device or devices that can be used to store instructions, values, etc., that can, for example, cause processor 502 to present a virtual environment using display 504, to communicate with server 420 via communications system(s) 508, etc. Memory 510 can include any suitable volatile memory, non-volatile memory, storage, any other suitable type of storage medium, or any suitable combination thereof. For example, memory 510 can include RAM, ROM, EEPROM, one or more flash drives, one or more hard disks, one or more solid state drives, one or more optical drives, etc. In some embodiments, memory 510 can have encoded thereon a computer program for controlling operation of HMD 402. In some such embodiments, processor 502 can execute at least a portion of the computer program to present content (e.g., one or more 3D models), receive content from server 420, transmit information to server 420, etc. In some embodiments, the HMD 402 can use any suitable hardware and/or software for rendering one or more portions of the virtual environment including the 3D model. For example, one or more portions of the rendering processes described herein can use Unity 3D to perform one or more rendering operations, while one or more other portions of the rendering processes can be performed using operations that are not included in Unity 3D. Additionally, in some embodiments, any suitable communications protocols can be used to communicate control data, medical imaging data, audio, etc., between HMD 402 and server 420. Note that although the mechanisms described herein are generally described as being used in connection with an HMD, this is merely an example, and the mechanisms can be used in connection with other presentation hardware that can provide an immersive experience, such as a room scale immersive environment.

In some embodiments, server 430 can include a processor 512, a display 514, one or more inputs 516, one or more communication systems 518, and/or memory 520. In some embodiments, processor 512 can be any suitable hardware processor or combination of processors, such as a CPU, a GPU, etc. In some embodiments, display 514 can include any suitable display devices, such as a computer monitor, a touchscreen, a television, a stereoscopic display, etc. In some embodiments, inputs 516 can include any suitable input devices and/or sensors that can be used to receive user input, such as a keyboard, a mouse, a touchscreen, a microphone, etc.

In some embodiments, communications systems 518 can include any suitable hardware, firmware, and/or software for communicating information over communication network 410 and/or any other suitable communication networks. For example, communications systems 518 can include one or more transceivers, one or more communication chips and/or chip sets, etc. In a more particular example, communications systems 518 can include hardware, firmware and/or software that can be used to establish a Wi-Fi connection, a Bluetooth connection, a cellular connection, etc.

In some embodiments, memory 520 can include any suitable storage device or devices that can be used to store instructions, values, etc., that can, for example, cause processor 512 to present content using display 514, to communication with one or more HMDs 402, etc. Memory 520 can include any suitable volatile memory, non-volatile memory, storage, any other suitable type of storage medium, or any suitable combination thereof. For example, memory 520 can include RAM, ROM, EEPROM, one or more flash drives, one or more hard disks, one or more solid state drives, one or more optical drives, etc. In some embodiments, memory 520 can have encoded thereon a server program for controlling operation of server 420. In some such embodiments, processor 512 can execute at least a portion of the computer program to transmit content (e.g., volumetric medical imaging data that can be used to render a 3D model) to one or more HMDs 402, receive content from one or more HMDs 402, receive instructions from one or more devices (e.g., HMD 402-2, user input device 404, another server, a personal computer, a laptop computer, a tablet computer, a smartphone, etc.).

In some embodiments, user input device 404 can include a processor 522, one or more inputs 524, one or more communication systems 526, and/or memory 528. In some embodiments, processor 522 can be any suitable hardware processor or combination of processors, such as a CPU, a GPU, etc. In some embodiments, inputs 524 can include any suitable input devices and/or sensors that can be used to receive user input, such as one or more physical or software buttons, one or movement sensors, a microphone, a touchpad, a touchscreen, etc.

In some embodiments, communications systems 526 can include any suitable hardware, firmware, and/or software for communicating information over communications link 406 and/or any other suitable communications links. For example, communications systems 526 can include one or more transceivers, one or more communication chips and/or chip sets, etc. In a more particular example, communications systems 526 can include hardware, firmware and/or software that can be used to establish a Wi-Fi connection, a Bluetooth connection, a cellular connection, etc.

In some embodiments, memory 528 can include any suitable storage device or devices that can be used to store instructions, values, etc., that can be used, for example, by processor 522 to determine when user input is received, to record sensor data, to communicate sensor data with one or more HMDs 402, etc. Memory 528 can include any suitable volatile memory, non-volatile memory, storage, any other suitable type of storage medium, or any suitable combination thereof. For example, memory 528 can include RAM, ROM, EEPROM, one or more flash drives, one or more hard disks, one or more solid state drives, one or more optical drives, etc. In some embodiments, memory 528 can have encoded thereon a computer program for controlling operation of user input device 404. In such embodiments, processor 522 can execute at least a portion of the computer program to transmit data (e.g., representing sensor outputs) to one or more HMDs 402, to transmit data (e.g., representing sensor outputs) to one or more servers 420, etc.

Figure 6:
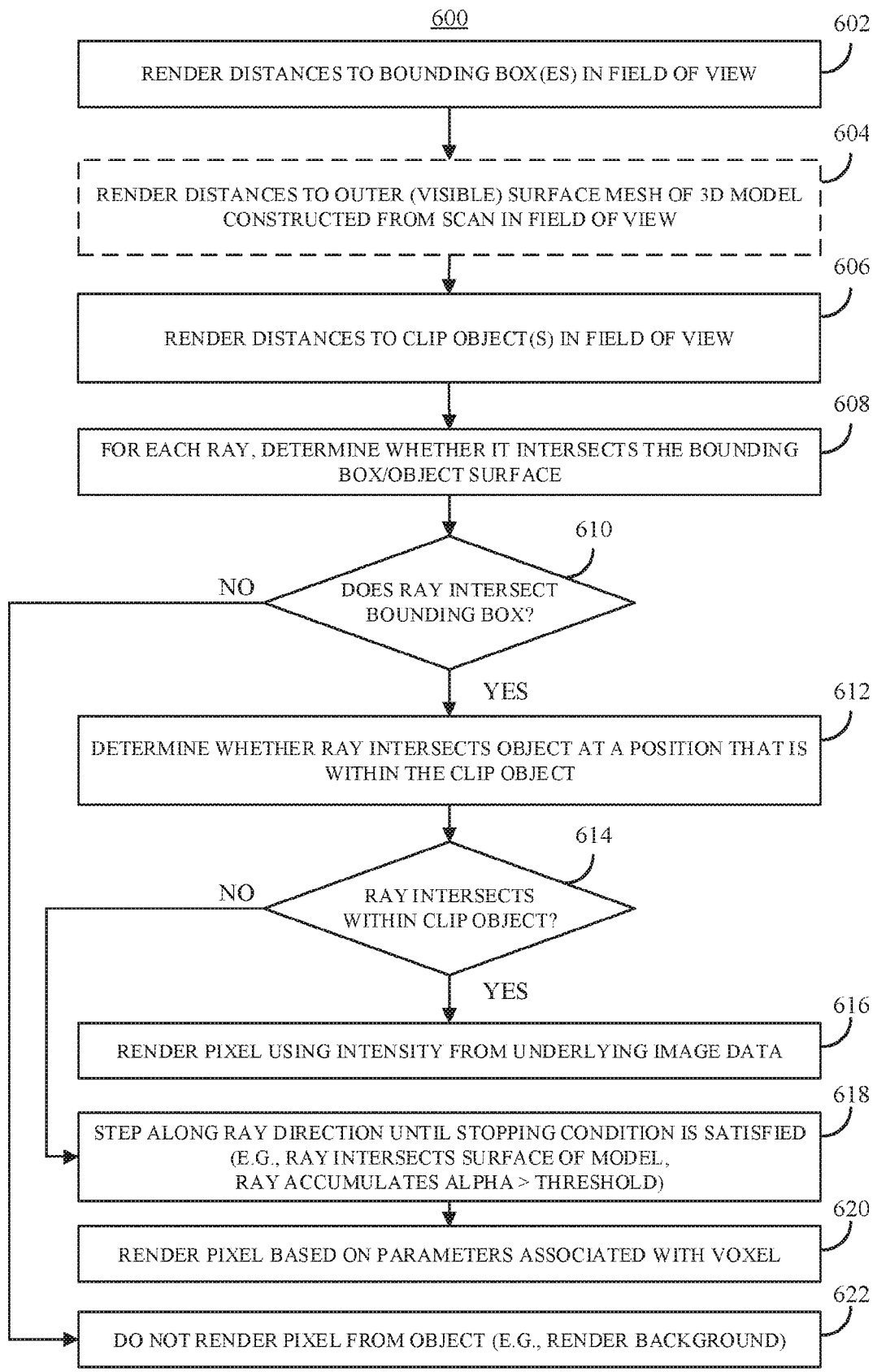
FIG. 6 shows an example 600 of a process for rendering medical imaging data in a 3D virtual environment in accordance with some embodiments of the disclosed subject matter.

FIG. 6 shows an example 600 of a process for rendering medical imaging data in a 3D virtual environment in accordance with some embodiments of the disclosed subject matter. As shown in FIG. 6, process 600 can begin at 602 by rendering distances to bounding boxes delineating the dimensions of an object in the field of view to be presented to a user. In some embodiments, process 600 can render distances to one or more bounding boxes such that the distance is available when beginning to render the virtual environment. In some embodiments, the boundaries of the bounding box can be determined using any suitable technique. For example, process 600 can scale a rectangular 3D object (e.g., a rectangular cuboid) to the relative extents of the 3D array of volumetric medical imaging data that is to be used to render a 3D model of a subject's anatomy. In some embodiments, process 600 can calculate the distance from each eye of the user (e.g., represented by a virtual camera that determines the viewport into the virtual environment) to the front and, in some cases, back of the bounding box (from the viewpoint of the virtual camera) for each pixel that is to be rendered, which can define the maximum extent over which ray casting is to be performed. For example, the bounding box can be a rectangular cuboid, and process 600 can determine the distance to the point at which a ray cast through a particular pixel intersects a face of the bounding box based on a calculated distance to a mesh representing the bounding box. Note that, in some embodiments, the bounding box can be in any orientation with respect to the virtual camera, and accordingly, the distance to the bounding box for each pixel is likely to be different. In some embodiments, process 600 can store the distances for each pixel to the front and back faces of the object by rendering the distances to 2D textures on the processor (e.g., GPU) executing process 600. Additionally, process 600 can store information indicating which rays did not intersect the bounding box (e.g., as a particular value in the 2D texture).

In some embodiments, at 604, process 600 can define an external surface for the 3D array of volumetric medical imaging data that represents the subject of the scan. For example, process 600 can generate a triangular mesh that represents the external surface of the subject represented in the 3D array of volumetric medical imaging data. In some embodiments, process 600 can calculate the distance from each eye of the user (e.g., represented by a virtual camera) to the exterior surface (e.g., the closest and farthest points at which the ray intersects the triangular mesh representing the surface), which can define the maximum extent over which ray casting is to be performed. In some embodiments, this distance (or distances) can be compared to the distances calculated by process 600 based on the extent of the bounding box at 602, and can be used to overwrite the value(s) for the pixel in the 2D texture if the distance is larger than the distance calculated using the bounding box (e.g., for the first intersection with the surface), and/or if the distance is smaller (e.g., for the second intersection with the surface). In some embodiments, 604 can be omitted, and rendering can be performed based on the distances to the bounding box.

In some embodiments, at 606, process 600 can render distances to a clip object that is present within the field of view of the user. In some embodiments, process 600 can render the clip object using global coordinates to determine where in the virtual environment the clip object is located. For example, process 600 can render the clip object using global coordinates, which can allow a user to move, rotate, scale, etc., one or more objects within the scene without affecting the location and/or size of the clip object. Additionally or alternatively, in some embodiments, process 600 can render the clip object using relative coordinates (e.g., as described below in connection with FIG. 11) based on the position and orientation of another object (e.g., the 3D array of medical imaging data) to determine where in the virtual environment to present the surgical instrument. For example, process 600 can render the clip object using relative coordinates to allow a user to move, scale, etc., the object and maintain the relative size and position of the clip object with respect to the object. In some embodiments, the clip object can be rendered based on global coordinates unless a user specifies that the clip object is to be rendered using relative coordinates. For example, process 600 can receive input indicating that the clip object is to be associated with the object. In a more particular example, a user can provide input indicating that the clip object is to be "locked" or "attached" to the object. In some embodiments, the clip object can be represented by a 3D triangular mesh, and process 600 can pre-render distances to the clip object such that the distance is available when beginning to render the virtual environment. In some embodiments, process 600 can calculate the distance to each portion of the mesh, and can render the distances into a GPU texture for use in determining the extents of the rendering (e.g., similarly to what is described above in connection with determining distances to the bounding box at 602). In some embodiments, process 600 can determine which pixels intersect the clip object using a fragment shader (e.g., executed by a GPU). As described above in connection with 602, process 600 can determine distances to the front and back of the clip object (e.g., the first and second point at which a ray cast from a particular pixel intersects the surface of the clip object).

In some embodiments, at 608 process 600 can determine, for each pixel to be rendered, whether a ray cast from through that pixel toward the scene intersects the bounding box. In some embodiments, process 600 can use any suitable technique or combination of technique to determine whether the ray intersects the bounding box and/or the object. For example, in some embodiments, process 600 can determine the distance, for each pixel, to the front of the bounding box, and can begin ray casting from the stored distance.

At 610, process 600 can determine whether the ray intersects the bounding box for the object and/or the surface mesh corresponding the external surface of the 3D array of medical imaging data. In some embodiments, process 600 can determine whether each ray intersects the bounding box/object surface based on the distances calculated at 602 and/or 604. For example, in some embodiments, process 600 can query the 2D texture to determine whether the ray intersects the bounding box (e.g., is associated with one or more distances to the bounding box). As another example, in some embodiments, process 600 can determine whether the a ray intersects the bounding box/object by advancing the ray to the distance specified in the 2D texture, and determining at that point whether it coincides with the bounding box/object.

If process 600 determines that a ray does not intersect the bounding box ("NO" at 610), process 600 can move to 622, at which process 600 can render a value for the pixel that corresponds to something other than a voxel from the 3D array of medical imaging data. For example, the pixel can be rendered using a background image or texture. As another example, the pixel can be rendered based on data from another object which the ray does intersect (e.g., if there are multiple objects in the user's field of view).

Otherwise, if process 600 determines that a ray intersects the bounding box ("YES" at 610), process 600 can move to 612. At 612, process 600 can determine whether the ray intersects the object at a position that corresponds to a boundary of the clip object. In some embodiments, process 600 can use any suitable technique to determine whether the ray intersects the object within the clip object, such as one or more ray marching techniques. For example, in some embodiments, process 600 can compare, for each pixel, the distance to the front of the bounding box/object surface and the distance to the front and/or back of the clip object. In such an example, process 600 can begin ray marching at the distance that is farthest from the virtual camera. In some embodiments, such as in cases in which process 600 begins raymarching at either the bounding box or clip object, process 600 can determine whether the first step in the raymarching intersects a voxel. If the first step does intersect a voxel, process 600 can determine that the ray intersects at a position within the clip object, and if not can continue a raymarching operation for that ray. As another example, process 600 can determine that the ray intersects the object at a position within the clip object based on the comparison of the distances to the front of the object and the back of the clip object. In some embodiments, in cases in which the front of the clip object is farther than the front of the surface (and/or bounding box), process 600 can begin raymarching at the bounding box/object surface distance, rather than the clip object distance. For example, if the clip object is positioned to be entirely within the object, process 600 can use the distance to the bounding box/object surface as the position to begin raymarching. Alternatively, in some embodiments, in cases in which the front of the clip object is farther than the front of the surface (and/or bounding box), process 600 can begin raymarching at the rear of the clip object, which can appear to increase and/or change the dimensions of the bounding box.

If process 600 determines that the ray intersects the object within the clip object ("YES" at 614), process 600 can move to 616 and can render the pixel using a value that is based on the direct intensity value(s) of the underlying 3D array of imaging data directly (e.g., rather than using ray tracing techniques that take into account lighting and/or reflections, such as shading, recursive ray tracing, etc.). In some embodiments, process 600 can, at each step, interpolate an intensity value from the 3D array of medical imaging data to determine an intensity value for the current position of the ray. For example, process 600 can perform a trilinear interpolation that determines the value based on eight voxels that form the corners of a cube centered on the current location of the ray. Note that, because the clip object can intersect the 3D array at an oblique angle (e.g., not along the axial, coronal, or sagittal plane), there may not be a voxel value corresponding to the point at the current location of the ray. Interpolation of the value can provide an approximation of the value at that point (or a relatively precise value when the ray is co-located with the position of the voxel) without causing a pixelated appearance by relying on merely using the value of the nearest voxel.

Otherwise, if process 600 determines that the ray intersects the object outside of the clip object ("NO" at 614), process 600 can move to 618. In some embodiments, at 618, process 600 can use one or more ray marching techniques to determine whether, and at what distance, each ray satisfies a stopping condition. For example, for each pixel, process 600 can begin ray marching from the distance stored in the 2D texture representing the distance from the virtual camera to the front surface of the bounding box. As another example, process 600 can begin ray marching from the distance stored in the 2D texture representing the distance from the virtual camera to the surface of the object as represented by a triangular mesh. Note that, in some embodiments, if the ray reaches the rear surface of the bounding box or object without otherwise satisfying a stopping condition, process 600 can render a value unrelated to the 3D array, such as based on a background image.

In some embodiments, from the starting point for each ray, process 600 can advance the ray by a small distance along the direction of the ray and interrogate a 3D texture representing the 3D array of medical imaging data after the step is taken. Process 600 can continue to advance the rays in steps (of a set or variable length), and after each step can compare the voxel value at that location to a threshold value. For example, after each step, process 600 can read the value from the texture corresponding to the surface of the 3D array of medical imaging data (e.g., the texture generated at 604), and can determine whether the stopping condition is satisfied based on whether the position stored in the texture is less than the distance to the current ray position. In some embodiments, if process 600 determines that the value exceeds the threshold, process 600 can begin a process of more precisely determining the location at which the ray intersects the object and/or when the stopping condition is satisfied. For example, process 600 can take a step backward along the direction of the ray and compare the voxel value at that location to the threshold, and continue stepping forward and backward at smaller increments until the point at which the threshold is first passed is more precisely determined. Additionally or alternatively, in some embodiments, after each step, process 600 can determine whether it has intersected a voxel of an object in the scene, and can add the value of the voxels alpha channel (i.e., the value representing the degree to which the voxel is transparent or opaque), and can continue accumulating alpha values until an alpha threshold is reached. For example, process 600 can use such techniques when transparent blending techniques are used. In some embodiments, the depth at which the ray intersects the object can be stored as a depth in the z-buffer for the pixel being rendered.

In some embodiments, when process 600 determines the location (or locations) at which the ray intersects the object's external surface, process 600 can move to 620, and can render the value for the pixel based on one or more parameters associated with the voxel(s) at which the stopping condition is satisfied. In some embodiments, process 600 can use any suitable technique or combination of techniques to determine the value to be rendered. For example, process 600 can look up the voxel value surface at the point(s) at which the ray intersects the object, and can adjust the rendered value based on the location of a light source, and any other objects in the scene that may interfere with light from the light source. In a more particular example, process 600 can use a normal vector (e.g., calculated based on a gradient of the surface) and the location of a light source to determine how to alter the underlying intensity to provide a more realistic 3D image (e.g., process 600 can perform a shading operation).

Note that, under traditional 3D image visualization methods each pixel would be rendered based on techniques described above for rendering the surface of the object. However, in many applications, including as medical image visualization, it is important for a user to also see the voxel values of the underlying image. In conventional viewers, the process of viewing the values of the underlying image is performed using a 2D by displaying individual planes extracted from the 3D image voxel array. Conventional viewers often only allow planes along the cardinal orthogonal axes of the array (e.g., the axial, coronal and sagittal planes of the subject) to be viewed. Using clip objects to expose the underlying values from the image, as well as presenting the exterior surface as a rendered surface influenced by lighting and other properties of the scene can present clinicians with the necessary information to assess the intensity features of the image, while also providing additional 3D context through rendering of the exterior surface.

In some embodiments, process 600 be executed to render a value for each pixel, and can be executed repeatedly (e.g., before every frame is displayed) to update the location of the object(s) in the scene that may have changed in response to user input (e.g., to move the object using a user input device, to move the user's point of view by moving the HMD being used to present the content, etc.). Additionally, note that, in some embodiments, process 600 can be carried out for two images to produce a stereoscopic pair of images. For example, raymarching can be performed for both images using a single combined process.

Figure 7:
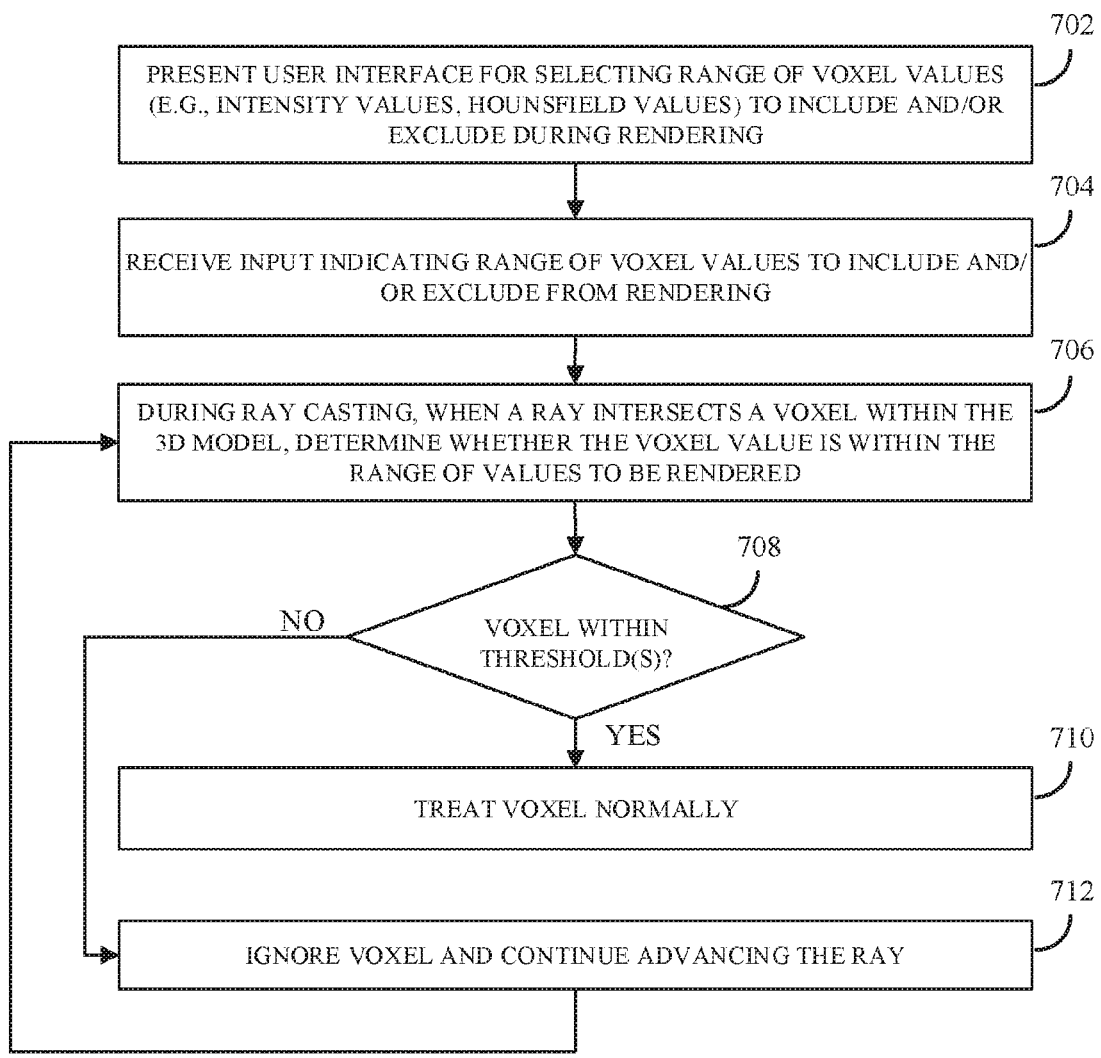
FIG. 7 shows an example 700 of a process for selectively presenting portions of medical imaging data in a 3D virtual environment in accordance with some embodiments of the disclosed subject matter.

FIG. 7 shows an example 700 of a process for selectively presenting portions of medical imaging data in a 3D virtual environment in accordance with some embodiments of the disclosed subject matter. As shown in FIG. 7, process 700 can begin at 702 by presenting a user interface for selecting a range of voxel values (e.g., intensity values, Hounsfield values, grayscale value, and/or any other suitable type of value) to include and/or exclude from being rendered. In some embodiments, process 700 can present any suitable user interface that can be used to select a range of voxel values to include/exclude when rendering the object from the 3D array of medical imaging data. For example, process 700 can present a user interface that includes sliders that are moveable along a bar to allow a user to select values to include in the 3D array of imaging data, and process 700 can receive input (e.g., at 704) regarding which values to include and/or exclude from rendering via the slider positions (e.g., as shown in FIG. 8B). As another example, process 700 can present a user interface that includes selectable presets (e.g., as software buttons) that correspond to types of anatomy, such as bone, lungs, etc. As yet another example, process 700 can present a user interface tool that can be used to select a portion of imaging data to include or exclude during rendering. In a more particular example, the user interface can include a pointer or volume selection tool that can be used to select a portion(s) of a scan (e.g., a surface area or volume) to include or exclude from rendering.

In some embodiments, process 700 can present multiple user interfaces to independently control filtering based on different criteria, which can be used in combination to affect which portions of the 3D array are rendered, and the appearance of the portions that are rendered. For example, the mechanisms described herein can be used to provide a user interface that facilitates control (based on the underlying value of the voxel) of the range of voxel values to include and/or exclude from rendering; and can be used to provide a user interface that facilitates mapping of voxel values to grayscale values to determine how each voxel is rendered. In a more particular example, one user interface (e.g., a range user interface) can be used to control an upper and/or lower display range that controls not only which voxel values can be used for rendering, but also causes grayscale values to be mapped to the voxel values within the range such that a voxel with a value equal to the lower end of the display range is rendered as though it were black (e.g., a grayscale value of 0) and a value equal to the upper end of the display range is rendered as though it were white (e.g., a grayscale value of 255 when using 8 bits to represent brightness)

At 704, process 700 can receive input indicating a range of voxel values to include and or exclude during rendering. In some embodiments, process 700 can receive the input using any suitable technique or combination of techniques. For example, process 700 can receive input as slide positions corresponding to values, a selection of a virtual button, and a selection of a volume or surface area that includes voxel values to include or exclude.

At 706, process 700 can, during ray casting (e.g., as described above in connection with FIG. 6), determine when a ray intersects a voxel included in the 3D array of medical imaging data, whether the voxel value is within the range of values to be rendered (or not rendered).

If process 700 determines that the voxel is within the threshold ("YES" at 708), process 700 can move to 710 and can treat the voxel normally (e.g., by determining whether the stopping condition for the ray is satisfied based on the value of the voxel).

Otherwise, if process 700 determines that the voxel is not within the threshold ("NO" at 708), process 700 can move to 712 to ignore the voxel, return to 706, and continue advancing the ray. For example, process 700 can base a determination of whether a stopping condition has been satisfied at 618 negatively when the voxel value is not within the threshold.

FIG. 8A1 shows an example 800 of a clip object intersecting a portion of a 3D model exposing medical imaging data at the boundary of the clip object including a portion of an anatomical structure having particular properties in accordance with some embodiments of the disclosed subject matter. As shown in FIG. 8A1, a structure 802 of the imaging data has different characteristics than the surrounding areas.

FIG. 8A2 shows an example 810 of a cross-section view of the object shown in FIG. 8A1 illustrating that there is a second anatomical structure within the 3D object that is not visible in FIG. 8A1 as no portion of the second anatomical structure intersects the boundary of the clip object in accordance with some embodiments of the disclosed subject matter. As shown in FIG. 8A2, a second anatomical structure 812 having similar characteristics to structure 802 is included within object 102, but is hidden within the exterior surface of object 102. Additionally, as shown in FIG. 8A2, a portion 814 of structure 802 is not being rendered due to the presence of clip object 202. FIG. 8A3 shows an example 820 of a 3D shape of anatomical structure 802 represented in FIGS. 8A1 and 8A2. FIG. 8A3 shows the general shape of structure 802 in the absence of other portions of object 102.

FIG. 8B shows an example of a user interface 850 that can be used to select portions of the medical imaging data to render and portions to medical imaging data to exclude from rendering in accordance with some embodiments of the disclosed subject matter. As shown in FIG. 8B, a slide bar 852 can be associated with sliders 854 and 856. As described above in connection with FIG. 7, slider bars 854 and/or 856 can be manipulated to filter the imaging data (e.g., based on intensity values). Additionally, in some embodiments, virtual buttons 860 that each correspond to a particular type of tissue (or other visualization), such as bone, soft tissue, a particular organ(s) such as the lungs, the liver, etc. In some embodiments, when a preset is selected by providing input to a virtual button of 860, sliders 854 and 856 can be adjusted to show the range of values that are being rendered.

FIG. 8C1 shows an example 860 of a clip object intersecting a portion of the 3D model shown in FIG. 8A1 with a filter applied that excludes medical imaging data other than medical imaging data having particular properties from being rendered exposing the two anatomical structures that are present within the 3D object but not rendered in accordance with some embodiments of the disclosed subject matter. As shown in FIG. 3C1, after a filter has been applied, all portions of the object being presented (e.g., object 102), other than the portions specifically included, are excluded and not rendered.

FIG. 8C2 shows an example 870 a cross-section view of the scene shown in FIG. 8C1 illustrating with a dotted line the extent of the 3D model that is being excluded from rendering based on the filter that has been applied in accordance with some embodiments of the disclosed subject matter. As shown in FIG. 8C2, portions of object 102 are not within the threshold are not rendered, which can expose both structures 802 and 812. In some embodiments, portions of structures 802 and 812 that do not intersect clip object 202 can be rendered normally (e.g., based on light sources, reflections, etc.) although the structure would normally not be exposed except by a clip object.

FIG. 8D shows an example of a portion of a 3D model based on a computed tomography scan in which a filter has been applied to exclude portions of the medical imaging data except portions of the data having properties representing bone presented within a virtual environment using a system configured in accordance with some embodiments of the disclosed subject matter. As shown in FIG. 8D, portions of the scan corresponding to bone are being rendered based on a threshold selection corresponding to bone, with a clip object exposing the interior of some portions of the remaining bone structure. In some embodiments, the filter can be applied regardless of whether the ray intersects the object within the clip object, such that interior values that are not within the threshold (e.g., bone marrow in the example of FIG. 8D) are not displayed. Alternatively, in some embodiments, the filter can be applied differently based on whether the ray intersects the object within the clip object such that some portions of the 3D array that are filtered outside the clip object are shown within the clip object.

FIG. 8E shows an example of a portion of a 3D model based on a computed tomography scan in which a filter has been applied to exclude portions of the medical imaging data except areas having properties representing blood vessels presented within a virtual environment using a system configured in accordance with some embodiments of the disclosed subject matter. As shown in FIG. 8E, a clip object exposes the interior of a skull in the medical imaging data, and the threshold has been set to include blood vessels, but to exclude other soft tissue (e.g., brain matter).

Figure 9:
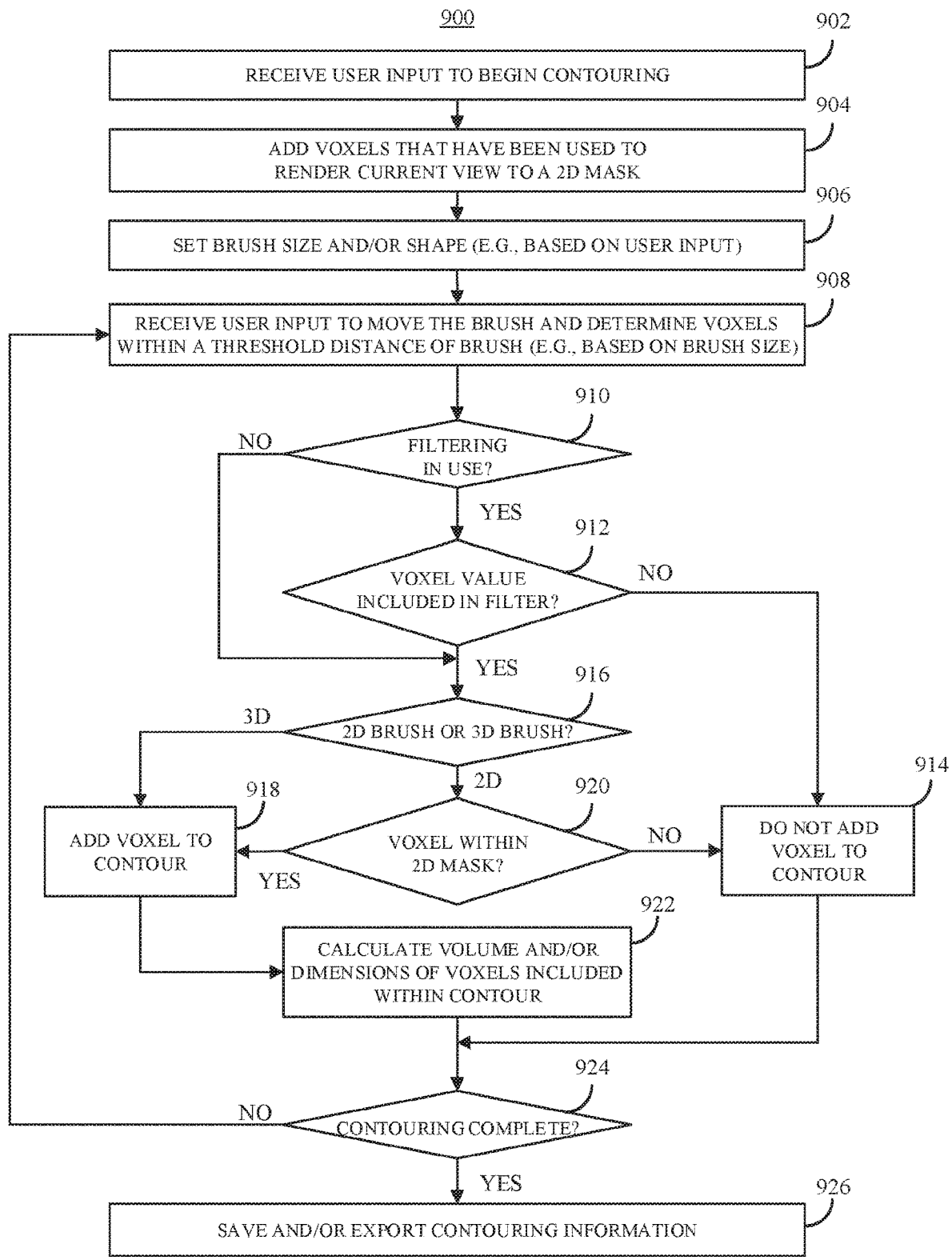
FIG. 9 shows an example 900 of a process for segmenting portions of medical imaging data represented as a 3D model in a virtual environment in accordance with some embodiments of the disclosed subject matter.

FIG. 9 shows an example 900 of a process for segmenting portions of medical imaging data represented as a 3D model in a virtual environment in accordance with some embodiments of the disclosed subject matter. As shown in FIG. 9, process 900 can begin, at 902, by receiving input indicating that a user wishes to enter a contouring (alternatively, sometimes referred to as segmentation) mode in which one or more portions of the 3D array imaging array can be highlighted. For example, in some embodiments, a user may wish to highlight areas of the imaging data that correspond to a particular organ, a particular portion of tissue that is to be removed, a portion of tissue corresponding to a tumor, etc. In some embodiments, such input can be provided using any suitable technique or combination of techniques. For example, in some embodiments, a user input device (e.g., user input device 404) can have a dedicated user interface element (e.g., a hardware or software button) that causes process 900 to be initiated. In such an example, a user can adjust a position of a user interface element (e.g., a brush) to a particular position before initiating the contouring operation, and can initiate contouring by actuating the button. As another example, in some embodiments, process 900 can be initiated when the user performs one or more gestures associated with a command to initiate contouring. In such an example, the gestures can include moving a user input device (e.g., user input device 204) and/or one or more body parts of the user in a particular pattern. As yet another example, in some embodiments, the user input can be provided via a user interface element presented as part of a graphical user interface presented within the virtual environment (e.g., as an icon, as an entry in a menu, etc.). As still another example, a voice command can be received to initiate contouring.

In general, contouring or segmentation involves identifying structures on medical images, which may be normal anatomy, areas of disease, areas at risk of disease spread, or synthetic regions used to assist in planning therapy (e.g. regions to preferentially avoid with radiation therapy beams). Conventionally contouring techniques are performed in two dimensions, using tools that allow a user to outline or "paint" an area on a single plane of image data (typically along the axial, coronal, or sagittal plane). A user must perform this process on multiple serial slices to delineate a 3D volume. As described below, the mechanisms described herein can use a different approach that allows a user to draw contours in a fully 3D environment. For example, using 6 DOF tracking in combination with rendering techniques described herein (e.g., as described above in connection with FIG. 6).

At 904, process 900 can add (or maintain) voxels in the 3D array of medical imaging data that have been used to render the current view of the 3D array of medical imaging data to a 2D mask. In some embodiments, the 2D mask can be generated in cases when a 2D brush is being used, and can be omitted when a higher dimensionality brush is being used.

At 906, process 900 can set a brush size, shape, and/or dimensionality. In some embodiments, process 900 can set the brush size, shape, and/or dimensionality using any suitable technique or combination of techniques. For example, in some embodiments, process 900 can set size, shape, and/or dimensionality of the brush to default values. As another example, in some embodiments, process 900 can set the size, shape, and/or dimensionality of the brush to previously set values (e.g., values used during a previous contouring operation). As yet another example, in some embodiments, process 900 can set the size, shape, and/or dimensionality of the brush based on user input received to initiate process 900 (e.g., different user interface elements can be provided for initiating a contouring operation using a 2D brush versus a 3D brush, different user interface elements can be provided initiating a contouring operation using different sized brushes, etc.). As still another example, in some embodiments, process 900 can set the size, shape, and/or dimensionality of the brush based on user input received after initiation of process 900.

In some embodiments, the size of the brush can be adjusted to any suitable size, which can be defined based on absolute dimensions (e.g., based on a dimension that does not change with changes in the size at which the 3D array is rendered), or in relative dimensions (e.g., based on the dimensions of a voxel of the 3D array).

In some embodiments, the shape of the brush can be adjusted to any suitable shape. For example, the brush can have a spherical shape, a cubic shape, a conical shape, a cylindrical shape, etc.

In some embodiments, the dimensionality of the brush can be set to act on any suitable number of dimensions. For example, in some embodiments, the brush can be set to interact with only the visible surface, which is sometimes referred to as a 2D brush. As another example, in some embodiments, the brush can be set to interact with voxels that are not being rendered, such as voxels that are behind the surface from the point of view of the user, which is sometimes referred to as a 3D brush. As yet another example, in some embodiments, the brush can be set to interact with voxels having particular properties other than a location within the brush. In such an example, the brush can be set to interact with only voxels that have a particular property (e.g., an intensity within a specified range, a T1 value within a specified range, etc.). Additionally, in some embodiments, the brush can be set to interact with voxels only when at least a portion of the brush intersects a visible surface (e.g., an exterior surface rendered using shading, or an interior surface exposed at the boundary of a clip object), which is sometimes referred to herein as plane based contouring. Alternatively, in some embodiments, the brush can be set to interact with voxels regardless of whether the brush intersects a rendered surface (e.g., the brush can be entirely within the clip object or entirely within the 3D model), which is sometimes referred to herein as free contouring. In some embodiments, the mechanisms described herein can provide a user interface that allows a user to select plane-based or free contouring.

At 908, process 900 can receive user input to place the brush at a particular position, and process 900 can determine which voxels of the 3D array of medical imaging data are within a threshold distance of the brush. For example, if the brush is a sphere with a diameter equal to six voxels (at the size the voxels are currently being rendered), process 900 can determine which voxels (if any) are within a three voxels of the center of the brush.

In some embodiments, as a user moves the brush (whether contouring is currently being performed, or the user is merely positioning the brush without actively contouring the image data) process 900 can cause haptic feedback to be provided that can be indicative of one or more properties of a voxel nearest the center of the brush, multiple voxels that fall within the brush volume, and/or voxels that are within a threshold distance outside the brush volume. For example, haptic feedback can be provided based on the intensity value of a voxel nearest the center of the brush, or based on the average intensity value of all voxels within the brush. In such an example, the haptic feedback can be scaled based on the intensity value (e.g., higher intensity can correspond to more feedback), or based on the change in intensity value (e.g., whether the intensity is increasing or decreasing can be conveyed by providing different types and/or intensities of haptic feedback).

In some embodiments, other portions of a scene can be moved during movement of the brush, which can facilitate more complex, but potentially more efficient contouring techniques. For example, in some embodiments, a clip object can be moved in concert with the brush to continually expose a different portion of the 3D array of medical imaging data. In such an example, the clip object can be anchored to the brush such that the clip object moves with the brush without specific user intervention causing the clip object to move. Alternatively, in such an example, the clip object can be moved using a first user input device (e.g., operated with a first hand), while the brush is moved using a second user input device (e.g., operated using the user's other hand).

At 910, process 900 can determine whether a filter is being applied during rendering to present one or more portions of the 3D array of medical imaging data while excluding one or more other portions of the 3D array of medical imaging data (e.g., as described above in connection with FIG. 7).

If process 900 determines that a filter is being applied ("YES" at 910), process 900 can move to 912 to determine whether each of the voxel falls within the filter. For example, if the filter is set to include portions corresponding to bone by including only voxels with a Hounsfield value within a specified range, process 900 can determine whether the Hounsfield value of each voxel within the threshold distance is also within the specified range. In some embodiments, using the filter techniques described above in connection with FIG. 7 in combination process 900 can, for example, apply upper and lower thresholds to voxel values to be included in the contour, and when the brush is used, the voxels of the 3D array of medical imaging data within the threshold distance of the brush can be evaluated, and only voxels within the 3D volume of the brush which also fall within the threshold range of the displayed volume rendering can be included in the contour. This can allow a user to perform contouring operations that are not possible with conventional techniques. For example, a user can adjust thresholds until they can visualize specific features of interest (e.g. bones, blood vessels with contrast or wires marking a catheter, etc.), and can confidently contour those features being rendered without being concerned with including adjacent voxels that correspond to other portions of anatomy by visually confirming whether the anatomy being displayed corresponds to the anatomy that the user wants to contour (as voxels that fall outside the threshold can be excluded from rendering, and hence can be guaranteed to not be contoured). This has the potential to greatly increase the speed and precision of these tasks, since these features typically do not fall along a planar surface.

If process 900 determines that a particular voxel is within the range ("YES" at 912), or if process 900 determines that a filter is not being applied ("NO" at 910), process 900 can move to 916. Otherwise, if 900 determines that a particular voxel is not within the range ("NO" at 912), process 900 can move to 914, and can exclude the voxel from being included in the contour being drawn.

At 916, process 900 can determine whether the brush is a 2D brush or a 3D brush. If process 900 determines that the brush is a 3D brush ("3D" at 916), process 900 can move to 918, and can add the voxel to the contour. In some embodiments, the contour can be a particular color, such that the portion of the imaging data corresponding to the contour can be easily identified based on color, and can be easily distinguished from other portions of the imaging data (e.g., which are depicted in grey scale and/or are contoured using a different color). Alternatively, in some embodiments, portions of the imaging data can be associated with a "clear" or resection contour that causes the contoured voxels to be omitted during rendering (e.g., as shown in, and described in connection with FIG. 10E below). In some embodiments, the segmentation can be implemented as a binary mask that indicates which voxels within the 3D array are part of the segmentation, and which are not.

In some embodiments, the mechanisms described herein can provide a user interface to allow a user to control how each contour is presented during rendering. For example, in some embodiments, the mechanisms described herein can provide a user interface that allows a user to select a color to use to draw a new contour, and/or can change the color of an existing (e.g., previously drawn and/or imported) contour. As another example, in some embodiments, the mechanisms described herein can provide a user interface that allows a user to set the transparency of one or more contours (e.g., individually and/or as a group of two or more, up to all contours). As yet another example, in some embodiments, the mechanisms described herein can provide a user interface that allows a user to toggle presentation of one or more contours to cause presentation to be enabled or disabled, respectively.

Otherwise, if process 900 determines that the brush is a 2D brush ("2D" at 916), process 900 can move 920. At 920, process 900 can determine whether each voxel within the brush is also present in the 2D mask of voxels that are currently being used to render a surface of a 3D model based on the 3D array of medical imaging data. In some embodiments, when rendering a scene, voxels can be drawn based on ray casting that is constrained by specified criteria (e.g., whether the voxel is within a grey-level/Hounsfield unit threshold as well as whether it is beyond a "clip object"). In some such embodiments, a GPU executing at least a portion of process 900 can record which voxels have been drawn in the rendering as a binary mask in a buffer of the GPU. When using a 2D contouring brush, a user can provide input to initiate a contouring operation (e.g., as described above in connection with 902) by presses a button to draw part of a contour, and the voxels within the bounds of the brush-tip contour can be used to query the GPU buffer to determine if those voxels are also part of the mask of drawn voxels. In some such embodiments, only voxels which satisfy both of these conditions (e.g., as described in connection with 908 and 920) cab be included in the contour. This is distinct from conventional 2D contouring, in that the 2D brush can be used to draw a contour on an arbitrary non-planar surface defined by a clip object, or even on a hybrid view in which some voxels fall on the surface of a clip object, and some are rendered using ray casting techniques deeper within the object.

If process 900 determines that a particular voxel is present in the 2D mask ("YES" at 920), process 900 can move to 918 to add the voxel to the contour. Otherwise, if process 900 determines that a particular voxel is not present in the 2D mask ("NO" at 920), process 900 can move to 914 to exclude the voxel from being included in the contour being drawn.

After adding voxels that are within the brush, and that meet any other criteria being applied (e.g., at 910, 912, 916, and/or 920), process 900 can move to 922 to calculate the volume and/or dimensions of the voxels included within the contoured region. In some embodiments, process 900 can use any suitable technique or combination of techniques to determine the volume and/or dimensions of the contoured region. For example, process 900 can count the number of whole voxels and/or fractions of voxels included in the volume and/or along a particular dimension. In such an example, process 900 can determine the volume or dimension based on the size of the voxel (e.g., if the region includes n voxels that are each x×y×z mms, the volume can be calculated by multiple the volume of each voxel by the number of voxels).

In some embodiments, process 900 can determine a length of a path drawn within the image, whether the path is used to produce a contour or not. For example, a user can trace a curve through the 3D array of medical imaging data as rendered using the mechanisms described herein, and process 900 can determine the distance along the curve. In some embodiments, a curve can be represented as a series of connected line segments that can be joined at arbitrary angles. In some such embodiments, process 900 can calculate the distance along the curve by summing the length of each line segment. For example, a user can trace the contour of a non-planar portion of anatomy (e.g., the shape of a particular muscle, the curved surface of a portion of the stomach, etc.), and process 900 can calculate the distance along the curve for presentation to the user. In some embodiments, a user (e.g., a physician) can use the distance along the curve to inform treatment decisions, such as a target volume for radiation therapy. For example, a physician can draw a curve of known length along a particular anatomical tract or plane at risk based on clinical guidelines related to how disease is likely to spread (e.g., indicating that the disease is likely to spread up to 2 cm). In such an example, the physician can use the dimensions of the curve to calculate a target volume for treatment (or resection) by matching a dimension of the target volume to the straight line distance between the end points of the curve. Using only planar views of the same scan, a physician may not be able to accurately measure a particular distance (e.g., 2 cm) along a curved surface, and accordingly may over (or under) estimate the target volume based on the imprecision of the measurement.

At 924, process 900 can determine whether a contouring operation has been completed using any suitable technique or combination of techniques. For example, process 900 can receive input indicating that the contouring operation has ended, such as an explicit input to cease such an operation, input to enter a different mode, etc.

If process 900 determines that the contour operation has not ended ("NO" at 924), process 900 can return to 908 to continue to receive user input to change the position of the brush. Otherwise, if process 900 determines that the contour operation has ended ("YES" at 924), process 900 can move to 926 to save and/or export the contouring information for later use in connection with one or more portions of the imaging data that makes up the 3D array of medical imaging data.

FIG. 10A1 shows an example 1000 of a clip object intersecting a portion of a 3D model exposing medical imaging data at the boundary of the clip object including a portion of an anatomical structure of interest to be segmented in accordance with some embodiments of the disclosed subject matter. As shown in FIG. 10A1, a structure 1002 of the imaging data is apparent within object 102 at the boundary of clip object 202.

FIG. 10A2 shows an example 1010 of a cross-section view of the object shown in FIG. 10A1 illustrating that, although a 2D cross section of the anatomical structure of interest is shown in FIG. 10A1 at the boundary of the clip object, the full three dimensional extent of the anatomical structure of interest is represented in the medical imaging data that is not rendered in the example shown in FIG. 10A1 in accordance with some embodiments of the disclosed subject matter. As shown in FIG. 10A2, structure 1002 extends beyond the portion visible at the boundary of clip object 202, but that portion is hidden within the exterior surface of object 102. Additionally, as shown in FIG. 10A2, a portion 1012 of structure 1002 is not being rendered due to the presence of clip object 202.

FIG. 10B1 shows an example 1020 of a user interface element representing a user input device that can be used to select portions of the medical imaging data to be segment with a 3D virtual brush presented in a defined position with respect to the user interface element in accordance with some embodiments of the disclosed subject matter. As shown in FIG. 10B1, a representation 1022 of a user input device (e.g., user input device 404) can be rendered in the scene with object 102. A brush 1024 is shown in a location overlapping the surface of structure 1002 that is exposed by clip object 202 (e.g., as shown in FIG. 10A1, which is omitted from FIG. 10B1 to simplify the depiction of other features of the mechanisms described herein). Note that, as shown in FIG. 10B1, representation 1022 can be associated with a user interface element (e.g., shown as a triangle in FIG. 10B1) that can be used to illustrate a location of at which an action can be taken with the user interface element (e.g., in a manner similar to a mouse cursor displayed on a 2D user interface).

FIG. 10B2 shows an example 1030 of a cross-section view of a portion of the object shown in FIG. 10B1 illustrating that the 3D brush can extend past the portion of the medical imaging data being rendered in accordance with some embodiments of the disclosed subject matter. As shown in FIG. 10B2, brush 1024 can extend beyond the surface presented at the boundary of the clip object. As described above in connection with FIG. 9, brush 1024 can be implemented as a 2D brush that only draws on voxels that are currently being rendered, and can also be implemented as a 3D brush that draws all voxels within the brush (e.g., which may be augmented by one or more criteria, such as an intensity threshold(s)).

FIG. 10C1 shows an example 1040 of the object shown in FIG. 10A1 with a portion of the anatomical structure of interest segmented in response to movements of the 3D brush in relation to the 3D model in accordance with some embodiments of the disclosed subject matter. As shown in FIG. 10C1, by moving a user input device corresponding to representation 1022 (e.g., as shown by the arrow within structure 1002 in FIG. 10B1), a portion of object 102 can be associated with a contour 1042 (shown with rectangular cross hatching). As described above, if brush 1024 is a 2D brush, only voxels corresponding to the portion of structure 1002 that is being rendered can be associated with contour 1042. Alternatively, in some embodiments, if brush 1024 is a 3D brush, voxels that extend above and/or below the surface being rendered can be included in contour 1042. For example, FIG. 10C2 shows an example 1050 of a cross-section view of a portion of the object shown in FIG. 10C1 illustrating that the portions of the medical imaging data that are segmented can extend past the portion of the data being rendered in accordance with some embodiments of the disclosed subject matter. As shown in FIG. 10C2, contour 1042 includes voxels that are not currently being rendered because the voxels are within object 102 or because the voxels are within clip object 202.

Figure 10D:
FIG. 10D shows an example of a portion of a 3D model based on a magnetic resonance imaging scan in which a user interface element is being used to segment a portion of the radiological data presented within a virtual environment using a system configured in accordance with some embodiments of the disclosed subject matter.

FIG. 10D shows an example of a portion of a 3D model based on a magnetic resonance scan in which a user interface element is being used to segment a portion of the medical imaging data presented within a virtual environment using a system configured in accordance with some embodiments of the disclosed subject matter. As shown in FIG. 10D, a brush is being manipulated to segment a portion of a 3D image array depicting the brain of a subject.

Figure 10E:
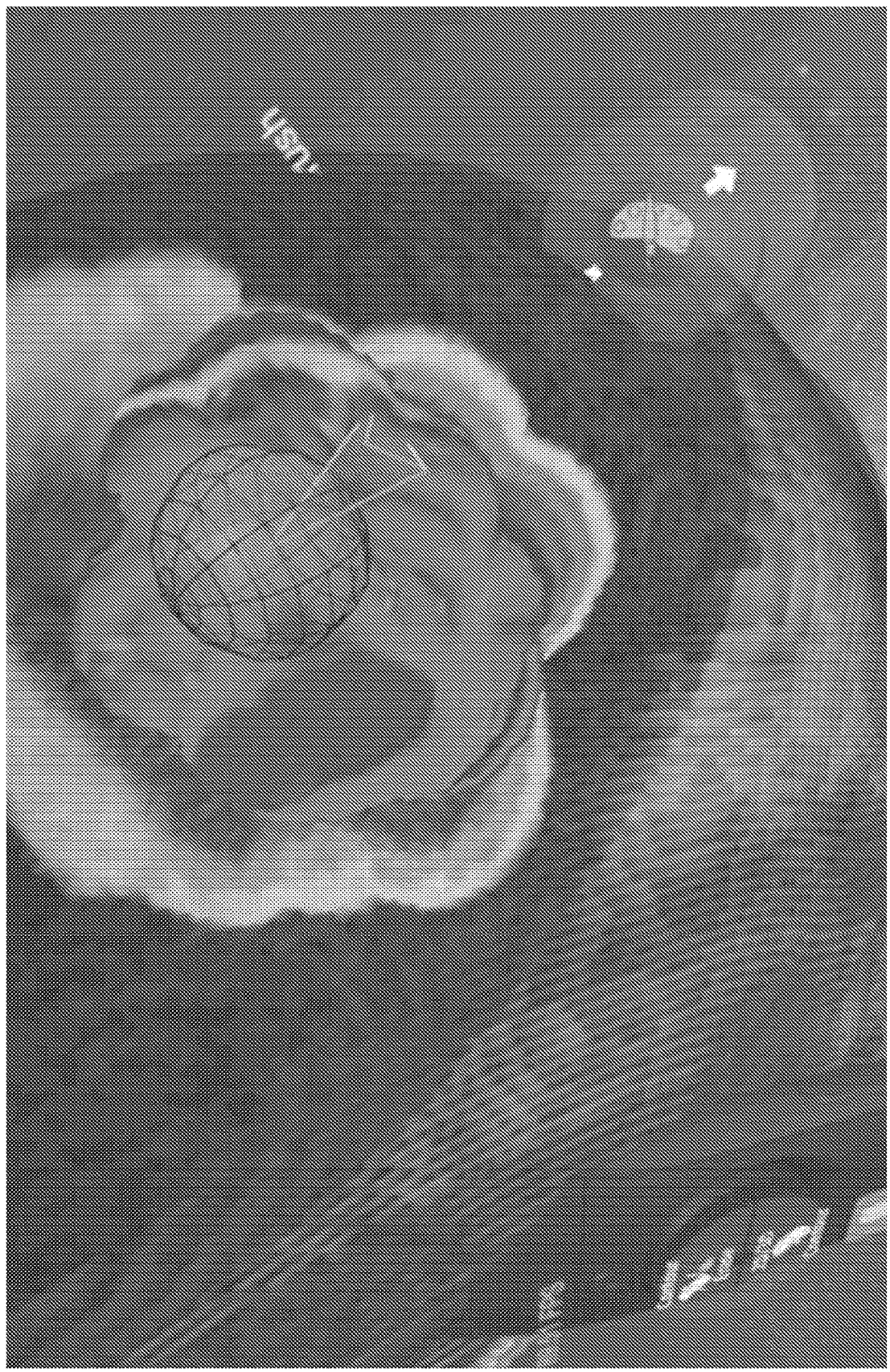
FIG. 10E shows an example of a portion of a 3D model based on a magnetic resonance imaging scan in which a user interface element is being used to virtually resect portions of the 3D model presented within a virtual environment using a system configured in accordance with some embodiments of the disclosed subject matter.

FIG. 10E shows an example of a portion of a 3D model based on a magnetic resonance scan in which a user interface element is being used to virtually resect portions of the 3D model presented within a virtual environment using a system configured in accordance with some embodiments of the disclosed subject matter. As shown in FIG. 10E, a brush is being manipulated to mark portions of a 3D array of medical imaging data for omission during rendering. In some embodiments, this can be used to perform a virtual resection. In some embodiments, as described above in connection with FIG. 6, the mechanisms described herein can create a shader-based representation of a 3D array of medical imaging data in a virtual environment, which can facilitate a virtual "surgical resection" over a medical imaging scan. For example, using techniques described above in connection with FIG. 9, a binary mask can be created that represents the voxels within a contoured volume. In such an example, for virtual surgical resections, this voxel mask can be passed to the shader, and can be used as an additional constraint to determine whether a voxel is rendered. Accordingly, using these techniques can allow for drawn contours to function as a virtual resection, allowing a user to plan a surgical approach using the mechanisms described herein. Such a "surgical planning segmentation" can be manipulated in the same way that standard contouring segmentations are manipulated (e.g., by adding, subtracting, interpolating, thresholding, etc.) and can be exported for intraoperative use and/or guidance, for the comparison of multiple surgical plans, and/or for any other suitable purposes.

Figure 11:
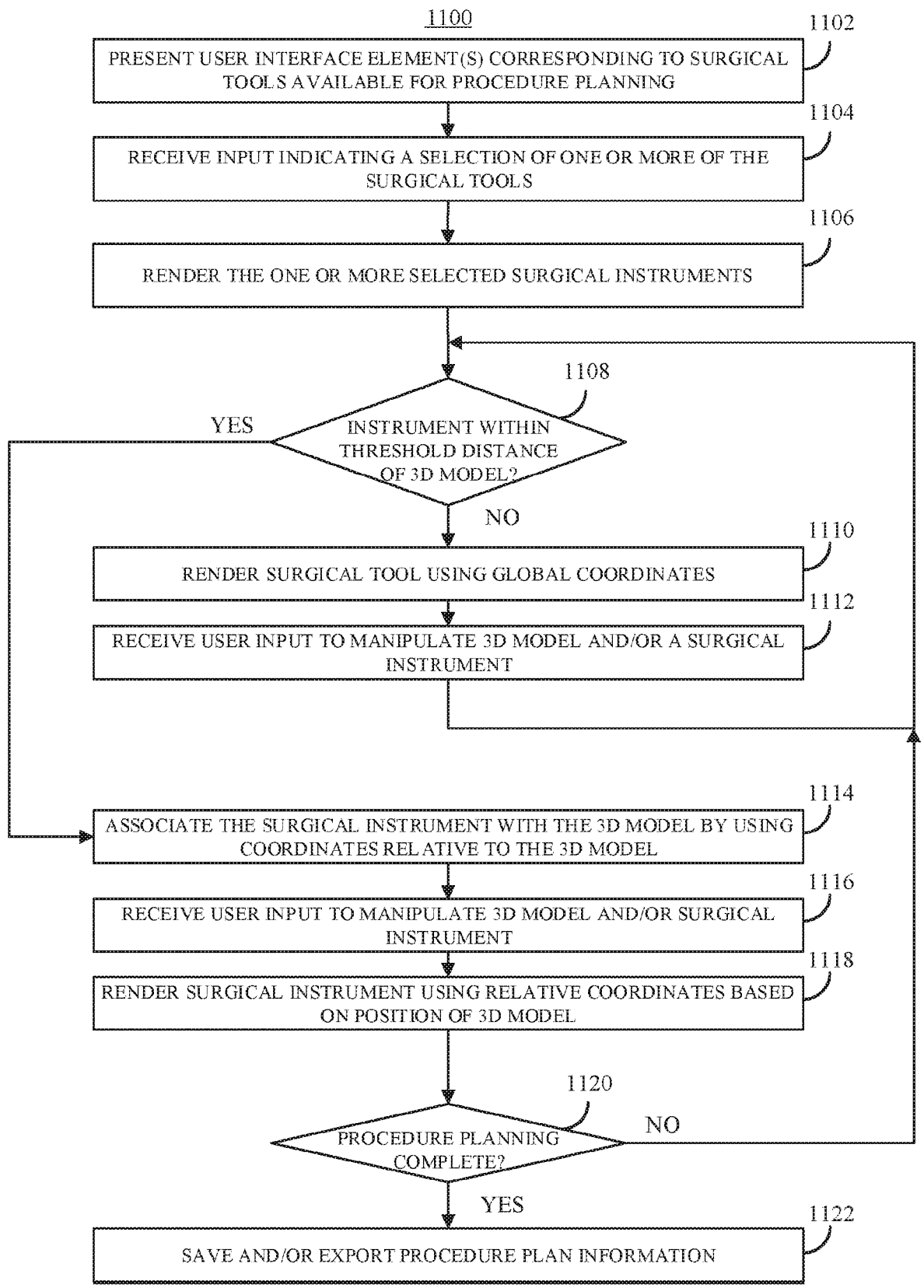
FIG. 11 shows an example 1100 of a process for planning a surgical intervention using a 3D model based on a radiological scan of a subject in a virtual environment in accordance with some embodiments of the disclosed subject matter.

FIG. 11 shows an example 1100 of a process for planning a surgical intervention using a 3D model based on a radiological scan of a subject in a virtual environment in accordance with some embodiments of the disclosed subject matter. As shown in FIG. 11, process 1100 can begin, at 1102, by presenting selectable user interface elements corresponding to various surgical planning instruments that can be used to plan a surgical intervention. In some embodiments, representations of any suitable surgical instruments can be made available for planning a surgical intervention using mechanisms described herein. For example, in some embodiments, the user interface for selecting a surgical instruments can include representations of: biopsy needles (e.g., for percutaneous lung biopsy) and/or other biopsy tools; shunts (e.g., a ventriculoperitoneal shunt); implantable medical devices (e.g., a deep brain stimulation lead, an implanted defibrillator, etc.); surgical staple devices, clip application devices, cautery, suturing tools, intra-arterial catheters, intraoperative imaging devices, etc.

In some embodiments, process 1100 can present one or more selectable user interface items for other types of objects that can be associated with the 3D model. For example, in some embodiments, process 1100 can present a selectable user interface element that allows a user to place a marker that can be labeled to identify a particular portion of anatomy. In a more particular example, as described below in connection with FIG. 12D, process 1100 can present a user interface element that, when selected, allows a user to place a virtual pin that can be associated with a label to semantically identify a particular portion of the virtual environment (e.g., a particular segmentation).

In some embodiments, process 1100 can present the user interface using any suitable technique or combination of techniques. For example, process 1100 can present a hierarchical menu lists of available instruments organized in a hierarchy (e.g., based on the type of device, the purpose of the device, etc.).

At 1104, process 1100 can receive input indicating a selection of one or more of the surgical instruments. In some embodiments, such input can be provided using any suitable technique or combination of techniques. For example, in some embodiments, a user input device (e.g., user input device 404) can have a dedicated user interface element (e.g., a hardware or software button) that can be used to select a presented user interface element (e.g., a user interface element corresponding to a menu item, a user interface corresponding to a particular surgical instrument, etc.) when a representation of the user input device is within a threshold distance of the user interface element. In such an example, a user can adjust a position of a user interface element (e.g., a virtual pointer) to a particular position corresponding to the user interface element to be selected, and can initiate selection by actuating the button. As another example, in some embodiments, a selection can be initiated when the user performs one or more gestures associated with a command to select a particular user interface element (e.g., causing a representation of the user input device to actuate a software button presented within the virtual environment without the user actuating a physical button on the user input device). As yet another example, a voice command can be received to select one or more surgical instruments.

At 1106, process 1100 can render the one or more surgical instruments that have been selected at a size scaled based on the size of a 3D model rendered from the 3D array of medical imaging data. For example, process 1100 can determine the dimensions of a selected biopsy needle, and can render the biopsy needle at the same scale as the 3D model currently being rendered. In such an example, this can facilitate use of the surgical instrument for planning a surgical intervention, as the instrument's size relative to the subject's anatomy presented in the virtual environment can be expected to correspond to the actual sizes of the instrument and the subject's anatomy.

At 1108, process 1100 can determine if one or more of the rendered surgical instruments are within a threshold distance of the 3D model. In some embodiments, process 1100 can use any suitable threshold to determine whether to use absolute or relative coordinates when rendering the surgical instrument. For example, process 1100 can determine if any portion of the surgical instrument overlaps the 3D array of imaging data and/or a bounding box associated with the 3D array of imaging data. As another example, process 1100 can determine if any portion of the surgical instrument is within a threshold distance of any voxel from the 3D array, such as a distance corresponding to a real-world distance of 10 centimeters, one quarter of a meter, one half of a meter, etc.

If process 1100 determines that the surgical instrument is not within the threshold ("NO" at 1108), process 1100 can move to 1110, and can render the surgical instrument using global coordinates to determine where in the virtual environment to present the surgical instrument. For example, a user can manipulate the position of the virtual instrument, at 1112, within the virtual environment, and process 1100 can track the position of the virtual surgical instrument based on coordinates defining the extent of the virtual environment.

In some embodiments, after rendering the surgical instrument at 1110, process 1100 can continue to receive user input, at 1112, to manipulate the 3D model and/or virtual surgical instrument within the virtual environment. In some such embodiments, after user input is received, process 1100 can return to 1108 to determine whether the instrument is within the threshold distance. In some embodiments, while the user is manipulating the virtual surgical instrument, process 1100 can associate the virtual surgical instrument with the user input device that is being used to provide user input to manipulate instrument (e.g., while the user is "holding" the virtual instrument) such that the position and orientation is rendered based on the relative position of the instrument to the user input device. In some such embodiments, when the user stops manipulating the position of the surgical instrument (e.g., the user "let's go" of the surgical instrument) process 900 can determine whether to use global coordinates or relative coordinates based on whether the instrument is within the threshold distance of the 3D model at 1108.

If process 1100 determines that the surgical instrument is within the threshold ("YES" at 1108), process 1100 can move to 1114, at which process 1100 can associate the surgical instrument with the object. For example, in some embodiments, the surgical tool can be designated as being a child of the object, and the coordinates can be adjusted to reflect the change in coordinate system.

At 1116, process 1100 can receive user input to manipulate the 3D model and/or virtual surgical instrument within the virtual environment, and can render, at 1118, the surgical instrument based on the relative coordinates of the surgical instrument after any manipulation at 1116. For example, if the user manipulates the position and/or orientation of the surgical instrument, process 1100 can update the relative coordinates of the surgical instrument by determine the change or position and/or orientation with reference to the 3D model. As another example, if the user manipulates the position and/or orientation of the 3D model, process 1100 can update the coordinates of the 3D model, which can be automatically propagated to the surgical instrument based on the association between the 3D model and the surgical instrument.

In some embodiments, as a user moves a virtual surgical instrument, process 1100 can cause haptic feedback to be provided that can be indicative of one or more properties of a voxel(s) through which one or more points on the surgical instrument is being moved. For example, haptic feedback can be provided based on the intensity value of a voxel that the tip of a biopsy needle encounters as the virtual biopsy needle is moved through the scan. In such an example, the haptic feedback can be scaled based on the intensity value (e.g., higher intensity can correspond to more feedback), or based on the change in intensity value (e.g., whether the intensity is increasing or decreasing can be conveyed by providing different types and/or intensities of haptic feedback). In some embodiments, process 1100 can provide haptic feedback when voxels with particular properties are encountered (e.g., voxels corresponding to blood vessels, voxels within a threshold distance of a blood vessel, voxels corresponding to bone, etc.).

At 1118, process 1100 can render the surgical instrument using the relative coordinates based on the position and orientation of the 3D array of medical imaging data to determine where in the virtual environment to present the surgical instrument. For example, as described below in connection with FIGS. 12A and 12B, the position and orientation of the surgical instrument can be defined with reference to the center of the 3D model as a reference point (e.g., an origin in a local coordinate system), rather than using a global origin to define the position and/or orientation of the object being rendered.

At 1120, process 1100 can determine whether a surgical planning operation has been completed using any suitable technique or combination of techniques. For example, process 1100 can receive input indicating that the surgical planning operation has ended, such as an explicit input to cease such an operation, input to enter a different mode, etc.

If process 1100 determines that the surgical planning operation has not ended ("NO" at 1120), process 1100 can return to 1108 to continue to receive user input to determine whether a virtual instrument is within a threshold distance of the object. Otherwise, if process 1100 determines that the surgical planning operation has ended ("YES" at 1120), process 1100 can move to 1122 to save and/or export the surgical planning information for later use in connection with one or more portions of the imaging data that makes up the 3D array of medical imaging data. In some embodiments, when a surgical planning operation has been completed, one or more portions of a plan (e.g., an angle and location of entry of a biopsy needle in coordinates based on the 3D array of medical imaging data) can be saved and/or exported for use in additional planning and/or for use during the intervention.

In some embodiments, the mechanisms described herein, including techniques described in connection with FIGS. 11, 12A and 12B, can facilitate for the use of virtual surgical instruments to plan an interventional or surgical approach. For example, a virtualized biopsy needle can be manipulated in 6 DOF relative to a patient's scan, and can be placed in the scan of the patient to ensure that the planned approach does not cause risk of critical structures, and/or could be technically successful (e.g., by reaching the tissue to be biopsied). As another example, an aneurysm clip application system can be virtualized to determine if removing certain tissue (e.g., via a surgical resection contour described above in connection with FIG. 9) would allow adequate exposure for clip application. Use of these techniques can facilitate preplanning of complex interventional procedures and/or surgical operations, which may decrease the need to modify operative plans at the time of actual procedure (e.g., when unexpected anatomical features are encountered), which may also facilitate safer interventions that produce less complications.

Figure 12A:
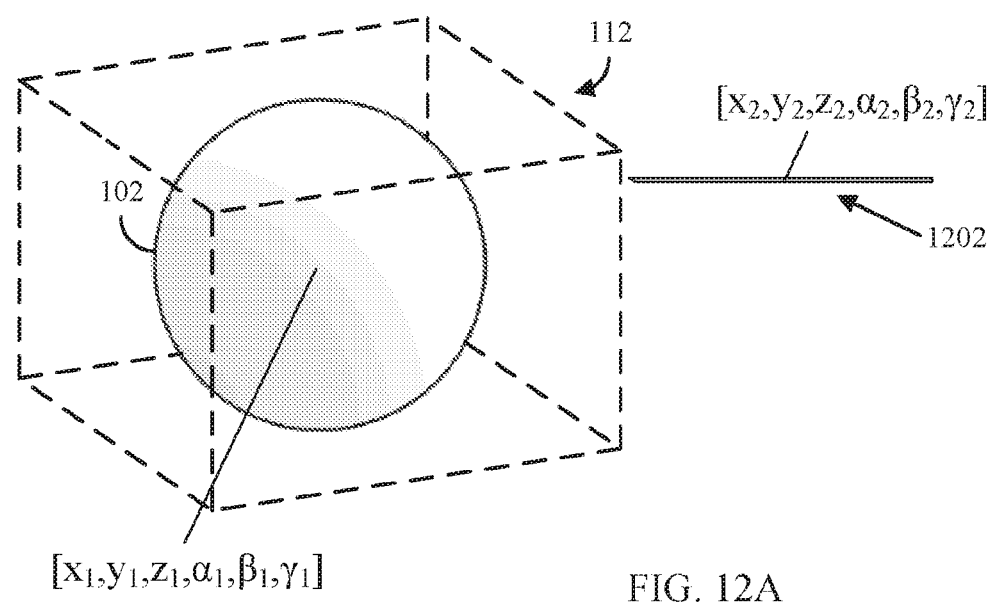
FIG. 12A shows an example 1200 of a 3D model representing a portion of a subject and a virtual surgical tool presented within a virtual environment that can be used to plan a surgical intervention in accordance with some embodiments of the disclosed subject matter.

FIG. 12A shows an example 1200 of a 3D model representing a portion of a subject and a virtual surgical tool presented within a virtual environment that can be used to plan a surgical intervention in accordance with some embodiments of the disclosed subject matter. As shown in FIG. 12A, global coordinates can be used to described the location of a virtual biopsy needle 1202 that is not within a threshold distance of object 102 (e.g., not intersection object 102, not intersecting bounding box 112, etc.). For example, as shown in FIG. 12A, the location and orientation of object 102 can be described using six values to represent the location and orientation of object 102. These values can include lateral values (e.g., describing the position along the X and Y axes), a depth value (e.g., describing the position along the Z axis), a yaw value describing rotation of the object around a first axis (e.g., the Z axis), a pitch value describing rotation of the object around a second axis (e.g., the Y axis), and a roll value describing rotation of the object around a third axis (e.g., the X axis). As described herein, the position and orientation of an object (e.g., object 102, biopsy needle 1202, etc.) is sometimes denoted using x to refer to position along the X axis, y to refer to position along the Y axis, z to refer to a position along the Z axis, $\alpha$ to refer to a rotation around the Z axis, $\beta$ to refer to a rotation around the Y axis, and $\gamma$ to refer to a rotation around the X axis. For example, as shown in FIG. 12A, the position/orientation of object 102 is denoted as $[x_1, y_1, z_1, \alpha_1, \beta_1, \gamma_1]$, and the position of biopsy needle 1202 is denoted as $[x_2, y_2, z_2, \alpha_2, \beta_2, \gamma_2]$.

Figure 12B:
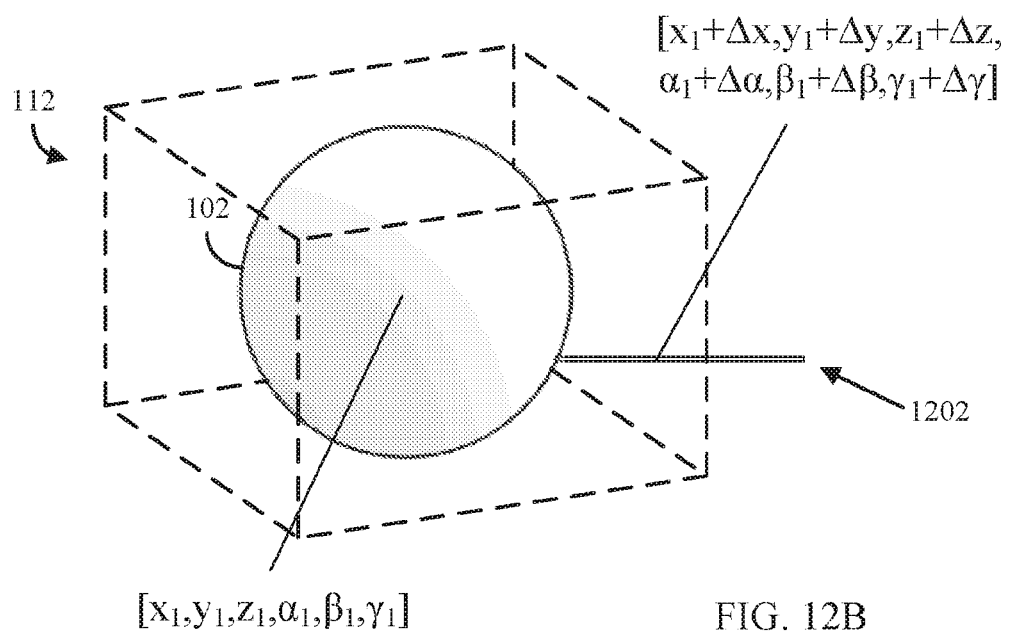
FIG. 12B shows an example 1220 of the 3D model and virtual surgical tool presented within the virtual environment using relative coordinates to define the location of the virtual surgical tool in relation to the 3D model in in accordance with some embodiments of the disclosed subject matter.

FIG. 12B shows an example 1220 of the 3D model and virtual surgical tool presented within the virtual environment using relative coordinates to define the location of the virtual surgical tool in relation to the 3D model in in accordance with some embodiments of the disclosed subject matter. As shown in FIG. 12B, when biopsy needle 1202 is within a threshold distance of object 102, the mechanisms described herein can define the position and/or orientation of biopsy needle 1202 using both the position of object 102 in global coordinates, and the position and orientation of biopsy needle 1202 using the position and orientation of object 102 to define a frame of reference. For example, as shown in FIG. 12B, the position/orientation of object 102 is still denoted as $[x_1, y_1, z_1, \alpha_1, \beta_1, \gamma_1]$, but the position of biopsy needle 1202 is now denoted as $[x_1+\Delta x, y_1+\Delta y, z_1+\Delta z, \alpha_1+\Delta\alpha, \beta_1+\Delta\beta, \gamma_1+\Delta\gamma]$, where $\Delta x$, for example, represents the difference between the position of biopsy needle 1202 along the X axis as compared to the position $x_1$.

Figure 12C:
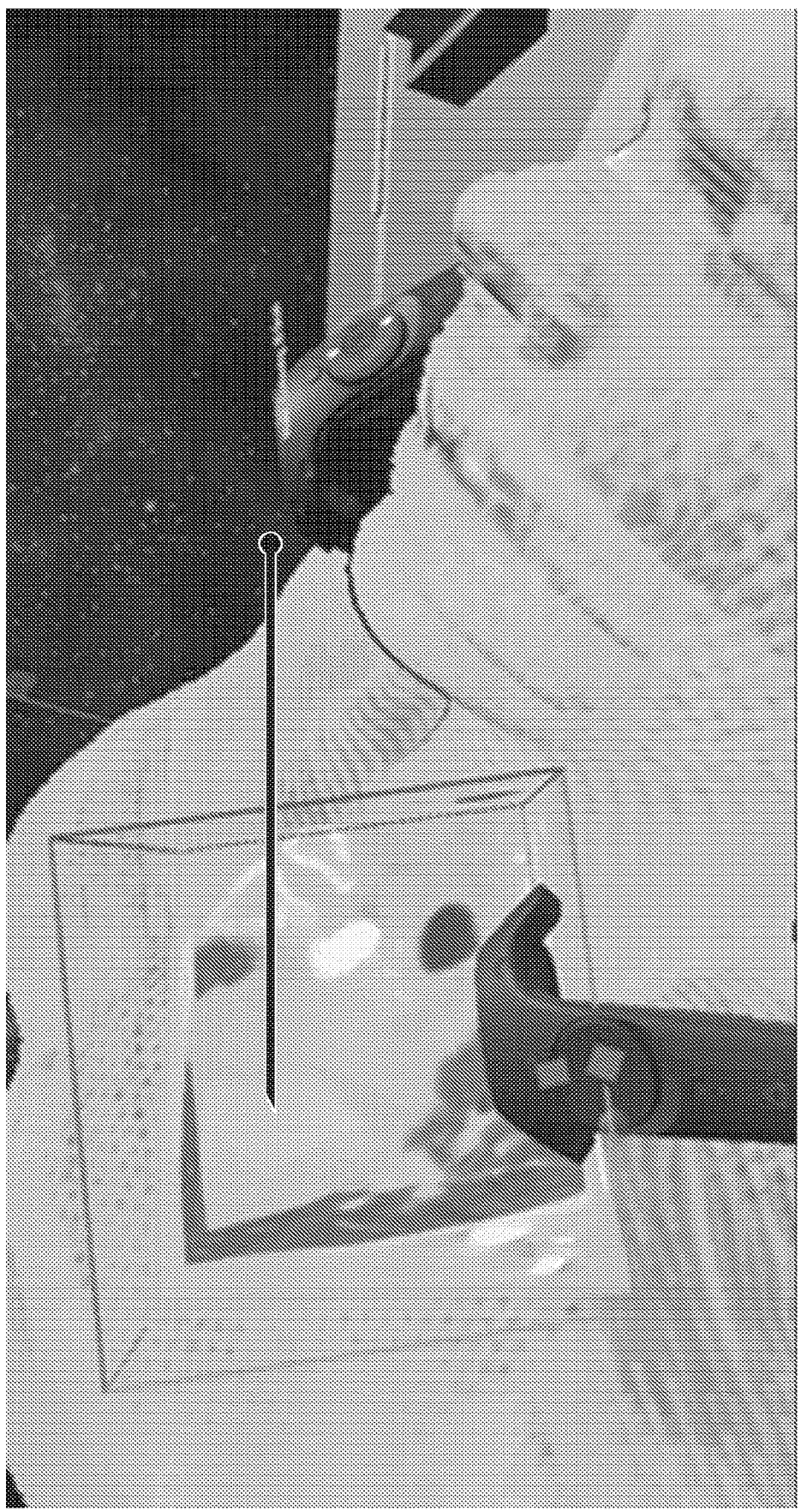
FIG. 12C shows an example of a portion of a 3D model based on a computed tomography scan in which a user interface element is being used to virtually place a virtual surgical tool to plan a route for performing a biopsy on the subject using a system configured in accordance with some embodiments of the disclosed subject matter.

FIG. 12C shows an example of a portion of a 3D model based on a computed tomography scan in which a user interface element is being used to virtually place a virtual surgical tool to plan a route for performing a biopsy on the subject using a system configured in accordance with some embodiments of the disclosed subject matter. As shown in FIG. 12C, a virtual biopsy needle is being inserted into a scan of a subject using user input devices, and a clip object to expose a portion of the interior of the scan of the subject (e.g., to show the anatomy through which the biopsy needle passes).

Figure 12D:
FIG. 12D shows an example of a portion of a 3D model based on a magnetic resonance imaging scan in which virtual labels have been associated with a portion of the 3D model in accordance with some embodiments of the disclosed subject matter.

FIG. 12D shows an example of a portion of a 3D model based on a magnetic resonance imaging scan in which virtual labels have been associated with a portion of the 3D model in accordance with some embodiments of the disclosed subject matter. As shown in FIG. 12D, two labels are associated with portions of the 3D model and/or with a segmentation of the 3D model. In some embodiments, such labels can be inserted manually (e.g., via a user input device) and/or automatically (e.g., in response to user input to add a label to a particular position within the 3D array). In some embodiments, labels can be generated using any suitable input, such as input via a virtual keyboard, via audio (e.g., voice) data, etc.

Figure 13:
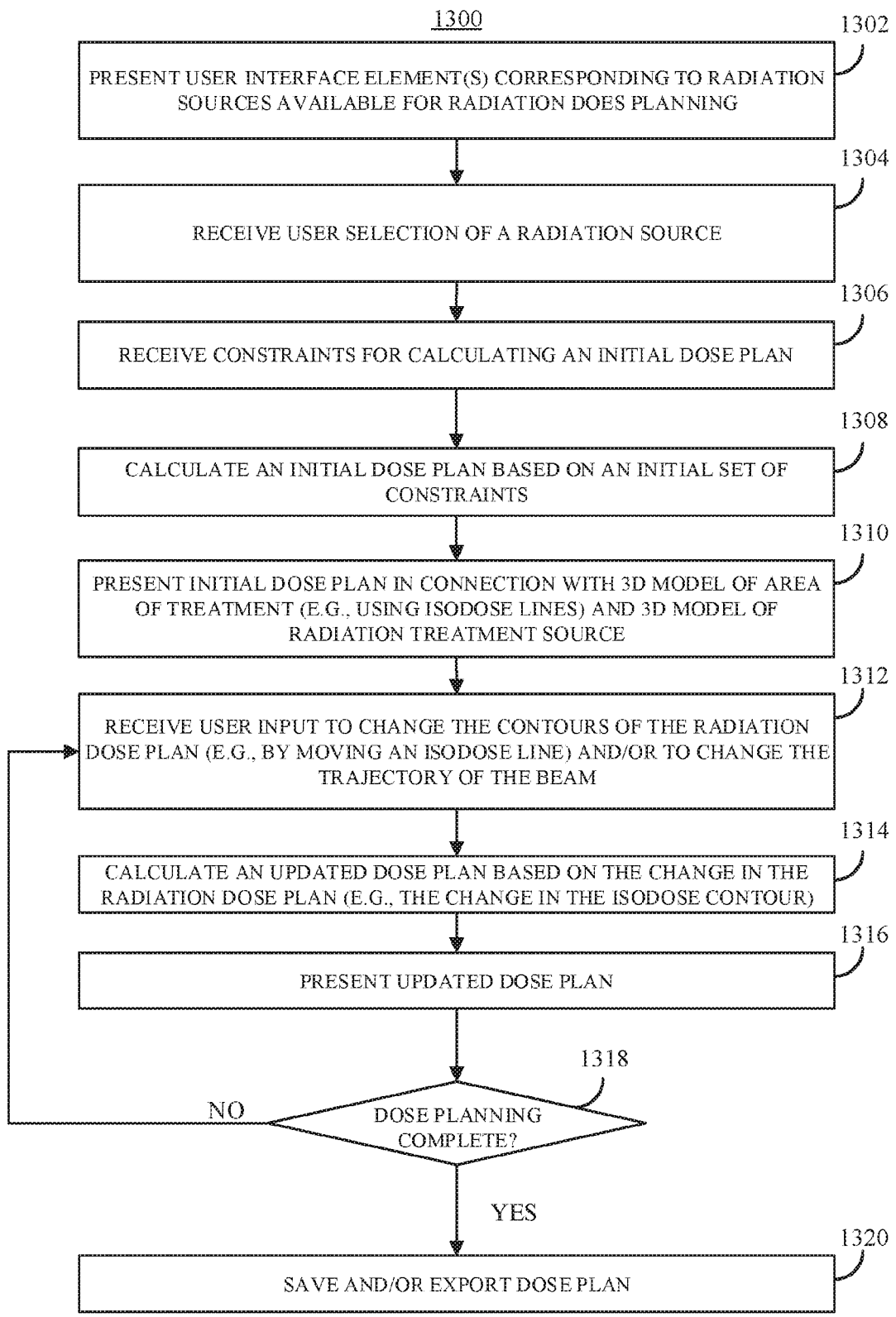
FIG. 13 shows an example 1300 of a process for planning a radiation treatment using a 3D model based on a radiological scan of a subject in a virtual environment in accordance with some embodiments of the disclosed subject matter.

FIG. 13 shows an example 1300 of a process for planning a radiation treatment using a 3D model based on a radiological scan of a subject in a virtual environment in accordance with some embodiments of the disclosed subject matter. Three-dimensional visualization techniques described above (e.g., in connection with FIG. 6) can facilitate radiation therapy treatment planning. Conventional radiation therapy treatment planning is typically performed using software with 2D multi-planar (e.g., axial, sagittal, and coronal) visualization. Radiation dose distributions are calculated and optimized using inverse optimization, typically based on the dose-volume histogram (DVH), and constraints on the radiation targets and organs at risk. Optimization is generally performed by users adjusting constraint weights, and, in some cases using multi-criteria optimization techniques to navigate a pareto-optimal surface of trade-offs between constraints. For example, while metrics and constraints generated by automated systems are useful, a physician is also required to visually check the does plan when evaluating a radiation plan. In a more particular example, even if the average dose to the heart is within a specified tolerance, the physician may notice during a visual inspection that there is a higher than average dose (a "hot spot") at a location that corresponds to a critical cardiac vessel. Based on the visual inspection the physician can attempt to change the radiation plan to decrease or eliminate the hot spot, and avoid potential damage to the critical cardiac vessel.

Current approaches, while allowing for the user to update the dose plan, provide the user with limited information, such as DVH statistics and 2D planar views of individual slices of the dose distribution and anatomy. However, adjustments to optimization tradeoffs in a treatment plan can change many attributes of the dose distribution which do not necessarily exhibit themselves in the DVH metrics or in single 2D planes. The inability to immediately see and appreciate how optimization changes impact in the 3D dose distribution leads to inefficiencies in the treatment planning process. Extending the example above, if the physician attempts to eliminate the hot spot over a particular cardiac vessel, a change that is made can cause changes in another area (e.g., a lower dose than desired in a target area, or a hot spot in another area). Using conventional systems, the physician needs to perform the entire inspection again to ensure that no critical changes have occurred.

In some embodiments, techniques for rendering a 3D array of medical imaging data can be used to display 3D anatomy, with radiation dose displayed as a 3D cloud overlay and/or as a set of isodose contour levels. As described below, to adjust the optimization constraints a user can select a point on an isodose contour or within a 3D cloud, and can move that point in a 3D direction using a 6 DOF user input device. In some embodiments, the techniques described below can be used to adjust the optimization by defining a new dose constraint metric and running a fast re-optimization, or, for multi-criteria optimization techniques, defining a new linear combination of anchor plans such that the isodose level adjusted by the user moves in the specified direction.

As shown in FIG. 13, process 1300 can begin, at 1302, by presenting selectable user interface elements corresponding to various radiation sources that can be used to plan a radiation treatment. In some embodiments, representations of any suitable radiation sources can be made available for planning a radiation treatment using mechanisms described herein. For example, in some embodiments, one or more linear accelerators, any other suitable type(s) of accelerator, one or more brachytherapy structures, one or more sources of non-ionizing energy (e.g., for use in radiofrequency ablation, microwave ablation, high frequency ultrasound, tumor treating fields), etc. Additionally or alternatively, in some embodiments, process 1300 can select a radiation source based on an imported dose plan associated with a particular type of radiation source.

At 1304, process 1300 can receive input indicating a selection of one or more radiation sources. In some embodiments, such input can be provided using any suitable technique or combination of techniques. For example, in some embodiments, a user input device (e.g., user input device 404) can have a dedicated user interface element (e.g., a hardware or software button) that can be used to select a presented user interface element (e.g., a user interface element corresponding to a menu item, a user interface corresponding to a particular radiation source, etc.) when a representation of the user input device is within a threshold distance of the user interface element. In such an example, a user can adjust a position of a user interface element (e.g., a virtual pointer) to a particular position corresponding to the user interface element to be selected, and can initiate selection by actuating the button. As another example, in some embodiments, a selection can be initiated when the user performs one or more gestures associated with a command to select a particular user interface element (e.g., causing a representation of the user input device to actuate a software button presented within the virtual environment without the user actuating a physical button on the user input device). As yet another example, a voice command can be received to select one or more radiation sources.

At 1306, process 1300 can receive one or more constraints for calculating an initial dose plan. Examples of such constraints can include; a location and/or size of the target area; the maximum dose to one or more structures, for example, the maximum dose allowed at any point along a structure in series such as the spinal cord or esophagus; a threshold dose at which a volumetric organ (e.g., the kidney) may start to be impacted; an average dose that is permitted over an entire organ, such as the hear. In some embodiments, the constraints can be received using any suitable technique or combination of techniques. For example, the constraints can be imported from a radiation does plan calculated using a convention dose planning system. As another example, the constraints can be entered by a user using one or more user input devices within the virtual environment (e.g., via user input device 404, one or more menus, one or more virtual keyboards, via one or more voice commands, etc.) or outside the virtual environment (e.g., using a conventional user input device(s), such as a keyboard and mouse or user computing device 430).

At 1308, process 1300 can calculate an initial dose plan based on an initial set of constraints. In some embodiments, any suitable technique or combination of techniques can be used to calculate an initial dose plan, such as through use of a system implementing one or more inverse optimization techniques based on a DVH, and/or one or more multi-criteria optimization techniques to navigate a pareto-optimal surface of trade-offs between constraints.

At 1310, process 1300 can present the initial dose plan calculated at 1308 in connection with the 3D array of medical imaging data in the virtual environment. In some embodiments, process 1300 can use any suitable technique or combination of techniques to present the initial dose plan, such as through the use of 3D isodose surfaces and/or isodose volumes. Additionally, in some embodiments, process 1300 can present a 3D rendering of the one or more selected radiation sources in a position based on the initial dose plan (e.g., the 3D model of the subject can be presented in connection with a table of the radiation source, and the radiation source can be presented with an orientation that could be used to provide the therapeutic treatment associated with the radiation source).

In some embodiments, the mechanisms described herein can provide a user interface to allow a user to control how each isodose contour is presented during rendering. For example, in some embodiments, the mechanisms described herein can provide a user interface that allows a user to select a color to use to draw a particular isodose contour. As another example, in some embodiments, the mechanisms described herein can provide a user interface that allows a user to set the transparency of one or more isodose contours (e.g., individually and/or as a group of two or more, up to all isodose contours). As yet another example, in some embodiments, the mechanisms described herein can provide a user interface that allows a user to toggle presentation of one or more isodose contours to cause presentation to be enabled or disabled, respectively. Additionally, in some embodiments, the mechanisms described herein can provide a user interface that allows a user to specify a range of expected radiation doses to present, and/or specify how certain ranges of expected radiation dose. For example, the mechanisms described herein can provide a slider that allows a user to specify the range of expected doses to show (e.g., from 20 gray (Gy) to 40 Gy), and isodose contours corresponding to expected doses outside of that range can be omitted from presentation. As another example, the mechanisms described herein can provide a user interface that allows the user to specify a particular color at which to present certain ranges of expected dose (e.g., specifying that expected doses of 30 to 40 Gy be presented in one color, and expected doses of 30 to 40 Gy be presented in another color). In some embodiments, the mechanisms described herein can select colors for isodose contours without user intervention (e.g., initial colors can be set without user intervention). Additionally, in some embodiments, as the range is changed (e.g., narrowed or expanded), the mechanisms described herein can reassign new colors to show more or fewer isodose contours to represent a particular range. For example, if a range of 10 to 40 Gy is initially presented using four colors (e.g., at 10, 20, 30, and 40 Gy), and a user specifies that presentation is to be restricted to a range of 30 to 40 Gy, the mechanisms described herein can add isodose curves at 33 and 36 Gy using different colors to show the range in more detail.

Figure 14B:
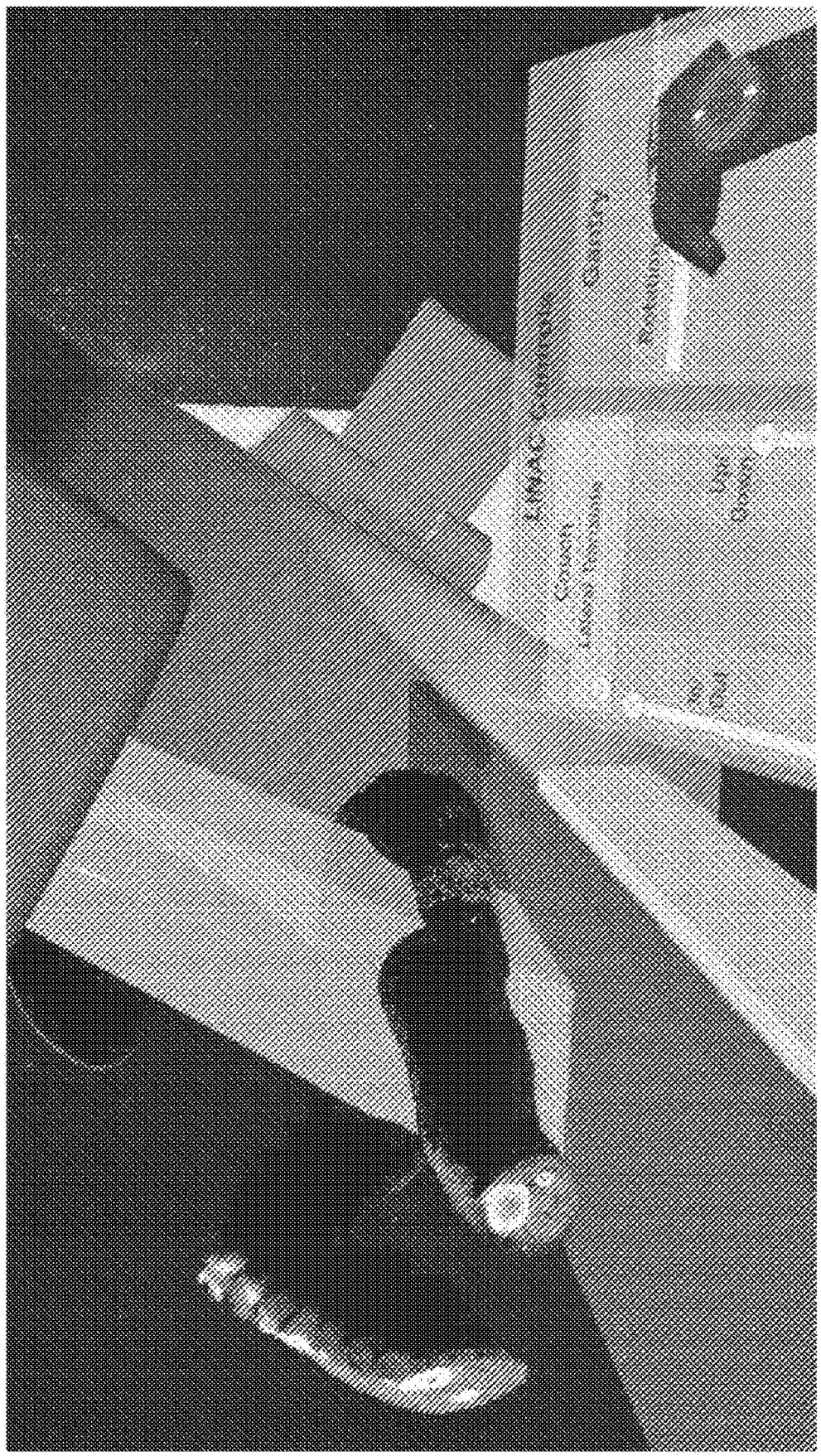
FIG. 14B shows an example of a portion of a 3D model based on a computed tomography scan shown in connection with a radiation source and virtual controls for the radiation source for generating a radiation dose plan using a system configured in accordance with some embodiments of the disclosed subject matter.

At 1312, process 1300 can receive user input to change the contours of the radiation dose plan and/or to change the trajectory of the beam. In some embodiments, process 1300 can receive any suitable user input to change an isodose contour and/or trajectory of a beam. For example, in some embodiments, a user can position a representation of a user input device (e.g., user input device 404, a user's hand, etc.) to select a point (or points) along a surface of a particular isodose contour. In such an example, the user can manipulate the shape of the isodose contour by dragging the selected point(s) to a new position. As another example, in some embodiments, a user can position a representation of a user input device (e.g., user input device 404, a user's hand, etc.) to select a point along a trajectory and/or a portion of the radiation source (e.g., a point on the gantry of a linear accelerator, a point or points along the length of a brachytherapy catheter, etc.). In such an example, by changing the position of the user input device, the user can manipulate the position, orientation, and/or trajectory of the radiation source. Additionally or alternatively, in some embodiments, process 1300 can present virtual controls (e.g., as shown in FIG. 14B, below) for manipulating a radiation source (e.g., to change the position and/or trajectory of the gantry and/or table on which a subject is positioned to receive the radiation treatment). In some embodiments, collisions (e.g., between the gantry, the subject, and/or the table on which the subject is positioned for treatment) can be detected and/or highlighted.

In some embodiments, as a user adjusts the shape of an isodose contour, process 1300 can provide haptic feedback, in which the strength of haptic pulsing can be modulated based on the "difficulty" of the desired user motion (e.g. based on a change in an overall optimization penalty, or on a relative dose gradient at that location in multicriteria optimization anchor plans).

At 1314, process 1300 can calculate an updated dose plan based on changes made to the position of one or more isodose contours, the position of one or more radiation sources, and/or the trajectory of one or more radiation sources. In some embodiments, process 1300 can use any suitable technique or combination of techniques to update the dose plan. For example, process 1300 can adjust and/or create one or more constraints based on the received input, and performing a re-optimization based on the updated constraint(s). As another example, process 1300 can define a new linear combination of anchor plans such that the isodose level adjusted by the user is moved in the direction specified by the user input.

At 1316, process 1300 can present the updated dose plan using techniques similar to techniques described above in connection with 1310. In some embodiments, the updated dose plan can provide immediate visual feedback to a user by showing where a new hotspot has been created, points within the target area that are projected to receive less radiation than specified, etc. In some embodiments, process 1300 can receive user input to change the radiation dose plan that is being presented between a previous dose plan and the current plan, which can be used to identify changes in the dose plan. As another example, process 1300 can use one or more techniques to show areas of the radiation dose plan that changed from the previous radiation does plan (e.g., by altering brightness, color, texture, density, etc., of portions of isodose contours that have changed, by showing a "ghost" of the previous plan, etc.).

In some embodiments, by presenting the updated dose plan using techniques described herein, the user can immediately appreciate the full 3D scope that the changes in the optimization constraints have on the underlying plan. For example, if a user works to constrain an isodose in a particular area, they can immediately see where low doses or hotspots appear elsewhere in the plan and can more quickly appreciate tradeoffs.

At 1318, process 1300 can determine if a dose planning operation has been completed. For example, process 1300 can receive input indicating that the radiation planning operation has ended, such as an explicit input to cease such an operation, input to enter a different mode, etc.

If process 1300 determines that the radiation planning operation has not ended ("NO" at 1318), process 1300 can return to 1312 to continue to receive user input to change the radiation dose plan. Otherwise, if process 1300 determines that the radiation planning operation has ended ("YES" at 1318), process 1300 can move to 1320 to save and/or export the radiation dose plan for later use in connection a radiation therapy and/or future radiation dose planning.

Although process 1300 is generally described in connection with radiation beam therapies, process 1300 can also be used in connection with planning other types of radiation treatments. For example, brachytherapy is a type of radiation treatment in which radioactive sources are placed directly on (or within) a target area of tissue. For example, brachytherapy can be used at the skin surface for treating superficial cancers and nonmalignant conditions, or intra-operatively at a surgical resection bed. In some embodiments, brachytherapy plans can be generated by creating segmentations of curved brachytherapy catheters, the accuracy of which can be crucial for accurately modeling the distribution of the radiation dose. Because brachytherapy catheters do not typically fall within a single imaging plane, planning using conventional tools can be a difficult and time consuming process. In some embodiments, contouring and dose calculation techniques described herein can be applied to brachytherapy, by allowing a user to place the catheters in three dimensions, to define radiation dose at points along the catheters while viewing the dose distribution in real-time (or near real-time) on a 3D model of the subject. Additionally, in some embodiments, resection techniques (e.g., described above in connection with FIG. 9) can be used with the dose planning techniques described herein to plan complex intraoperative cases.

FIG. 14A1 shows an example 1400 of a clip object intersecting a portion of a 3D model exposing medical imaging data at the boundary of the clip object and isodose contours showing the expected amount of radiation different portions of the subject's anatomy would be exposed to based on a particular radiation does plan in accordance with some embodiments of the disclosed subject matter. As shown in FIG. 14A1, isodose contours 1402 and 1404, representing different projected doses of radiation, can be rendered over medical imaging data from the 3D array of medical imaging data that is shown at the boundaries of clip object 202. Additionally, a representation 1406 of a gantry of a radiation source, and a radiation beam 1408 can be presented to provide additional information regarding the radiation dose plan. Note that although isodose contours 1402 and 1404 are represented in FIG. 14A1 as surfaces, showing the 2D radiation dose for two areas of object 102, this is merely an example. In some embodiments, isodose contours 1402 and/or 1404 can be presented as 3D volumes (e.g., that are at least partially transparent to allow underlying medical imaging data to be viewed simultaneously with the isodose contour). In some embodiments, the mechanisms described herein can represent isodose curves using any suitable technique or combination of techniques, such as by using one or more binary masks to determine which voxels particular isodose contours include. In some embodiments, although only a portion of an isodose contour may be presented (e.g., as shown in FIG. 14A1), the mechanisms described herein can store information on the location and/or dimensions of the isodose contours across the entire object.

FIG. 14A2 shows an example 1410 of a cross-section view of the object shown in FIG. 14A1 illustrating that, although 2D cross sections of the isodose contours are shown in FIG. 14A1 at the boundary of the clip object, the full three dimensional extent of the isodose contours can be calculated for portions of the medical imaging data not currently rendered in the example shown in FIG. 14A1 in accordance with some embodiments of the disclosed subject matter. As shown in FIG. 14A2, portions 1412 of isodose curves 1402 and 1404 can correspond to an area within a clip object (e.g., clip object 202). In some embodiments, one or more portions 1412 of isodose contours that extend into a clip object can be omitted from being rendered (e.g., to avoid overwhelming a user with information). Additionally or alternatively, in some embodiments, one or more 1412 of isodose contours that extend into a clip object can be presented as partially transparent to allow the information behind it (e.g., from a user's point of view) to also be rendered.

FIG. 14B shows an example of a portion of a 3D model based on a computed tomography scan shown in connection with a radiation source and virtual controls for the radiation source for generating a radiation dose plan using a system configured in accordance with some embodiments of the disclosed subject matter. As shown in FIG. 14B, a 3D model of a subject is rendered with a model of a linear accelerator that can project a radiation beam to provide a radiation treatment. Virtual controls for the linear accelerator are also shown in FIG. 14B, which can be used to adjust the trajectory of the radiation treatment.

Figure 14C:
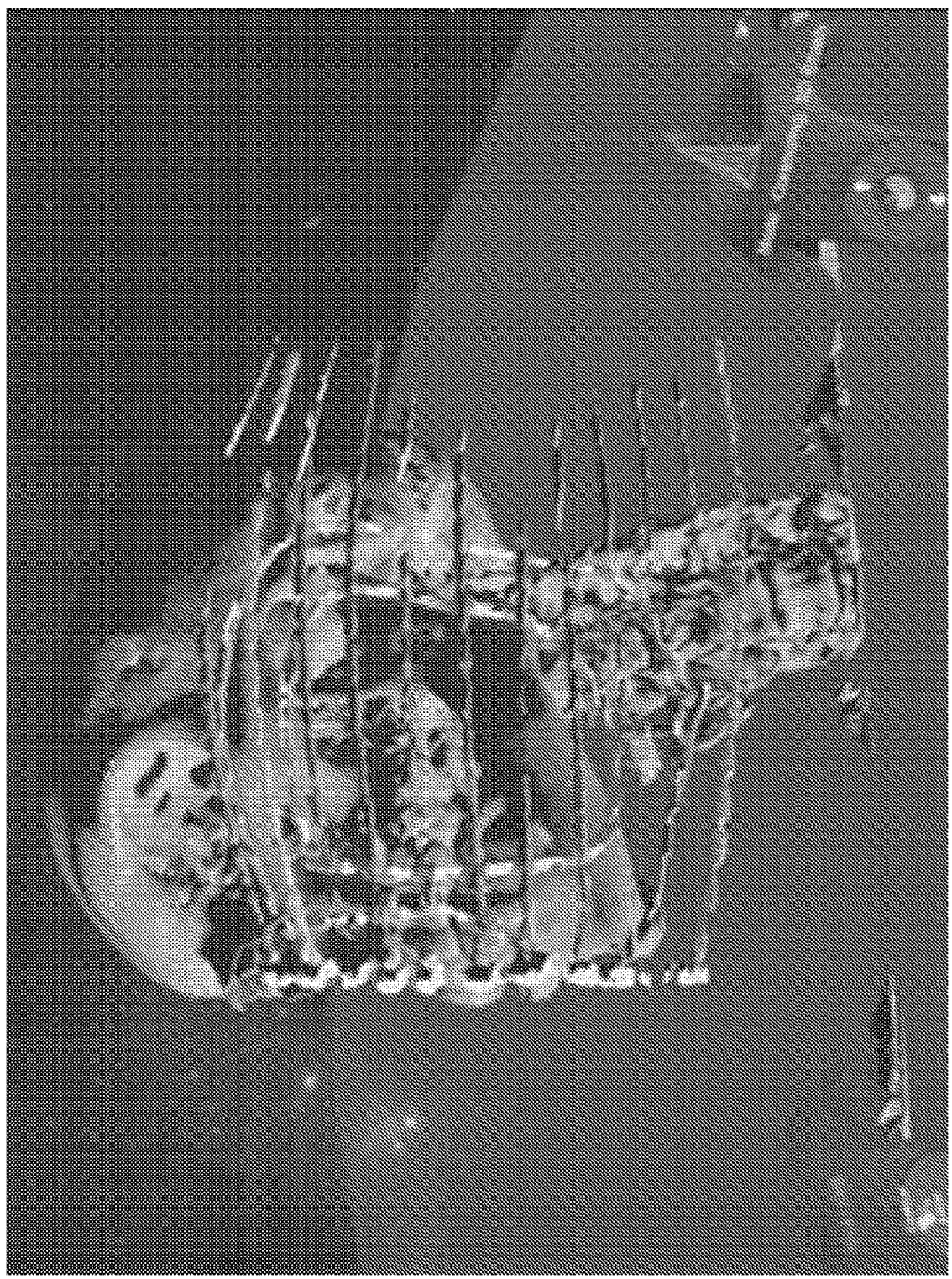
FIG. 14C shows an example of a portion of a 3D model based on a computed tomography scan shown in connection with virtual brachytherapy catheters for generating a radiation dose plan for a superficial cancer using a system configured in accordance with some embodiments of the disclosed subject matter.

FIG. 14C shows an example of a portion of a 3D model based on a computed tomography scan shown in connection with virtual brachytherapy catheters for generating a radiation dose plan for a superficial cancer using a system configured in accordance with some embodiments of the disclosed subject matter. As shown in FIG. 14C, various brachytherapy catheters are shown in connection with a portion of a medical imaging scan corresponding to a subject's skeletal system.

Figure 15:
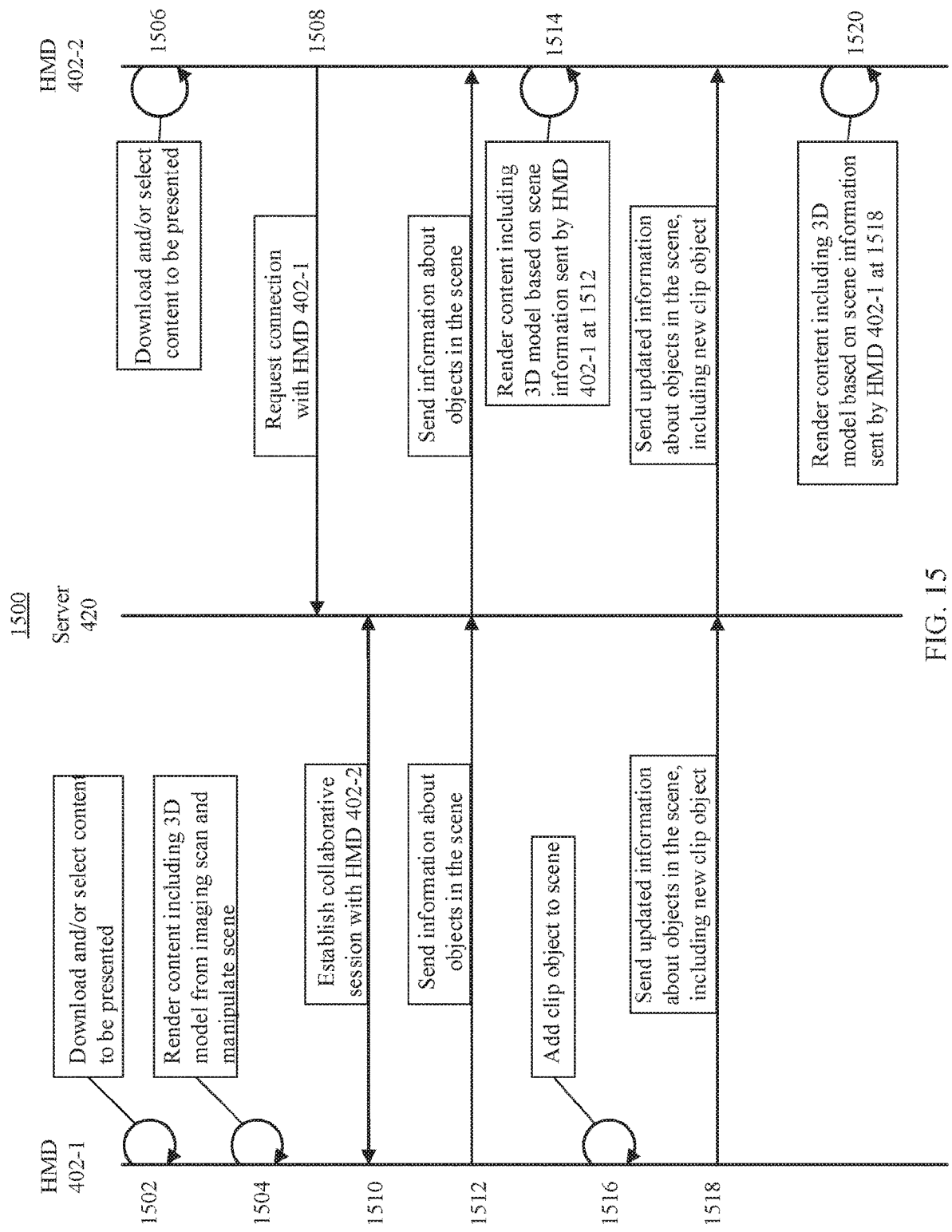
FIG. 15 shows an example 1500 of a flow among a first HMD 402-1, a server 430, and a second HMD 402-2 to facilitate a collaborative experience for viewing medical imaging data in an interactive virtual reality environment in accordance with the presentation in accordance with some embodiments of the disclosed subject matter.

FIG. 15 shows an example 1500 of a flow among a first HMD 402-1, a server 430, and a second HMD 402-2 to facilitate a collaborative experience for viewing medical imaging data in an interactive virtual reality environment in accordance with the presentation in accordance with some embodiments of the disclosed subject matter. As shown in FIG. 15, at 1502, a first HMD (e.g., HMD 402-1), can download and/or select content to be presented. In some embodiments, HMD 402-1 can select any suitable content to be presented, such as a 3D array of medical imaging data generated by a CT scan or an MRI scan.

At 1504, HMD 402-1 can render at least a portion of the content including a 3D model based on the medical imaging data produced by the scan. Additionally, in some embodiments, HMD 402-1 can facilitate manipulation of the content (e.g., using one or more user input devices) to cause different portions of the content to be rendered.

At 1506, a second HMD (e.g., HMD 402-2) can download and/or select the same content to be presented. In some embodiments, HMD 402-2 can select the content based on any suitable input, such as input from a user affirmatively selecting particular content, input from a user confirming that the user wishes to participate in a collaborative session with HMD 402-1, etc.

At 1508, HMD 402-2 can send a request to be connected to HMD 402-1 via a server 420, which can serve as an intermediary between HMD 402-1 and 402-2. Note that, in some embodiments, server 420 can be omitted, and HMD 402-1 or 402-2 can act as a server.

At 1510, server 420 can interact with HMD 402-1 to establish a collaborative session that includes HMD 402-1 and HMD 402-2. For example, in some embodiments, server 420 can cause a user of HMD 402-1 to be prompted to consent to joining the collaborative session, server 420 can gather information about HMD 402-1 and/or establish a link to HMD 402-1, etc.

At 1512, HMD 402-1 can send information about objects in the scene being rendered by HMD 402-1 to HMD 402-2 (e.g., via server 420). For example, the information can include the location and/or orientation of the object(s), the scale at which the object(s) is being rendered, identifying information of the object(s), whether a filter is enabled, information about one or more segmentations that have been added to the content, etc.

At 1514, HMD 402-2 can independently render content corresponding to the content being rendered by HMD 402-1 based on the information sent at 1512. For example, HMD 402-2 can render the objects in the scene being rendered by HMD 402-1 from a different point of view based on the information on the location and/or orientation of the objects. In some embodiments, this can result in users of HMD 402-1 and HMD 402-2 being presented with very different scenes, as a portion of an object that is not rendered by one HMD (e.g., because it is on an opposite side of the object from the user's point of view) may be rendered by the other HMD if it is rendering the scene from a point of view on the opposite side of the object.

At 1516, HMD 402-1 can add a clip object to the scene (e.g., as described above in connection with FIG. 6), and can communicate information about the new clip object by sending, at 1518, updated information about objects in the scene. At 1520, HMD 402-2 can render the clip object based on the updated information sent at 1518. By sending updated information, HMD 402-1 and/or HMD 402-2 can render synchronized, although the content is being rendered by a particular HMD. For example, this can ensure that when a user of HMD 402-2 moves around the object to a point of view similar to the point of view being used to render content for HMD 402-1, HMD 402-2 can render the content to allow the user's to view the same information (if from different points of view) and share a common experience.

As described above, in some embodiments, the mechanisms described herein can be used by multiple users to enhance visual communication about medical imaging data. For example, if each user is utilizing a HMD (e.g., HMD 402) and tracked hand controllers (e.g., user input device 404), the users can collaborate to manipulate a shared set of 3D medical images using the mechanisms described herein, such as visualization techniques and clip-objects (e.g., as described above in connection with FIGS. 6 and 7), contouring techniques (e.g., as described above in connection with FIG. 9), and radiation and/or surgical planning techniques (e.g., as described above in connection with FIGS. 11 and 13). In some embodiments, prior to (or as part of the initialization of) a multiuser interaction, different HMDs to be used in the multiuser interaction can load the same 3D array of medical imaging data. While users are connected via their respective HMDs, information about HMDs, hand controllers, objects, clip objects, voice data, segmentation arrays, etc., can be passed between HMDs in real time to ensure that each user is able to see the same instance of a scene. Additionally, specific user interface features can be used to facilitate provider-provider interactions or provider-patient interactions, respectively.

In some embodiments, two or more medical providers can use the mechanisms described herein to jointly annotate and communicate about a set of medical images. For example, the providers can be located near one anther (e.g., in the same room, building, building complex, campus, city, etc.) and/or remotely located (e.g., not able to physically view the same display device, such as located in different rooms, different buildings, different campuses, different cities, etc.). In some embodiments, the mechanisms described herein can facilitate communication between physicians. For example, the mechanisms can be utilized to discuss a surgical approach with a co-located or remotely located colleague. As another example, the mechanisms can be utilized to discuss radiation planning data with one or more other healthcare providers. As yet another example, the mechanisms can be utilized to facilitate a virtual tumor board. As still another example, the mechanisms can be utilized to discuss facilitate communication or joint review of a radiation treatment plan between a radiation oncologist and a dosimetrist or medical physicist, quality assurance rounds between medical providers, medical education of normal anatomy and pathology, etc.

In some embodiments, the mechanisms described herein can provide a set of tools to allow a medical provider to communicate information to patients about their diagnosis and treatment plan more effectively. For example, the mechanisms can be used to teach patients about their diagnosis, such as by illustrating involvement with a brain tumor, a plan for how a patient's surgery is going to be performed and/or a discussion of hot their surgery was performed, a discussion of which areas are at risk for recurrence (e.g., by showing the interrelation of the different portions of the patients anatomy). In a more particular example, a patient who has a diagnosis of an atypical meningioma (brain tumor) based on an MRI scan may be interested in learning from her neurosurgeon about the location of her tumor in relation to normal parts of the brain. Using the mechanisms described herein, the surgeon can view the imaging in VR together with the patient explaining and illustrating where an incision is planned and what areas of the brain may be impacted by the planned surgery (e.g., using segmentation and/or resection techniques described above in connection with FIG. 7 and/or surgical planning techniques described above in connection with FIG. 9). This can facilitate a discussion about informed consent (e.g., the benefits and downsides of a particular treatment). After surgery, this patient have a positive margin requiring post-operative radiation therapy. A radiation oncologist can review her preoperative and post-operative imaging with the patient, and use the mechanisms described herein to facilitate a discussion of how a particular radiation treatment might impact the patient and the patient's quality of life. This can involve, for example, highlighting a particular isodose line to help the patient visualize (e.g., on a model of herself created from a CT or MRI taken for the purpose of planning a radiation treatment) the expected location(s) of hair loss from radiation, or areas of skin which might get red (i.e., due to radiation dermatitis).

As another example, the mechanisms described herein can be used to demonstrate radiation treatment plans, such as which areas are being targeted with radiation, which areas are being avoided, the expected/possible toxicity of treatment across different organs/systems (e.g., radiation dermatitis over right forehead, hair loss in occiput, etc.).

In some embodiments, any suitable computer readable media can be used for storing instructions for performing the functions and/or processes described herein. For example, in some embodiments, computer readable media can be transitory or non-transitory. For example, non-transitory computer readable media can include media such as magnetic media (such as hard disks, floppy disks, etc.), optical media (such as compact discs, digital video discs, Blu-ray discs, etc.), semiconductor media (such as RAM, Flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, any other suitable media that is fleeting and devoid of any semblance of permanence during transmission, and/or any suitable intangible media.

It will be appreciated by those skilled in the art that while the disclosed subject matter has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is hereby incorporated by reference, as if each such patent or publication were individually incorporated by reference herein.

Various features and advantages of the invention are set forth in the following claims.

The invention claimed is:
1. A system for presenting medical imaging data in an interactive virtual reality environment, comprising:
  a head mounted display (HMD) comprising:
    at least one display comprising a plurality of pixels;

memory storing a three dimensional (3D) array of voxel values corresponding to a medical imaging scan of a subject, wherein the 3D array includes a plurality of internal voxels corresponding to interior anatomy of the subject and a plurality of external voxels corresponding to an exterior surface of the subject; and at least one hardware processor that is programmed to:
determine a position of a first 3D object in a scene to be presented using the at least one display, wherein the first 3D object is a 3D representation of the subject based on the 3D array of voxel values;

determine a position of a second 3D object comprising a surface in the scene to be rendered;

determine, based on the position of the first object and the position of the second object, that the second 3D object overlaps at least a portion of the first 3D object;

determine, for a first subset of pixels of the plurality of pixels, that the second 3D object is positioned between the pixel and the first 3D object;

set a value for each of the first subset of pixels based on a value of an interior voxel at a position in the 3D array corresponding to the point at which the surface of the second 3D object and a ray cast from the pixel intersect without shading effects;

determine, for a second subset of pixels of the plurality of pixels, that the second 3D object is not positioned between the pixel and the first 3D object;

set a value for each of the second subset of pixels based on a value of an exterior voxel at a position in the 3D array corresponding to the point at which the surface of the first 3D object and a ray cast from the pixel intersect with at least one shading effect; and present, using the at least one display, an image of the scene, the first subset of pixels depicting an interior portion of the subject's anatomy without shading effects, and the second subset of pixels depicting the exterior surface of the subject.

2. The system of claim 1, wherein the at least one hardware processor is further programmed to:
render a bounding box having dimensions that encompass the first 3D object; and
determine a distance from each of the plurality of pixels to the front of the bounding box.

3. The system of claim 2, wherein the at least one hardware processor is further programmed to:
generate, for each pixel of the second subset of pixels, a ray directed through the pixel toward the scene, and begin a ray marching operation from the front of the bounding box based on the distance from the pixel to the front of the bounding box;
advance, for each of the plurality of pixels, the ray by a distance that is less than the diameter of a voxel in the 3D array of imaging data; and
after advancing the ray, determine that the ray has satisfied a stopping condition.

4. The system of claim 3, wherein the at least one hardware processor is further programmed to:
determine, after advancing the ray, that the ray position corresponds to a voxel in the 3D array of imaging data;

in response to determining that the ray position corresponds to a voxel in the 3D array of imaging move the ray backward by a second distance that is less than the distance;
determine, after moving the ray backward, that the ray position does not corresponds to a voxel in the 3D array of imaging data.

5. The system of claim 2, wherein the at least one hardware processor is further programmed to:
determine a distance from each pixel of the first subset of pixels to the back of the second object;
determine, for each pixel of the subset of pixels, that the distance to back of the second object is larger than the distance to the front of the bounding box;
in response to determining, for each pixel of the subset of pixels, that the distance to back of the second object is larger than the distance to the front of the bounding box, generate a ray directed through the pixel toward the scene, and begin a ray marching operation from the back of the second object based on the distance from the pixel to the back of the second object.

6. The system of claim 1, wherein the at least one hardware processor is further programmed to:
render distances to one or more surfaces of the second 3D object based on a mesh representation of the second 3D object; and
store the distances to the one or more surfaces as a texture in a texture buffer associated with one or more of the at least one hardware processor.

7. The system of claim 1, wherein the at least one hardware processor is further programmed to:
determine for each of a second plurality of pixels of the at least one display, that neither the first 3D object nor the second 3D object is positioned in a line of sight of the pixel; and
in response to determining that neither the first 3D object nor the second 3D object is positioned in a line of sight of the pixel, set a value for the pixel based on a background image.

8. The system of claim 1, wherein the at least one hardware processor is further programmed to:
subsequent to presenting the image of the scene, receive an instruction to inhibit voxels having intensity values outside of a range of intensity values from being presented;
determine, for a third subset of pixels of the plurality of pixels, that the second 3D object is not positioned between the pixel and the first 3D object;
generate, for each pixel of the third subset of pixels, a ray directed through the pixel toward the scene;
advance, for each pixel of the third subset of pixels, the ray by a predetermined distance until the ray encounters a first voxel of the 3D array along the path of the ray;
in response to encountering the first voxel, determine that an intensity value associated with the first voxel falls outside of the range of intensity values;
in response to determining that a value associated with the first voxel falls outside of the range of intensity values, inhibit the voxel from being rendered;
continue to advance the ray until a voxel associated with an intensity value within the range of intensity values;
set a value for each of the third subset of pixels using at least one shading effect and based on the intensity value of the voxel associated with the intensity value within the range of intensity values at a position in the 3D array corresponding to the point at which the ray cast from the pixel intersects the voxel associated the intensity value within the range of intensity values; and
present, using the at least one display, an image of the scene, the third subset of pixels depicting an interior portion of the subject's anatomy as a 3D surface with shading effects.

9. The system of claim 1, the system further comprising a user input device, wherein the at least one hardware processor is further programmed to:
receive input to initiate a contouring operation;
present a 3D user interface element in association with a virtual representation of the user input device;
identify a plurality of voxels of the 3D array that are within a threshold distance of a center of the 3D user interface element;
add one or more of the plurality of voxels within the threshold distance to a binary mask as voxels to be associated with a contour; and
present, at the location of each voxel included in the binary mask, a particular color indicating that the voxel is associated with the contour.

10. The system of claim 9, wherein the at least one hardware processor is further programmed to:
determine that the contouring operation is a 3D contouring operation;
in response to determining that the contouring operation is a 3D contouring operation, add each of the plurality of pixels within the threshold distance to the binary mask.

11. The system of claim 9, wherein the at least one hardware processor is further programmed to:
determine that the contouring operation is a 2D contouring operation;
add voxels used to render the first 3D object in the image, including voxels corresponding to the first subset of pixels and the second subset of pixels, to a 2D mask;
determine, for each of the plurality of voxels of the 3D array that are within the threshold distance of a center of the 3D user interface element, whether the voxel is included in the 2D mask;
in response to determining that a particular voxel of the plurality of voxels is not included in the 2D mask, inhibit the voxel from being added to the binary mask; and
in response to determining that a particular voxel of the plurality of voxels is included in the 2D mask, add the voxel to the binary mask.

12. The system of claim 9, wherein the at least one hardware processor is further programmed to:
receive an instruction to inhibit voxels having intensity values outside of a range of intensity values from being presented;
determine, for each of the plurality of voxels of the 3D array that are within the threshold distance of a center of the 3D user interface element, whether an intensity value of the voxel is within the range of intensity values;
in response to determining that a particular voxel of the plurality of voxels has an intensity value that is not within the range of intensity values, inhibit the voxel from being added to the binary mask; and
in response to determining that a particular voxel of the plurality of voxels has an intensity value that is within the range of intensity values, add the voxel to the binary mask.

13. The system of claim 9, wherein the at least one hardware processor is further programmed to:
cause the user input device to provide haptic feedback based at least in part on an intensity value of one or more of the voxels of the plurality of voxels of the 3D array that are within the threshold distance of a center of the 3D user interface element.

14. The system of claim 1, wherein the at least one hardware processor is further programmed to:
present, using the at least one display, a virtual surgical instrument;
receive input to position the virtual surgical instrument to intersect at least a portion of the 3D array; and
present an image that includes at least a portion of the virtual surgical instrument and at least a portion of interior voxels adjacent to the virtual surgical instrument.

15. The system of claim 14, wherein the at least one hardware processor is further programmed to:
associate the virtual surgical instrument with the first 3D object;
define a position of the virtual surgical instrument using relative coordinates based on a position of the first 3D object; and
render the virtual surgical object in a position based on the relative coordinates and the position of the first 3D object in the scene.

16. The system of claim 1, wherein the at least one hardware processor is further programmed to:
generate, based on a first radiation dose plan, a plurality of isodose contours that are each associated with a position within the first 3D object and a shape;
present, using the at least one display, the plurality of isodose contours in association with the first 3D object;
receive input to change the shape of a portion of a first isodose contour of the plurality of isodose contours to a new shape;
calculate a second radiation dose plan based on the new shape of the first isodose contour;
generate, based on the second radiation dose plan, a second plurality of isodose contours that are each associated with a position within the first 3D object and a shape;
present, using the at least one display, the second plurality of isodose contours in association with the first 3D object.

17. The system of claim 16, wherein the at least one hardware processor is further programmed to present a virtual radiation source based on the first radiation dose plan in a configuration corresponding to a configuration that a radiation source providing a radiation treatment based on the first radiation dose plan will be instructed to achieve.

18. The system of claim 1, wherein the at least one hardware processor is further programmed to:
receive a message indicating that a second HMD has initiated a collaborative session with the HMD;
received information indicating locations and orientations of a plurality of objects, including the first 3D object and the second 3D object within a virtual reality environment being rendered by the second HMD;
causing the first 3D object and the second 3D object to be positioned based on the received information to facilitate a shared experience with the second HMD.

19. The system of claim 1, wherein the at least one hardware processor comprises a graphics processing unit (GPU).

20. The system of claim 1, further comprising a user input device comprising:
a plurality of sensors; and at least one second hardware processor that is programmed to:
  receive outputs from each of the plurality of sensors;
  determine movements of the user input device along three orthogonal axes and rotations of the user input device around each of the three orthogonal axes; and
  send information to the HMD indicative of movements of the user input device;
wherein the at least one hardware processor is further programmed to:
  receive the information indicative of movements of the user input device; and
  change a position of the second 3D object within the virtual reality environment based on the movements of the user interface indicated by the received information.

21. A system for presenting medical imaging data in an interactive virtual reality environment, comprising:
  memory storing volumetric medical imaging data of a patient organized into a three dimensional (3D) array of voxels, wherein the voxels including a plurality of internal voxels corresponding to interior anatomy of the patient and a plurality of external voxels corresponding to an exterior surface of the patient; and
  at least one hardware processor that is programmed to:
    cause a 3D model of the subject to be rendered based on the 3D array of voxels;
    cause a clip object having a regular geometric shape to be rendered;
    determine based on the rendering of the 3D model and the rendering of the clip object, locations at which a portion of the clip object overlaps the 3D model of the subject;
    cause a first portion of the 3D model that does not overlap the clip object, and that is in a line of sight of a virtual camera used to generate an image for presentation, to be rendered using one or more shading operations to determine intensity values to be used when displaying the first portion of the 3D model;
    cause portions of the 3D model that are within a volume defined by the clip object to be ignored;
    cause a second portions of the 3D model that is along a boundary between the clip object and the 3D model, and that is in a line of sight of the virtual camera, to be rendered using intensity values of the voxels corresponding to the second portion without adjusting the intensity via shading; and
    causing an image to be presented that includes the first portion of the 3D model with shading, and the second portion of the 3D model without shading.

* * * * *

UNITED STATES PATENT AND TRADEMARK OFFICE
CERTIFICATE OF CORRECTION

| | | |
|---|---|---|
| PATENT NO. | : 10,932,860 B2 | Page 1 of 1 |
| APPLICATION NO. | : 16/609055 | |
| DATED | : March 2, 2021 | |
| INVENTOR(S) | : Konstantin Kovtun et al. | |

It is certified that error appears in the above-identified patent and that said Letters Patent is hereby corrected as shown below:

In the Specification

Column 1, Line 13, "2017, which, Each" should be --2017. Each--.

Column 6, Line 14, "the mod& exposing" should be --the model exposing--.

Signed and Sealed this
Fifteenth Day of June, 2021

Drew Hirshfeld
*Performing the Functions and Duties of the*
*Under Secretary of Commerce for Intellectual Property and*
*Director of the United States Patent and Trademark Office*